US009442098B2

(12) United States Patent
Thorson et al.

(10) Patent No.: US 9,442,098 B2
(45) Date of Patent: Sep. 13, 2016

(54) CHROMATOGRAPHIC SYSTEM QUALITY CONTROL REFERENCE MATERIALS

(71) Applicant: Waters Technologies Corporation, Milford, MA (US)

(72) Inventors: Karen Thorson, Douglas, MA (US); Jonathan Turner, North Attleboro, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 508 days.

(21) Appl. No.: 13/957,563

(22) Filed: Aug. 2, 2013

(65) Prior Publication Data

US 2014/0033793 A1 Feb. 6, 2014

Related U.S. Application Data

(60) Provisional application No. 61/678,949, filed on Aug. 2, 2012.

(51) Int. Cl.
*G01N 33/00* (2006.01)
*G01N 30/86* (2006.01)
*G01N 30/04* (2006.01)

(52) U.S. Cl.
CPC ...... *G01N 33/0006* (2013.01); *G01N 30/8665* (2013.01); *G01N 2030/042* (2013.01)

(58) Field of Classification Search
CPC ..................................................... G01N 33/00
USPC ...................................................... 436/8, 161
See application file for complete search history.

(56) References Cited

U.S. PATENT DOCUMENTS 5,057,224 A * 10/1991 Shiao ................. C07J 9/005
                                                       210/198.2
5,211,993 A *  5/1993 Kolesinski ............ B01J 20/286
                                                       210/198.2

(Continued)

OTHER PUBLICATIONS

Smith, R. M., Analytical Chemistry 1984, 56, 256-262.*

(Continued)

*Primary Examiner* — Arlen Soderquist
(74) *Attorney, Agent, or Firm* — McCarter & English, LLP; Deborah M. Vernon

(57) ABSTRACT

The invention provides compositions and methods for chromatographic analysis and system quality control. Compositions can include a reference material that comprises a standardized formulation of two or more compounds that can be used for benchmarking and troubleshooting the chromatographic system (e.g., which is not simply a standard solution for a particular analyte of interest). Methods can include obtaining a chromatogram from a reference material using a chromatographic system, wherein the reference material comprises a standardized formulation of two or more compounds that can be used for benchmarking and troubleshooting the chromatographic system; evaluating a difference between the chromatogram and a benchmark for the reference material on the chromatography system; and (i) analyzing a sample potentially comprising an analyte of interest, wherein the analyte of interest does not comprise any of the two or more compounds of the standardized formulation, or compounds substantially similar thereto, if the difference between the chromatogram and the benchmark is within a predetermined tolerance, or (ii) troubleshooting the chromatography system using the chromatogram if the difference between the chromatogram and the benchmark is not within the predetermined tolerance.

21 Claims, 41 Drawing Sheets

(56) References Cited

U.S. PATENT DOCUMENTS

| | | | | |
|---|---|---|---|---|
| 6,456,955 B1* | 9/2002 | Andrews | G01N 30/88 | 210/198.2 |
| 6,962,658 B2* | 11/2005 | Neyer | G01N 30/16 | 210/101 |
| 7,135,300 B2* | 11/2006 | Chan-Hui | G01N 33/542 | 435/7.1 |
| 7,537,703 B2* | 5/2009 | Nakajima | B01J 20/286 | 210/198.2 |
| 7,938,961 B2* | 5/2011 | Plumb | G01N 30/6078 | 210/198.2 |
| 8,501,487 B2* | 8/2013 | Krokhin | C07K 7/06 | 436/86 |
| 2002/0107652 A1* | 8/2002 | Andrews | G01N 30/88 | 702/104 |
| 2004/0091400 A1* | 5/2004 | Wada | C08F 220/06 | 422/400 |
| 2004/0232080 A1* | 11/2004 | Neyer | G01N 30/16 | 210/656 |
| 2005/0224414 A1* | 10/2005 | Izzo | G01N 30/603 | 210/656 |
| 2005/0226536 A1* | 10/2005 | Fasulo | G01N 30/8675 | 382/294 |
| 2006/0016755 A1* | 1/2006 | Plumb | G01N 30/6078 | 210/656 |
| 2006/0144770 A1* | 7/2006 | Granger | B01J 19/0093 | 210/198.2 |
| 2008/0053894 A1* | 3/2008 | O'Gara | B01J 20/103 | 210/502.1 |
| 2008/0110814 A1* | 5/2008 | Izzo | G01N 30/603 | 210/198.2 |
| 2008/0249326 A1* | 10/2008 | Nakajima | B01J 20/286 | 556/410 |
| 2011/0219858 A1* | 9/2011 | Krokhin | C07K 7/06 | 73/61.52 |
| 2014/0024132 A1* | 1/2014 | Jia | G01N 33/5088 | 436/173 |

OTHER PUBLICATIONS

Neue, U. D. et al, Journal of Chromatography A 1999, 849, 87-100.*
Neue, U. D. et al, Journal of Chromatography A 1999, 849, 101-116.*
Kele, M. et al, Journal of Chromatography A 2002, 960, 19-49.*
Deport, C. et al, Journal of Chromatography A 2006, 1116, 248-258.*
Sangster, T. et al, Analyst 2006, 131, 1075-7078.*
Gika, H. G. et al, Journal of Proteome Research 2007, 6, 3291-3303.*
Gika, H. G. et al, Journal of Chromatography B 2008, 871, 299-305.*
Gritti, F.et al, Journal of Chromatography A 2010, 1217, 3000-3012.*
Analytical Standards and Reagents, Waters Corporation Mar. 2012, 8 pages, downloaded from http://www.waters.com/webassets/cms/library/docs/720004230en.pdf.*

* cited by examiner

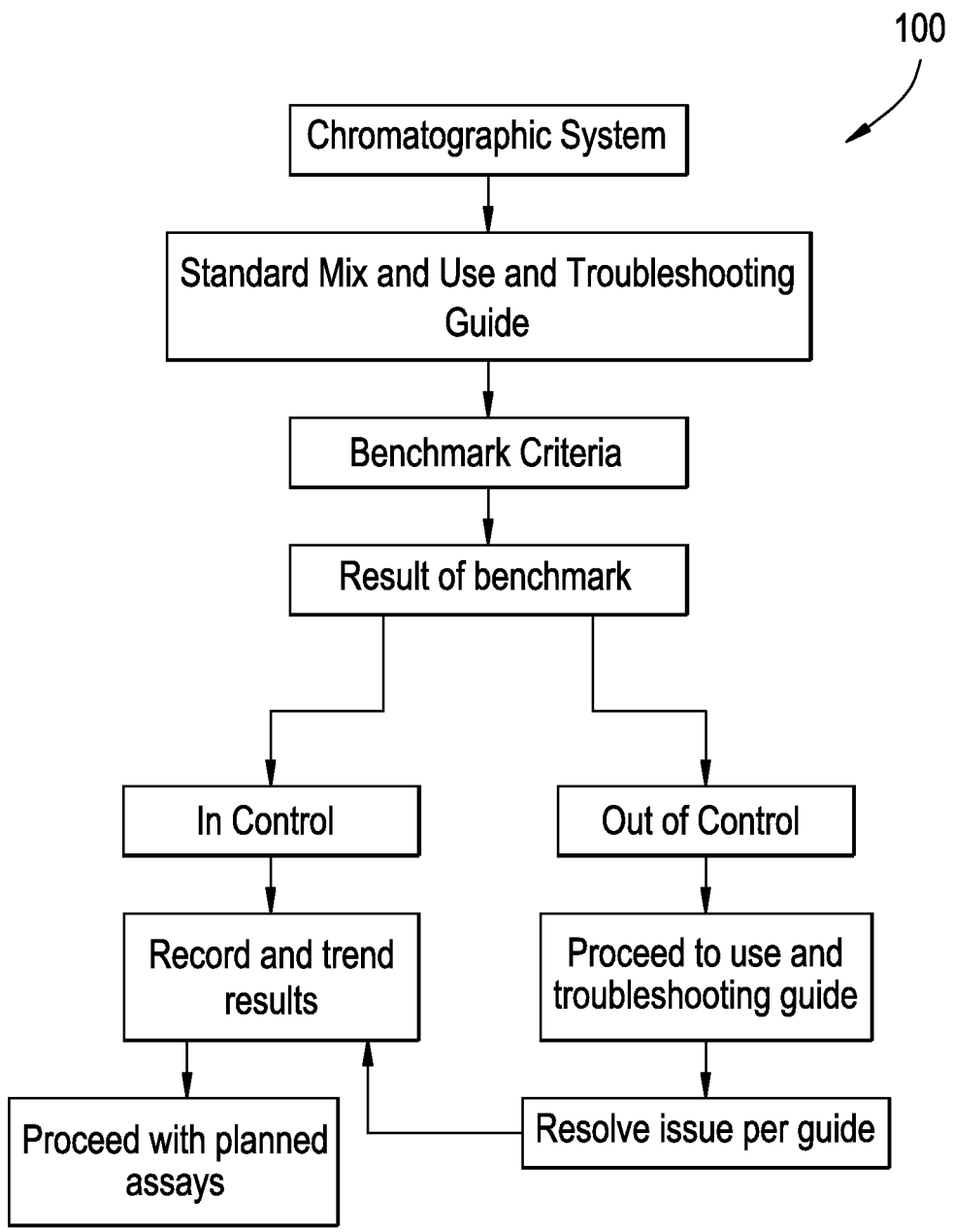

| Analysis | Peak Retention Time (mins) |
|---|---|
| 1 | 7.10 |
| 2 | 7.11 |
| 3 | 7.12 |
| 4 | 7.09 |
| 5 | 7.08 |
| 6 | 7.10 |
| 7 | 7.11 |
| 8 | 7.13 |
| 9 | 7.10 |
| 10 | 7.11 |

| | |
|---|---|
| Mean | 7.11 |
| Standard Deviation | 0.0136 |
| LCL | 7.08 |
| UCL | 7.13 |

Retention Time Control Chart $V_{tot}$ = elution volume to peak apex $W_{tot}$ = peak width (4 sigma)

$N_{tot}$ = total plates (4 sigma)

FIG. 10C

System A $$N_{tot} = 16 \left(\frac{V_{tot}}{W_{tot}}\right)^2$$

$$N_{tot} = 16 \left(\frac{3.19ml}{0.176ml}\right)^2$$

N = 5,256 p/50 mm column
High Efficiency

System C $$N_{tot} = 16 \left(\frac{V_{tot}}{W_{tot}}\right)^2$$

$$N_{tot} = 16 \left(\frac{3.25ml}{0.200ml}\right)^2$$

N = 4225 p/50 mm column
Low Efficiency

FIG. 10D $$N_{col} = 16 \left(\frac{V_{col}}{W_{col}}\right)^2$$

$$V_{tot} = V_{col} + V_{nc}$$

$$W^2_{tot} = W^2_{col} + W^2_{nc}$$

$N_{col}$ = Efficiency of the column alone
$T_{tot}$ = total volume of the system from injector through detector cell
$V_{col}$ = void volume of the column
$V_{nc}$ = non column volume of the system (system volume)
peak width = bandspread
$W_{tot}$ = bandspread of the entire system with column
$W_{col}$ = portion of the bandspread from the column
$W_{nc}$ = portion of the bandspread from the system without a column

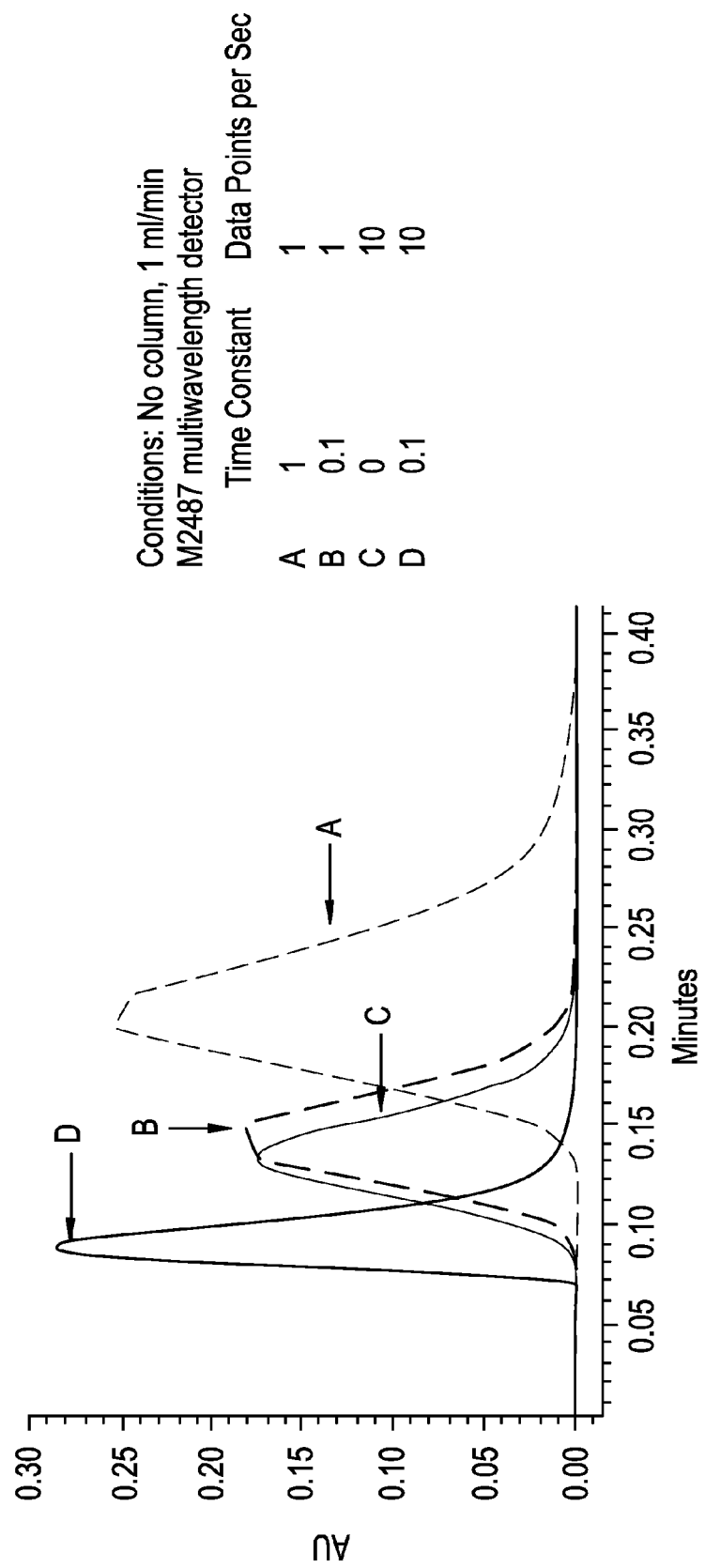

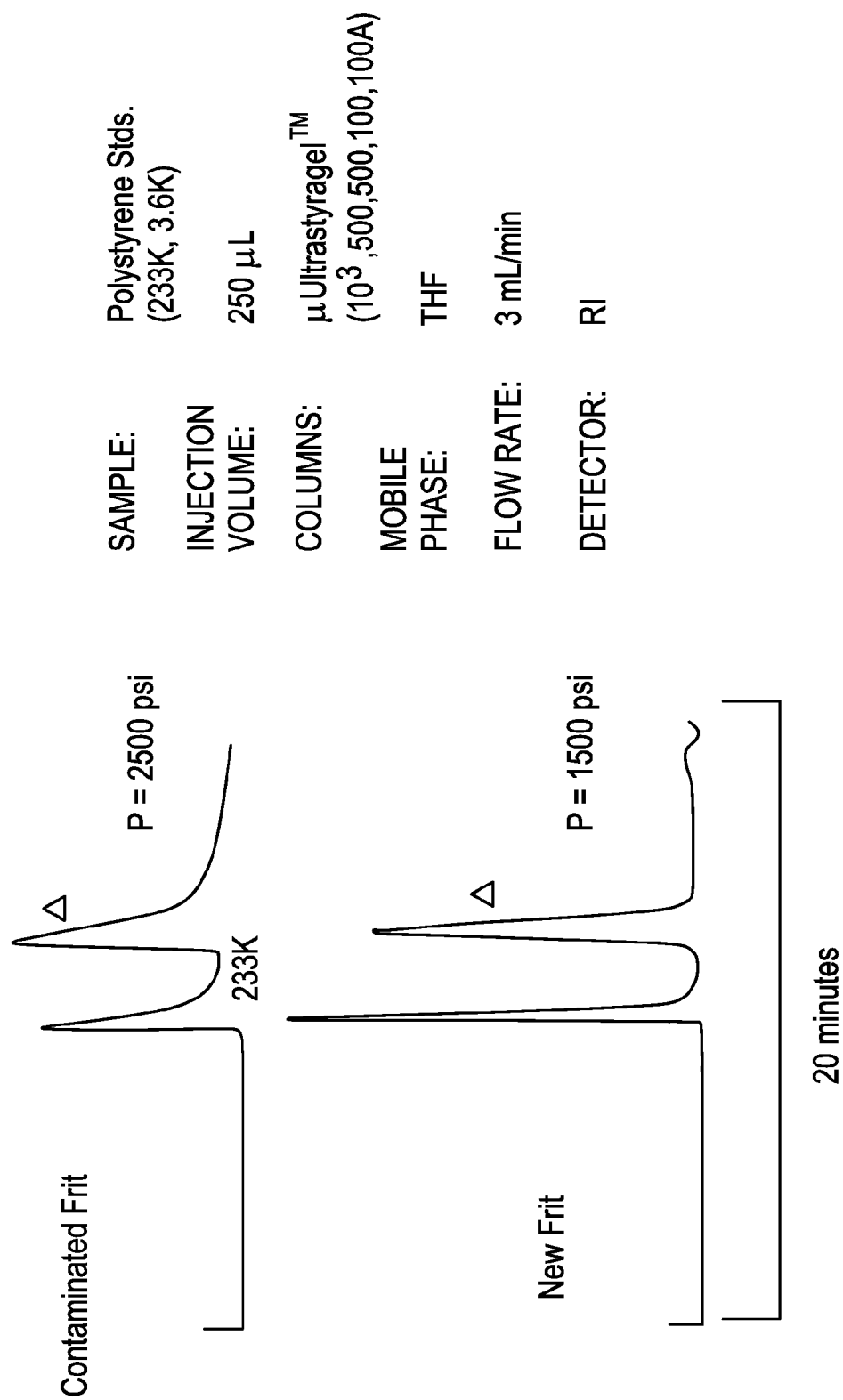

| Injector to Column | Column to Detector | Detector Cell Type | Band-spread μL | Change to System Volume μL |
|---|---|---|---|---|
| 30" x 0.009" | 18" x 0.009" | WATERS 2487 | 56 | 0 |
| 30" x 0.009" | 18" x 0.020" | WATERS 2487 | 112 | +92 |
| 30" x 0.009" | 18" x 0.009" | WATERS 2996 | 33 | -6 |
| 10" x 0.009" | 18" x 0.009" | WATERS 2996 | 29 | -26 |
| 10" x 0.009" | 18" x 0.005" | WATERS 2996 | 23 | -44 |
| 10" x 0.009" | 18" x 0.005" | WATERS 2996 microbore | 21 | -49 |

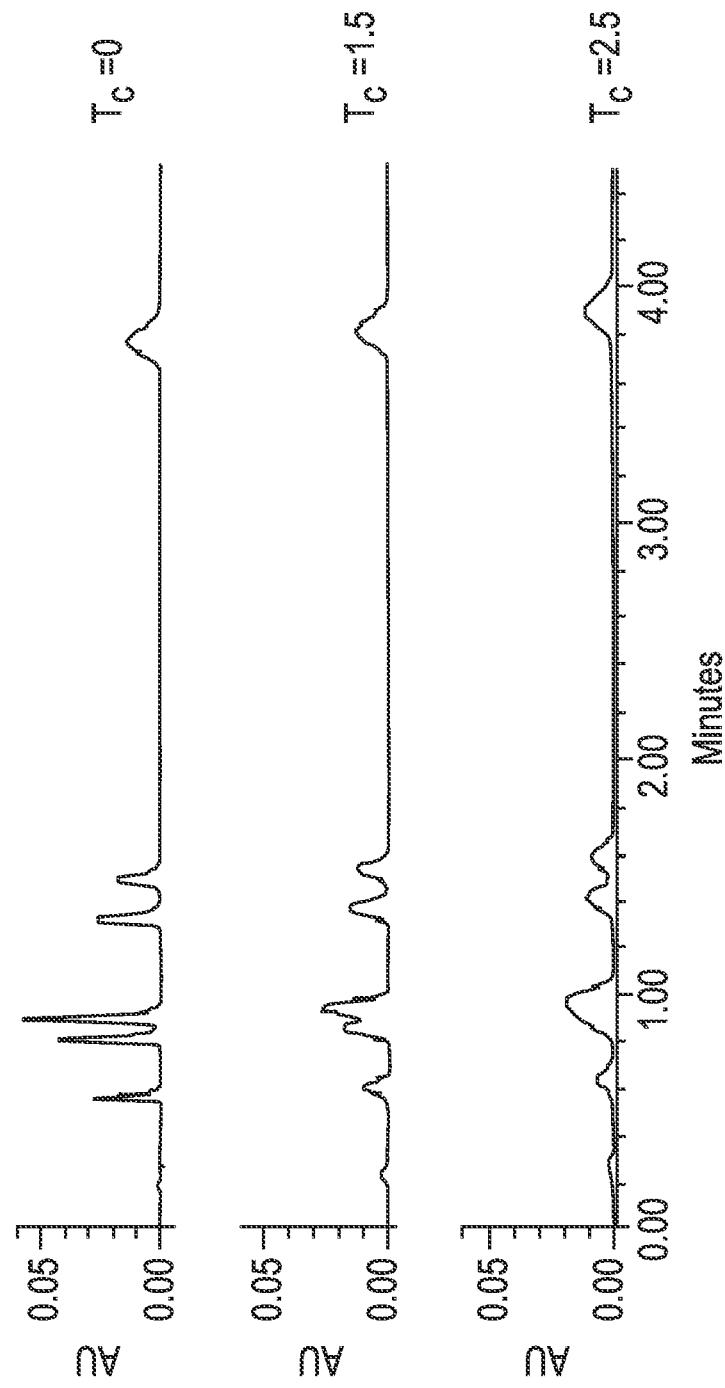

Aspirin Separation

1 Caffeine
2 Aspartame
3 Benzoic Acid
4 Sorbic Acid

1. Acetone (V$_0$)  2. Naphthalene  3. Acenaphthene

1. Uracil
2. Propranolol
3. Butylparaben
4. Dipropylphthalate
5. Naphthalene
6. Acenaphthene
7. Amitriptyline FIG. 22A
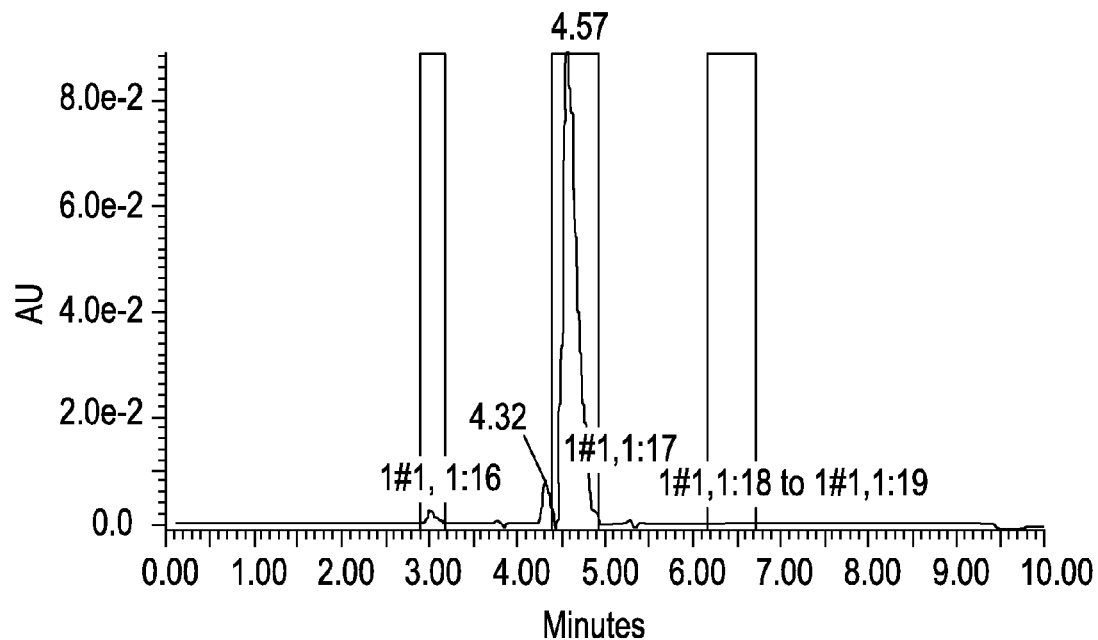
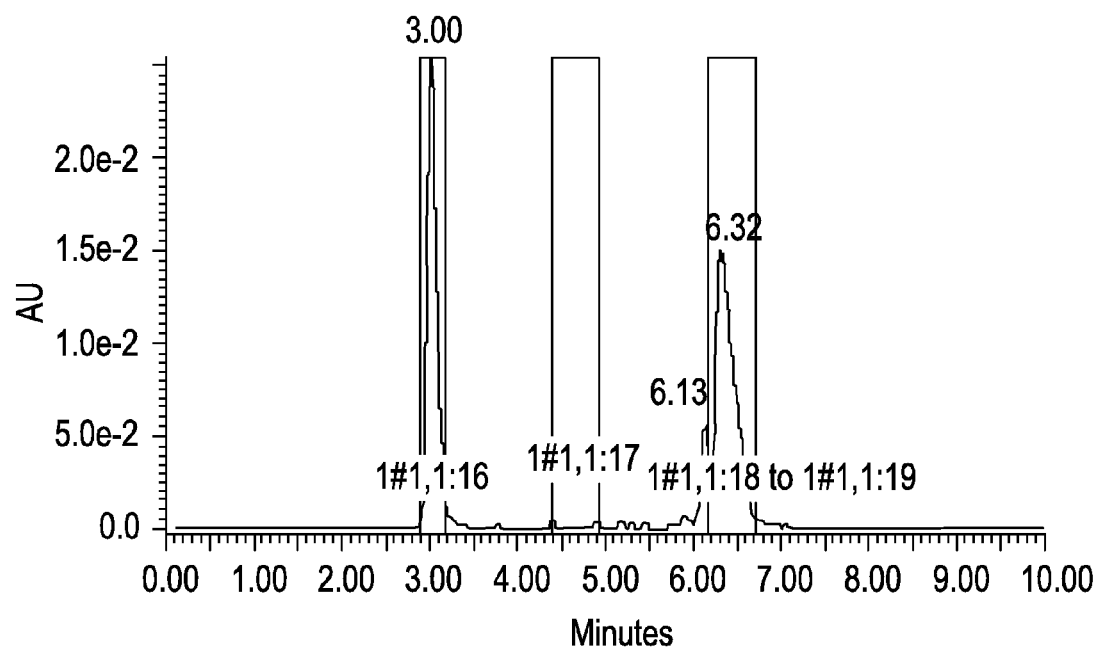

FIG. 23
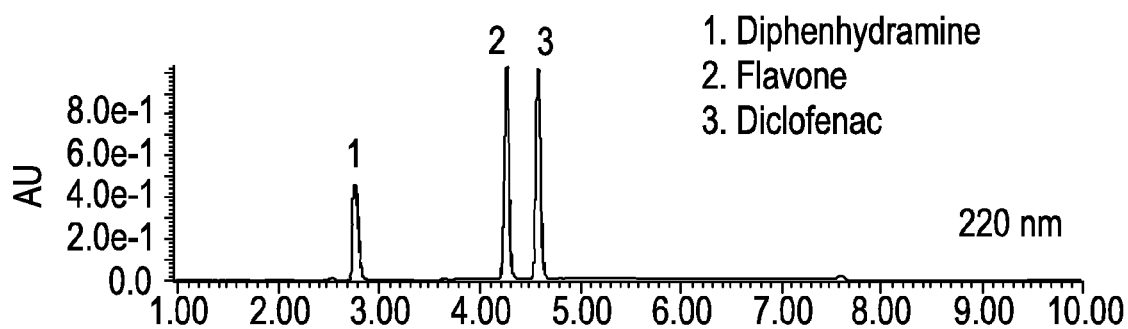
1. Diphenhydramine
2. Flavone
3. Diclofenac
220 nm
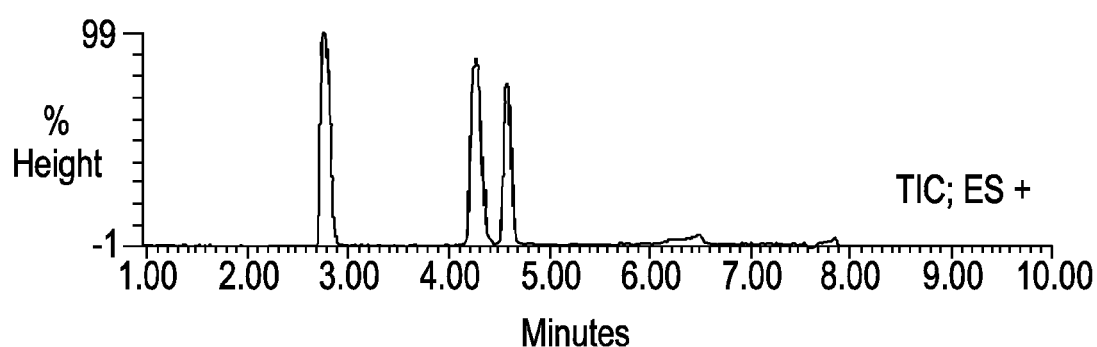
TIC; ES +
Minutes
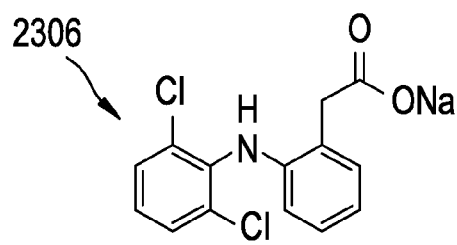
Diclofenac sodium salt
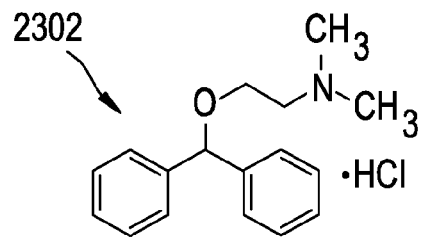
Diphenhydramine hydrochloride
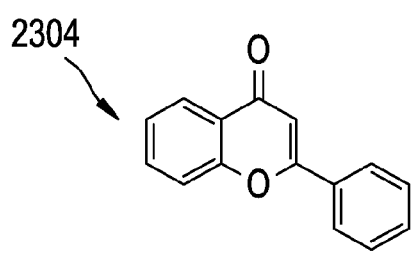
Flavone

|  |  | Acetone | Naphthalene | Acenaphthene |
|---|---|---|---|---|
| Benchmarking Data (n=45) | Retention Time Average (min) | 0.323 | 1.633 | 2.893 |
| | Retention Time %RSD | 0.690 | 0.440 | 0.440 |
| | USP Tailing Factor | 1.180 | 1.130 | 1.080 |
| | USP Plate Count | 3144 | 11009 | 10436 |

|  |  | Acetone | Naphthalene | Acenaphthene |
|---|---|---|---|---|
| Failing Column (Observed during problem) | Retention Time (min) | 0.319 | 1.574 | 2.770 |
|  | USP Tailing Factor | 1.290 | 1.040 | 1.010 |
|  | USP Plate Count | 1043 | 1458 | 1433 |
| Failing Column (After repairs) | Retention Time Average (min) | 0.323 | 1.631 | 2.893 |
|  | Retention Time %RSD | 0.670 | 0.460 | 0.440 |
|  | USP Tailing Factor | 1.170 | 1.130 | 1.090 |
|  | USP Plate Count | 3152 | 11001 | 10531 |

|  |  | Acetone | Naphthalene | Acenaphthene |
|---|---|---|---|---|
| Leaking Fitting at Pump Outlet (Observed during problem) | Retention Time (min) | 0.376 | 1.832 | 3.206 |
|  | USP Tailing Factor | 1.160 | 1.140 | 1.080 |
|  | USP Plate Count | 3438 | 9348 | 8516 |
| Leaking Fitting at Pump Outlet (After repairs) | Retention Time Average (min) | 0.323 | 1.631 | 2.893 |
|  | Retention Time %RSD | 0.680 | 0.450 | 0.440 |
|  | USP Tailing Factor | 1.180 | 1.120 | 1.070 |
|  | USP Plate Count | 3148 | 11020 | 10421 |

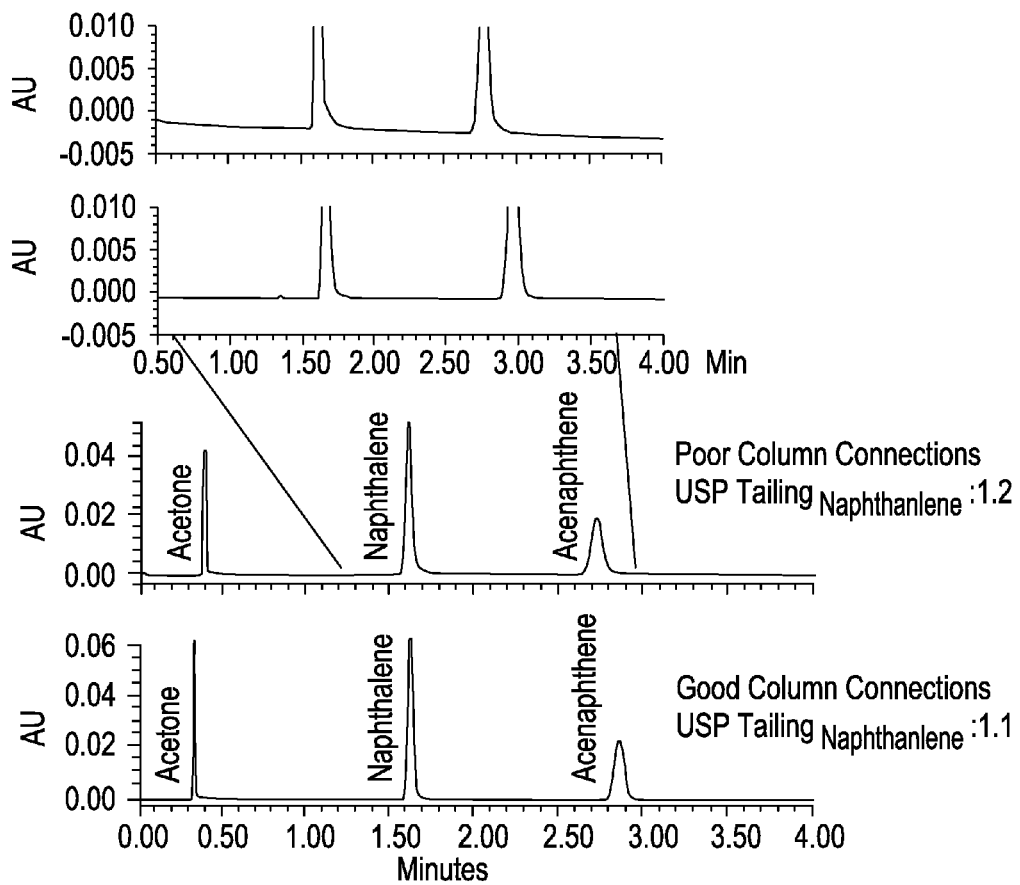

|  |  | Acetone | Naphthalene | Acenaphthene |
|---|---|---|---|---|
| Improper Seating of Column Outlet Tubing (Observed during problem) | Retention Time (min) | 0.385 | 1.669 | 2.815 |
|  | USP Tailing Factor | 1.140 | 1.200 | 1.170 |
|  | USP Plate Count | 3159 | 8685 | 8659 |
| Improper Seating of Column Outlet Tubing (After repairs) | Retention Time Average (min) | 0.323 | 1.631 | 2.893 |
|  | Retention Time %RSD | 0.670 | 0.450 | 0.440 |
|  | USP Tailing Factor | 1.160 | 1.080 | 1.070 |
|  | USP Plate Count | 3220 | 10980 | 10438 |

|  |  | Acetone | Naphthalene | Acenaphthene |
|---|---|---|---|---|
| Air Bubble in system (Observed during problem) | Retention Time (min) | 0.471 | 2.066 | 3.436 |
|  | USP Tailing Factor | 1.120 | 1.160 | 1.110 |
|  | USP Plate Count | 4408 | 10116 | 9616 |
| Air Bubble in system (After repairs) | Retention Time Average (min) | 0.323 | 1.631 | 2.893 |
|  | Retention Time %RSD | 0.690 | 0.460 | 0.440 |
|  | USP Tailing Factor | 1.15 | 1.06 | 1.09 |
|  | USP Plate Count | 3189 | 11202 | 10449 |

FIG. 30B

|  |  | Acetone | Naphthalene | Acenaphthene |
|---|---|---|---|---|
| 52% ACN used in separation | Retention Time (min) | 0.336 | 1.295 | 2.148 |
|  | USP Tailing Factor | 1.130 | 1.070 | 1.080 |
|  | USP Plate Count | 3290 | 9323 | 9144 |
| 48% ACN used in separation | Retention Time (min) | 0.358 | 2.035 | 3.690 |
|  | USP Tailing Factor | 1.150 | 1.080 | 1.080 |
|  | USP Plate Count | 3124 | 8818 | 8974 |
| 50% ACN (recommended conditions) used in separation | Retention Time Average (min) | 0.323 | 1.632 | 2.893 |
|  | Retention Time %RSD | 0.680 | 0.430 | 0.440 |
|  | USP Tailing Factor | 1.140 | 1.050 | 1.060 |
|  | USP Plate Count | 3297 | 11402 | 10520 |

|  | Average Retention Time (min) | %RSD Retention Time |
|---|---|---|
| Acetone | 0.323 | 0.69 |
| Naphthalene | 1.633 | 0.44 |
| Acenaphthene | 2.893 | 0.44 |

FIG. 32
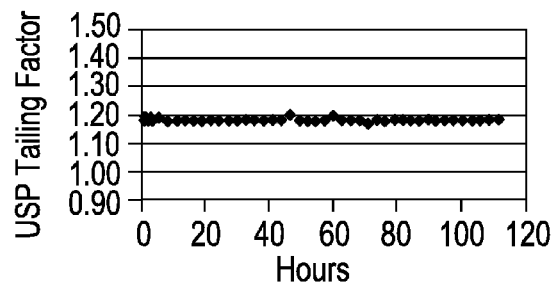
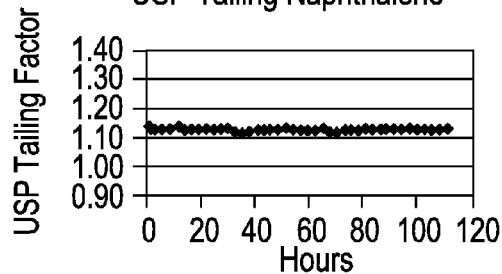
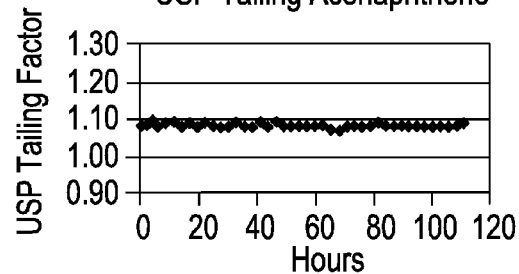
FIG. 33
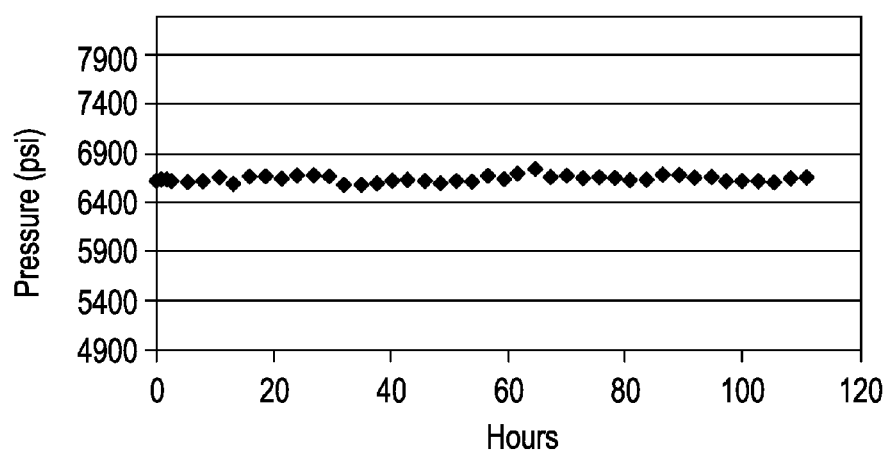

| Component | Empirical Formula | Exact Mass (as [M+H]$^+$) | Exact Mass (as [M+H]$^-$) | Concentration for analysis (μg/mL) |
|---|---|---|---|---|
| Acetaminophen | $C_8H_9NO_2$ | 152.0712 | 150.0555 | 10 |
| Caffeine | $C_8H_{10}N_4O_2$ | 195.0882 | | 1.5 |
| Sulfaguanidine | $C_7H_{10}N_4O_2S$ | 215.0603 | 213.0446 | 5 |
| Sulfadimethoxine | $C_{12}H_{14}N_4O_4S$ | 311.0814 | 309.0658 | 1 |
| Val-Tyr-Val | $C_{19}H_{29}N_3O_5$ | 380.2185 | 378.2029 | 2.5 |
| Verapamil | $C_{27}H_{38}N_2O_4$ | 455.2910 | | 0.2 |
| Terfenadine | $C_{32}H_{41}NO_2$ | 472.3216 | | 0.2 |
| Leucine-Enkephalin | $C_{28}H_{37}N_5O_7$ | 556.2771 | 554.2615 | 2.5 |
| Reserpine | $C_{33}H_{40}N_2O_9$ | 609.2812 | | 0.6 |

FIG. 35A

| Day | Injection | Acetone | Naphthalene | Acenaphthene |
|---|---|---|---|---|
| | | Retention Time | | |
| day1-1 | 7 | 0.33 | 1.63 | 2.89 |
| day1-2 | 8 | 0.32 | 1.62 | 2.86 |
| day1-3 | 9 | 0.33 | 1.64 | 2.89 |
| day2-1 | 16 | 0.32 | 1.64 | 2.90 |
| day2-2 | 17 | 0.32 | 1.64 | 2.90 |
| day2-3 | 18 | 0.32 | 1.64 | 2.90 |
| day3-1 | 25 | 0.32 | 1.63 | 2.90 |
| day3-2 | 26 | 0.33 | 1.64 | 2.90 |
| day3-3 | 27 | 0.33 | 1.64 | 2.91 |
| day6-1 | 34 | 0.32 | 1.64 | 2.88 |
| day6-2 | 35 | 0.32 | 1.64 | 2.88 |
| day6-3 | 36 | 0.32 | 1.62 | 2.86 |
| day7-1 | 43 | 0.32 | 1.62 | 2.88 |
| day7-2 | 44 | 0.32 | 1.62 | 2.90 |
| day7-3 | 45 | 0.32 | 1.63 | 2.89 |

FIG. 35B

| | Acetone | Naphthalene | Acenaphthene |
|---|---|---|---|
| | Retention Time (minutes) | | |
| Mean | 0.32 | 1.63 | 2.89 |
| Standard Deviation | 0.00 | 0.01 | 0.01 |
| %RSD | 0.58 | 0.45 | 0.49 |
| LWL | 0.32 | 1.62 | 2.86 |
| UWL | 0.33 | 1.65 | 2.92 |
| LCL | 0.32 | 1.61 | 2.85 |
| UCL | 0.33 | 1.65 | 2.93 |

CHROMATOGRAPHIC SYSTEM QUALITY CONTROL REFERENCE MATERIALS

CROSS REFERENCE TO RELATED APPLICATIONS

The present application claims priority to U.S. Provisional Patent Application Ser. No. 61/678,949, filed on Aug. 2, 2012, which is hereby incorporated by reference in its entirety.

FIELD OF THE INVENTION

The present invention relates generally to methods, kits, and compositions of matter for chromatographic system quality control.

BACKGROUND OF THE INVENTION

Chromatography is a valuable tool for chemists, which has found use in clinical, academic, and industrial settings. In order to ensure accurate and reproducible results while conducting research, it is imperative that chromatographic systems are functioning properly. As chromatographic systems become more sophisticated and include more components, suitability testing of entire chromatography systems (e.g. not simply individual parts such as a column) is important to prevent inaccurate data due to uncalibrated, miscalibrated, malfunctioning, broken, or worn out components, as well as drift or improper settings. Examples of components found in a chromatography system include the column, tubing, mobile phase composition, computer hardware, software, injector, pump, in-line filter, guard column, detector, and temperature control apparatus, as well as combinations thereof. Examples of systems that these components can be used with include liquid chromatography (LC), high performance liquid chromatography (HPLC), ultra high performance liquid chromatography (UHPLC), supercritical fluid chromatography (SFC), and carbon dioxide based chromatography.

SUMMARY OF THE INVENTION

The invention provides methods for quality control testing of chromatographic systems (e.g. assessing system performance and benchmarking chromatographic specifications for the entire system), as well as compositions for use in carrying out such tests and instructional guidelines for use and troubleshooting system issues based on the results. Suitability or quality control can be used to measure whether or not a chromatographic system is in control (e.g. functioning according to desired parameters, for example quality control parameters). For example, the invention provides for a number of standard reference solutions (e.g. quality control reference material ("QCRM"), or in some cases referred to as suitability standards) that are pre-calibrated to contain precise concentrations of analytes, and designed to maintain their integrity over time. For example, when stored properly, the composition of the reference solutions will not change appreciably over time due to factors such as evaporation, oxidation, and the like.

QCRMs are not simply standard solutions for a particular analyte of interest. QCRMs need not include the analyte of interest. QCRMs can include multiple compounds, which can be used to validate, control, and/or troubleshoot a chromatographic system (i.e., not simply a column or component of the system). Use of the suitability standards can provide particular information relevant to the entire chromatographic system, such as whether the chromatographic system is suitable, or if there is a need to troubleshoot, and if so, how best to carry out the troubleshooting process. Finally, the standard components are chosen so that they are well-separated by a chromatographic system, demonstrate good peak shape in UV and MS analysis, are acceptable for use on a variety of columns, and so that their behavior and benchmark criteria change upon system changes.

Analyzing a QCRM with a chromatographic system can provide a standardized assessment of the functionality of the system over time because the suitability standard is constant over time. By analyzing the suitability standard once or multiple times, parameters such as peak width, peak area, retention time, and peak resolution can be measured. Moreover, upper control limits (UCL) and lower control limits (LCL) and average retention times for the components of the suitability standard can be calculated. This information can provide an accurate understanding of the functional status of the entire chromatography system (e.g. all components of the system, including hardware and software). If the measured parameters of a QCRM test do not match expected results, the data can be used to diagnose and troubleshoot issues affecting at least one part of the entire system. Documents and software can be included along with the QCRM standards to help troubleshooting in light of a given negative test result. Furthermore, QCRM tests applied to multiple chromatography systems within and across locations can give insight into the standard variability and suitability of multiple chromatography systems. These data can allow the comparison of the working parameters of multiple systems, even in different locations.

QCRMs can be advantageously used to remove uncertainty. For example, QCRMs can provide a quick and easy way to understand a chromatographic system's health. Uncertainty can be removed through standardized manufacturing. For example, QCRMs can be ready-to-use mixes made in an International Organization for Standardization ("ISO") accredited facility (e.g., ISO 9001.15017025 and 150 Guide 34). QCRMs can be pre-formulated for sale and purchased by a user. QCRMs can be used to trend system performance (e.g., control charting, which can provide a powerful visual enabling a user to take proactive maintenance measures) and troubleshooting (e.g., quickly resolve issues related to hardware, mobile phase, columns, and/or chemistries).

QCRMs can be advantageously used to maintain consistency and/or improve the accuracy of analytical systems and measurements through use of precisely formulated standards. For example, using a single source for QCRMs can open the doors for intra- and inter-lab comparisons, which are necessary in a global market. Standardizing performance testing can enable a user to: reduce variability (e.g., integrating certified products means less re-work, reduced paperwork, and improved data acceptance) and minimize user time spent on routine activities (e.g., no more daily mixing and formulating standards, increasing time for scientific problem solving).

QCRMs can be advantageously used to maintain system control. For example, QCRMs can range from less complex neutrals mixtures to more complex application-specific standards (e.g., reversed phase and LCMS QCRM), and can be used for an impressive number of performance tests. Compounds in QCRMs can be vigorously evaluated and chosen to provide one or more of the following advantages: compatibility for use on a variety of columns, with good peak shape in UV and MS; ability to assess hardware, software, mobile phase, and/or column and chemistry issues; compatibility with a wide variety of systems and methods.

QCRMs can be advantageously used to simplify and reproducibly manage the accuracy of chromatographic results, leading to increased productivity by reducing repeat runs and/or improved compliance across different (e.g., global) sites.

The invention provides method for chromatographic analysis comprising: obtaining a chromatogram from a reference material using a chromatographic system, wherein the reference material comprises a standardized formulation of two or more compounds that can be used for benchmarking and troubleshooting the chromatographic system; evaluating a difference between the chromatogram and a benchmark for the reference material on the chromatography system; and
(i) analyzing a sample potentially comprising an analyte of interest, wherein the analyte of interest does not comprise any of the two or more compounds of the standardized formulation, or compounds substantially similar thereto, if the difference between the chromatogram and the benchmark is within a predetermined tolerance, or (ii) troubleshooting the chromatography system using the chromatogram if the difference between the chromatogram and the benchmark is not within the predetermined tolerance.

In certain embodiments of the invention, the standardized formulation of two or more compounds comprises acetone, naphthalene, and acenaphthene. In certain embodiments of the invention, the analyte of interest comprises a neutral compound.

In certain embodiments of the invention, the standardized formulation of two or more compounds comprises amitriptyline, acenaphthene, naphthalene, dipropyl phthalate, butyl paraben, propranolol, and uracil. In certain embodiments of the invention, the chromatographic system comprises a reversed phase stationary phase.

In certain embodiments of the invention, the standardized formulation of two or more compounds comprises acetaminophen, caffeine, sulfaguanidine, sulfadimethoxine, Val-Tyr-Val, zerapamil, terenadine, leucine-enkephalin, and reserpine. In certain embodiments of the invention, the chromatographic system comprises a liquid chromatography-mass spectroscopy ("LC-MS") system.

In certain embodiments of the invention, the standardized formulation of two or more compounds comprises diphenhydramine, flavone, and diclofenac. In certain embodiments of the invention, the chromatographic system comprises a preparative chromatography system.

In certain embodiments of the invention, the chromatography system comprises a liquid chromatography ("LC"), high performance liquid chromatography ("HPLC"), ultra high performance liquid chromatography ("UHPLC"), supercritical fluid chromatography ("SFC"), or carbon dioxide-based chromatography system. In certain embodiments of the invention, the protocol for obtaining the chromatogram from the reference material is different from the protocol for analyzing the sample. In certain embodiments of the invention, the system has been calibrated using a calibrator that is different than the reference material.

In certain embodiments of the invention, the predetermined tolerance is about three standard deviations.

The invention also provides chromatographic system quality control reference materials (QCRM) comprising: a standardized formulation having a predetermined concentration of acetone, a predetermined concentration of naphthalene, and a predetermined concentration of acenaphthene, wherein the standardized formulation is adapted for benchmarking and troubleshooting a chromatographic system in the analysis of a sample potentially comprising an analyte of interest, and wherein the analyte of interest does not comprise any acetone, napthaline, acenaphthene, or compounds substantially similar thereto.

In certain embodiments of the QCRM of the invention, the predetermined concentration of acetone is about 10 μL/mL; the predetermined concentration of naphthalene is about 25 μg/mL; and the predetermined concentration of acenaphthene is about 0.40 μg/mL.

The invention also provides chromatographic system quality control reference material comprising: a standardized formulation having a predetermined concentration of amitriptyline, a predetermined concentration of acenaphthene, a predetermined concentration of naphthalene, a predetermined concentration of dipropyl phthalate, a predetermined concentration of butyl paraben, a predetermined concentration of propranolol, and a predetermined concentration of uracil, wherein the standardized formulation is adapted for benchmarking and troubleshooting a chromatographic system in the analysis of a sample potentially comprising an analyte of interest, wherein the analyte of interest does not comprise any amitriptyline, acenaphthene, naphthalene, dipropyl phthalate, butyl paraben, propranolol, uracil, or compounds substantially similar thereto.

In certain embodiments of the QCRM of the invention, the predetermined concentration of amitriptyline is about 100 μg/mL; the predetermined concentration of acenaphthene is about 200 μg/mL; the predetermined concentration of naphthalene is about 60 μg/mL; the predetermined concentration of dipropyl phthalate is about 340 μg/mL; the predetermined concentration of butyl paraben is about 20 μg/mL; the predetermined concentration of propranolol is about 400 μg/mL; and the predetermined concentration of uracil is about 16 μg/ml.

The invention further provides chromatographic system quality control reference material comprising: a standardized formulation having a predetermined concentration of acetaminophen, a predetermined concentration of caffeine, a predetermined concentration of sulfaguanidine, a predetermined concentration of sulfadimethoxine, a predetermined concentration of Val-Tyr-Val, a predetermined concentration of zerapamil, a predetermined concentration of terenadine, a predetermined concentration of leucine-enkephalin, and a predetermined concentration of reserpine, wherein the standardized formulation is adapted for benchmarking and troubleshooting a chromatographic system in the analysis of a sample potentially comprising an analyte of interest, wherein the analyte of interest does not comprise any acetaminophen, caffeine, sulfaguanidine, sulfadimethoxine, Val-Tyr-Val, zerapamil, terenadine, leucine-enkephalin, reserpine, or compounds substantially similar thereto.

In certain embodiments of the QCRM of the invention, the predetermined concentration of acetaminophen is about 10 μg/mL; the predetermined concentration of caffeine is about 1.5 μg/mL; the predetermined concentration of sulfaguanidine is about 5 μg/mL; the predetermined concentration of sulfadimethoxine is about 1 μg/mL; the predetermined concentration of Val-Tyr-Val is about 2.5 μg/mL; the predetermined concentration of zerapamil is about 0.2 μg/mL; the predetermined concentration of terenadine is about 0.2 μg/mL; the predetermined concentration of leucine-enkephalin is about 2.5 μg/mL; and the predetermined concentration of reserpine is about 0.6 μg/mL.

The invention also provides chromatographic system quality control reference material comprising: a standardized formulation having a predetermined concentration of diphenhydramine, a predetermined concentration of flavone, and a predetermined concentration of diclofenac, wherein the standardized formulation is adapted for benchmarking and troubleshooting a chromatographic system in the analysis of a sample potentially comprising an analyte of interest, wherein the analyte of interest does not comprise any diphenhydramine, flavone, diclofenac, or compounds substantially similar thereto.

In certain embodiments of the QCRM of the invention, the predetermined concentration of diphenhydramine is about 5 mg/mL; the predetermined concentration of flavone is about 5 mg/mL; and the predetermined concentration of diclofenac is about 5 mg/mL.

The invention further provides kits including the QCRM of the invention optionally further containing instructions for use.

A flow-chart representation of one embodiment of the invention is shown in flowchart 100 in FIG. 1.

As shown in FIG. 1, the invention provides for analyzing and using a standard mix and troubleshooting guide to benchmark a chromatographic system. Based on the result of the benchmark, a chromatography system is either identified as being in control or out of control. If the chromatography system is in control, the results of the benchmark analysis are recorded and trended, and planned assays may be carried out. If the chromatography system is found to be out of control, the use and troubleshooting guide is consulted to resolve the issue. Once the issue is resolved, the results of the benchmark analysis are recorded and trended, and planned assays may be carried out.

The invention can provide an all-in one solution for benchmarking a chromatography system and troubleshooting problems. The invention provides new compositions and methods for compilation of information to expand the ability to troubleshoot chromatographic problems. The invention provides a solution to the uncertainty of a chromatographic system's ability to perform by confirming or denying the system's capability. If the system is not capable, the invention provides troubleshooting information to resolve the issue. Instead of assessing one component of a chromatography system such as the column, the invention provides the ability to trend data and benchmark specifications across multiple entire systems at multiple sites, as well as establish system process capabilities. The invention provides for assessment of a chromatographic system's capability and resolution of issues to bring the system back in control. The invention further provides for teaching, training, and certifying users of chromatographic systems. Further advantages of the invention are confidence in results that come from use of a precisely formulated standard, which can save time and reduces repeat runs and allows confidence in results. Saving time can allow for personnel to be shifted to more complex tasks, thus increasing productivity. The invention can eliminate guesswork that comes with sourcing of multiple compounds for mix creation, and supports future growth. Finally, the invention can increase global compliance, ease globalization, and supports future growth.

In one aspect, the invention provides a chromatography standard comprising a carrier solvent and one or more organic compounds dissolved in the carrier solvent. The organic compounds are adapted to enable the standardization and/or benchmarking of a chromatographic system, as well as the troubleshooting and/or debugging of a chromatographic system.

In embodiments, the invention provides a chromatography standard comprising diclofenac sodium salt, diphenhydramine hydrochloride, flavone, and an aliquot of DMSO sufficient to dissolve the diclofenac sodium salt, the diphenhydramine hydrochloride, and the flavone. In one or more embodiments, the invention provides a chromatography standard comprising a solution of uracil, propranolol, butylparaben, dipropylphthalate, naphthalene, acenaphthene, and amitriptyline. In one or more embodiments, the invention provides a chromatography standard comprising naphthalene, acenaphthene, and aliquot of a solvent such as acetonitrile/water 50%/50% v/v sufficient to dissolve the naphthalene and the acenaphthene.

In another aspect, the invention provides a chromatography standardization method comprising the steps of providing to a chromatographic system a reference standard comprising a carrier solvent and one or more organic compounds dissolved in the carrier solvent, followed by measuring with the chromatography system at least one of the peak width, peak area, retention time, and peak resolution of the organic compounds, and then comparing at least one of the peak width, peak area, retention time, and peak resolution of the organic compounds to one or more expected values. Agreement with expected values within acceptable ranges from previous runs indicates that the chromatography system is in control and disagreement with the expected values, i.e., outside acceptable ranges, from previous runs indicates that the chromatography system is not in control. In one or more embodiments, the invention further provides for analyzing a sample with the chromatography system if the chromatography system is in control. In one or more embodiments, the invention further provides for troubleshooting the chromatography system if the chromatography system is not in control. In one or more embodiments, the invention further provides for trending of suitability data across multiple runs. In one or more embodiments, the invention further provides for analyzing suitability data across multiple runs. In one or more embodiments, the invention further provides for training users of the suitability standards about best practices for use of the standards.

In another aspect, the invention provides a chromatography standardization method comprising the steps of providing to a chromatographic system a reference standard comprising diclofenac sodium salt, diphenhydramine hydrochloride, flavone and an amount of DMSO sufficient to dissolve the diclofenac sodium salt, diphenhydramine hydrochloride, and flavone, followed by measuring with the chromatography system at least one of the peak width, peak area, retention time, and peak resolution of the diclofenac sodium salt, diphenhydramine hydrochloride, and flavone, and then comparing at least one of the peak width, peak area, retention time, and peak resolution of the diclofenac sodium salt, diphenhydramine hydrochloride, and flavone to a range of expected values. Agreement with expected values indicates that the chromatography system is in control and disagreement with the expected values indicates that the chromatography system is not in control. In one or more embodiments, the invention further provides for analyzing a sample with the chromatography system if the chromatography system is in control. In one or more embodiments, the invention further provides for troubleshooting the chromatography system if the chromatography system is not in control. In one or more embodiments, the invention further provides for trending of suitability data across multiple runs. In one or more embodiments, the invention further provides for analyzing suitability data across multiple runs. In one or more embodiments, the invention further provides for training users of the suitability standards about best practices for use of the standards.

In another aspect, the invention provides a chromatography standardization method comprising the steps of providing to a chromatographic system a reference standard comprising uracil, propranolol, butylparaben, dipropylphthalate, naphthalene, acenaphthene, and amitriptyline, followed by measuring with the chromatography system at least one of the peak width, peak area, retention time, and peak resolution of the uracil, propranolol, butylparaben, dipropylphthalate, naphthalene, acenaphthene, and amitriptyline, and then comparing at least one of the peak width, peak area, retention time, and peak resolution of the uracil, propranolol, butylparaben, dipropylphthalate, naphthalene, acenaphthene, and amitriptyline to a range of expected values. Agreement with expected values indicates that the chromatography system is in control and disagreement with the expected values indicates that the chromatography system is not in control. In one or more embodiments, the invention further provides for analyzing a sample with the chromatography system if the chromatography system is in control. In one or more embodiments, the invention further provides for troubleshooting the chromatography system if the chromatography system is not in control. In one or more embodiments, the invention further provides for trending of QCRM data across multiple runs. In one or more embodiments, the invention further provides for analyzing QCRM data across multiple runs. In one or more embodiments, the invention further provides for training users of the QCRM standards about best practices for use of the standards.

In another aspect, the invention provides a chromatography standardization method comprising the steps of providing to a chromatographic system a reference standard comprising naphthalene, acenaphthene and an amount of acetone to serve as a void marker, wherein the naphthalene, acenaphthene, and acetone are dissolved in the 50:50 water:acetonitrile, followed by measuring with the chromatography system at least one of the peak width, peak area, retention time, and peak resolution of the naphthalene and acenaphthene, and then comparing at least one of the peak width, peak area, retention time, and peak resolution of the naphthalene and acenaphthene to a range of expected values. Agreement with expected values indicates that the chromatography system is in control and disagreement with the expected values indicates that the chromatography system is not in control.

In one or more embodiments, the invention further provides analyzing a sample with the chromatography system if the chromatography system is in control. In one or more embodiments, the invention further provides for troubleshooting the chromatography system if the chromatography system is not in control. In one or more embodiments, the invention further provides for trending of suitability data across multiple runs. In one or more embodiments, the invention further provides for analyzing suitability data across multiple runs. In one or more embodiments, the invention further provides for training users of the QCRM standards about best practices for use of the standards.

In another aspect, the invention provides a kit for assessing the control of a chromatographic system (i.e., for determining if the system is in control or not in control. The kit comprises an organic carrier solvent and one or more organic compounds dissolved in the carrier solvent, wherein the organic compounds demonstrate predictable behavior under chromatographic separation, and instructions for (i) obtaining a chromatographic signal from the organic solvent and dissolved organic compounds, (ii) trending the chromatographic signal data across multiple runs, and (iii) comparing at least one of the peak width, peak area, retention time, and peak resolution of the organic compounds to a range of expected values, wherein agreement with expected values indicates that the chromatography system is in control and disagreement with the expected values indicates that the chromatography system is not in control. In one or more embodiments, the invention provides for analyzing a sample with the chromatography system if the chromatography system is in control. In one or more embodiments, the invention provides for troubleshooting the chromatography system if the chromatography system is not in control. In one or more embodiments, the organic solvent comprises DMSO and the organic compounds comprise diclofenac sodium salt, diphenhydramine hydrochloride, and flavone. In one or more embodiments, the organic compounds comprise uracil, propranolol, butylparaben, dipropylphthalate, naphthalene, acenaphthene, and amitriptyline. In one or more embodiments, the standard is comprised of acetone, naphthalene, acenaphthene, and an aliquot of acetonitrile/water 50%/50% v/v sufficient to dissolve the naphthalene and an acenaphthene.

Additionally, the invention can provide for a software module to analyze bulk data from multiple runs from one or more systems. The software can streamline the process of calculating UCLs, LCLs and average retention times for the components of the QCRM standard. The bulk data from multiple suitability tests can be collected on a central server. The server can store and/or analyze data from multiple sources, for example to allow for a central mediator to aid individual practitioners with troubleshooting, and/or alert practitioners of potential problems. Moreover, the invention can provide for training and certification programs to help practitioners become proficient with the process of conducting sQCRM tests on chromatographic systems.

BRIEF DESCRIPTION OF THE DRAWINGS

FIG. 1 shows a flow chart representing a method of practicing the invention.

FIGS. 10A-D show (A) chromatographs from System A, which is in control, and System C, which is not in control. The identities of the peaks are indicated; (B) shows a schematic showing the variables used for calculation of column efficiency; (C) shows calculations of column efficiency based on the peaks in the chromatographs in FIG. 10A; and (D) shows other equations that can be used to characterize systems.

10D. Exemplary calculations of bandspread without a column based on results obtained from System C in FIG. 10 are provided.

FIG. 12 shows the effect of time constant on calculated bandspreading.

FIG. 13 shows chromatographs demonstrating the effects of blocked in-line filters on column pressure and peak shape.

Figures 14A, 14B:
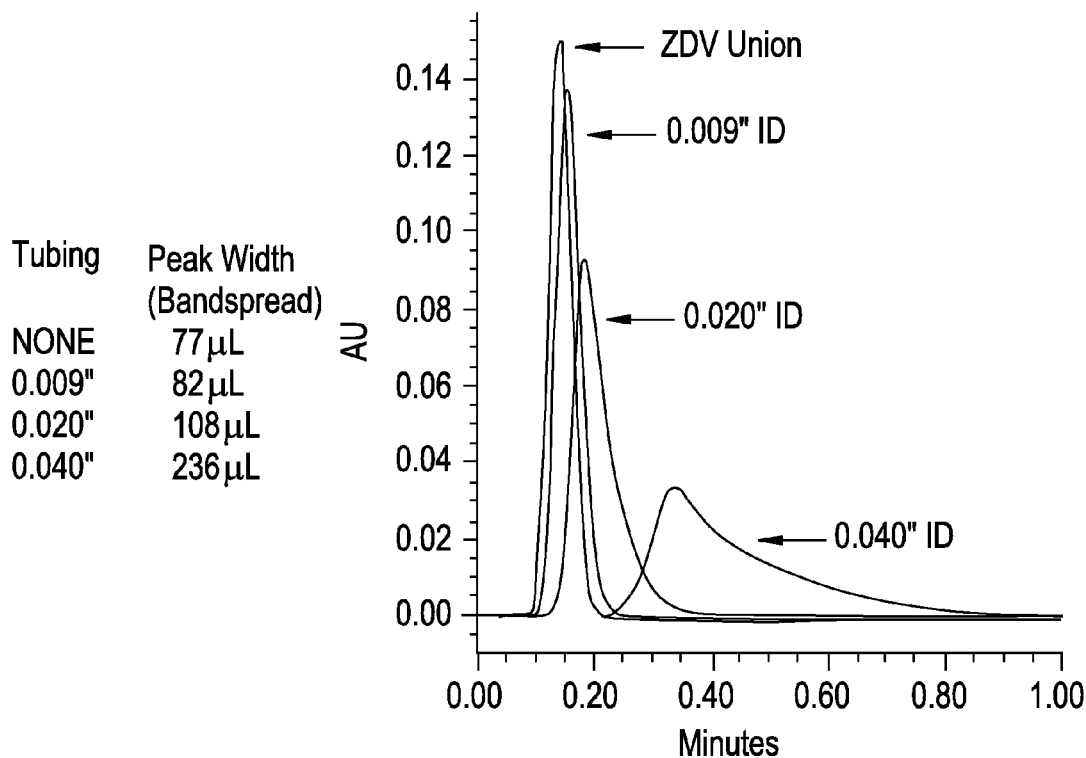

FIGS. 14A and 14B show (A) chromatographs and (B) a chart demonstrating the effects of the internal diameter of tubing on bandspread.

Figure 15:
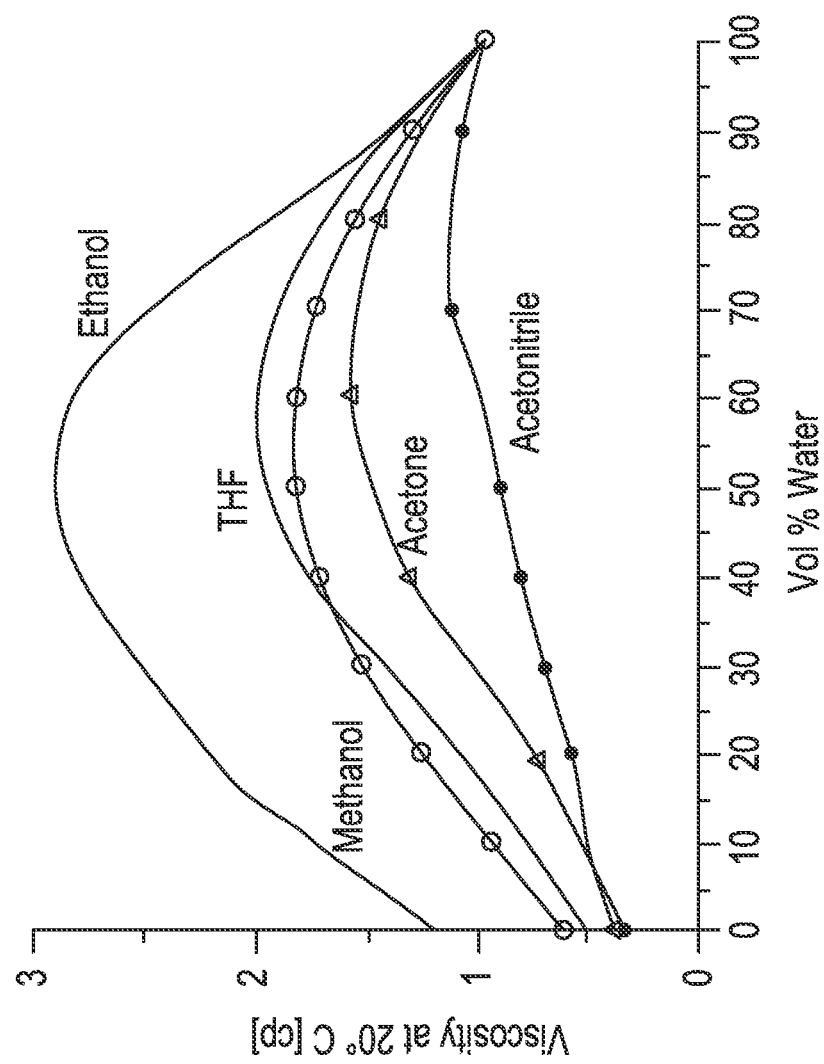

FIG. 15 shows changes in viscosity of organic solvents upon dilution with water throughout a 100% to 0% gradient.

Figure 16A:
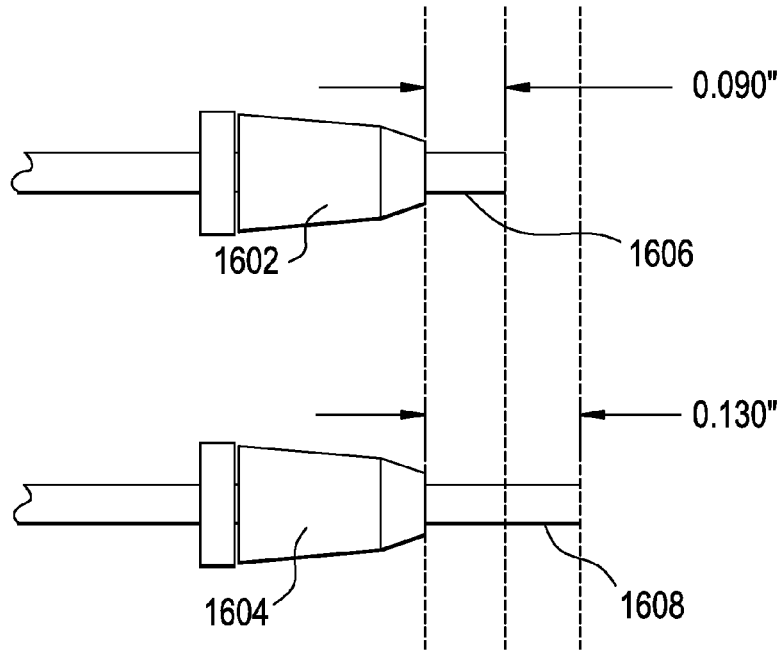
Figure 16B:
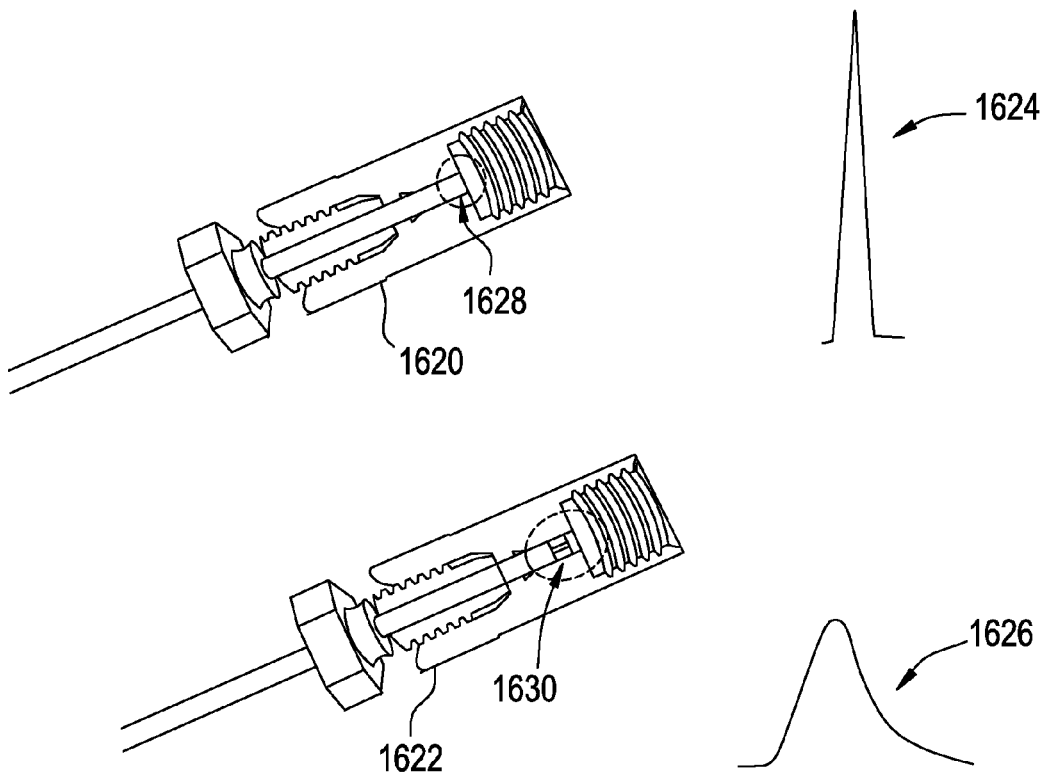

FIGS. 16A and 16B show (A) schematics and (B) photographs of different ferrule structures produced by different vendors and resulting peak shapes from use of different connectors.

Figure 17:
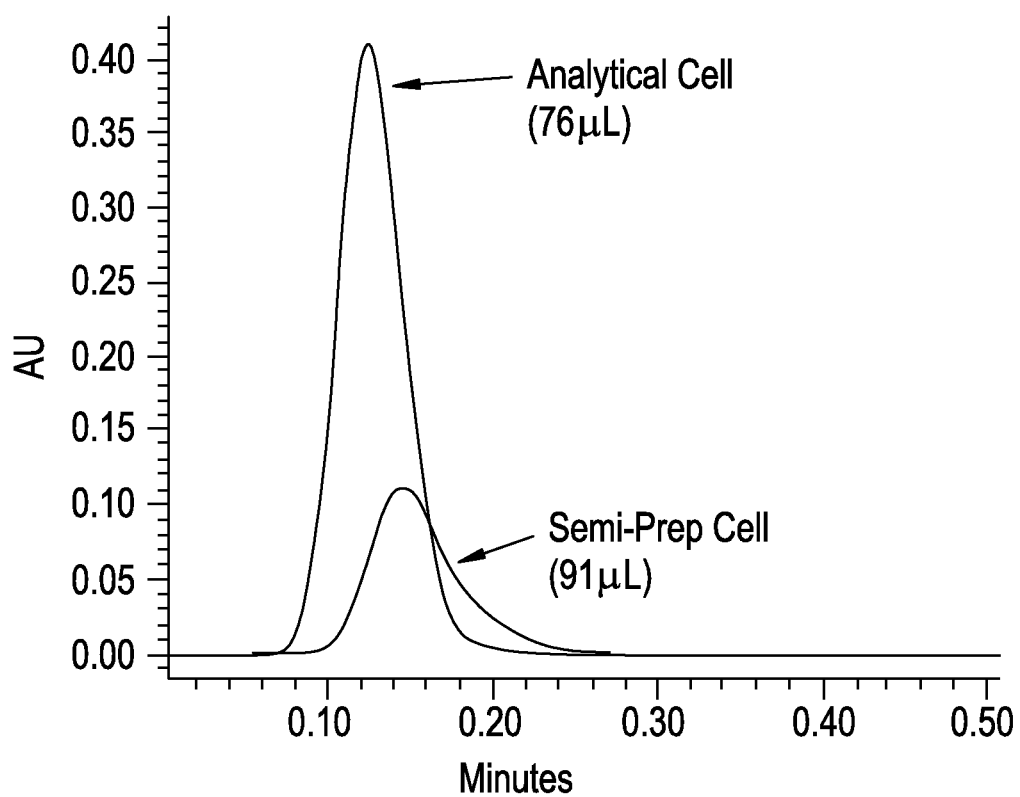

FIG. 17 shows the effects of larger internal diameter and shorter column length of a semi-preparative cell as compared to an analytical cell.

Figure 18B:
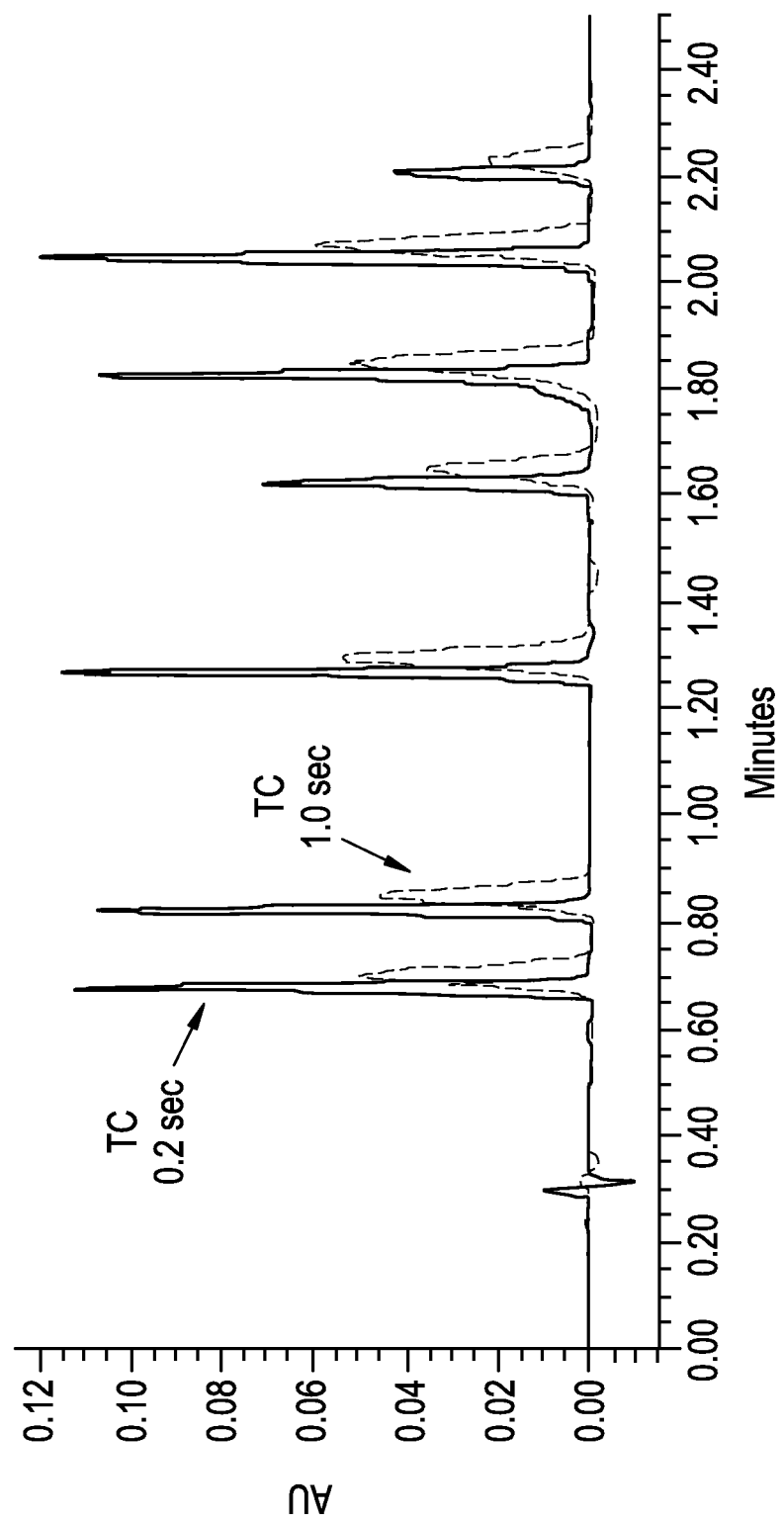

FIGS. 18A and B show (A) three chromatographs made from the same vial of sample with the same injection volume with time constants of 0, 1.5, and 2.5, as indicated, and (B) an overlay of chromatographs demonstrating the apparent retention time shift that occurs as the detector time constant is decreased from 0.2 per second to 1.0 per second.

FIGS. 19A-19E show chromatographs poor peak shape of (A) aspirin separation which can be observed when weak acids or bases are run in mobile phases that is near their pK resulting in tailing that is not a column problem which can be suggested by results as shown in (B) where a single poorly shaped peak is observed between well shaped peaks. Poorly shaped peaks (C-D) and well shaped peaks (E) for caffeine, aspartame, benzoic acid, and sorbic acid, which are used in some of the QCRM provided herein are shown.

Figure 20:
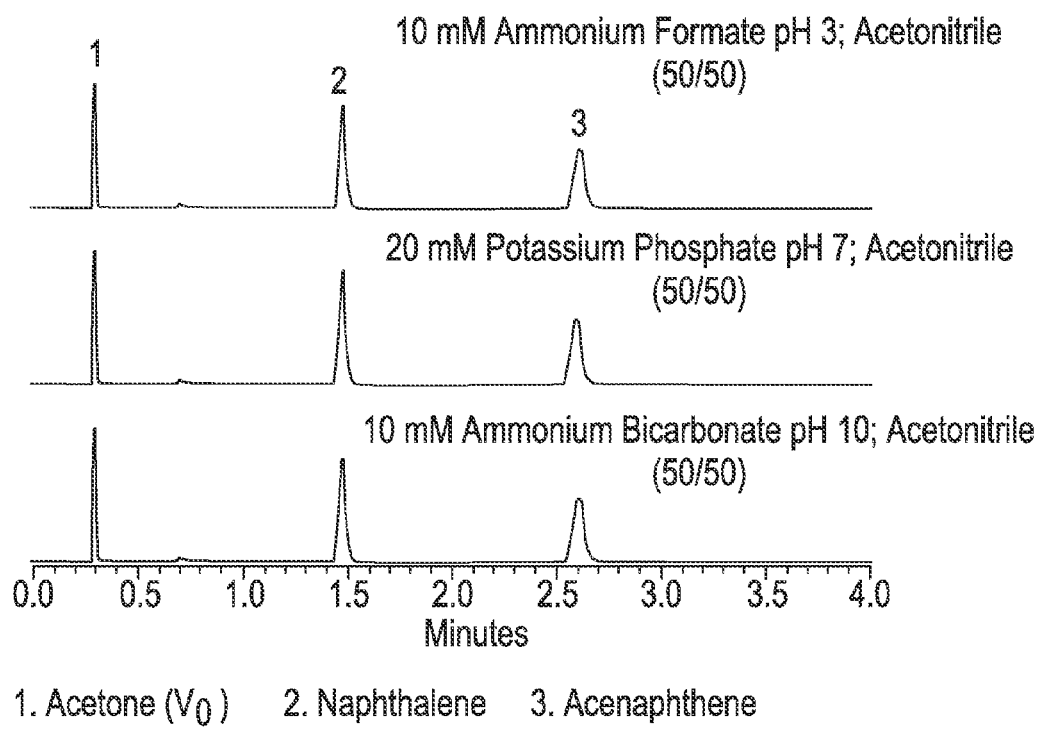

FIG. 20 shows example chromatograms obtained for the neutrals QCRM mixture via UV using an ACQUITY UPLC® BEH C18, 1.7 µm, 2.1×50 mm column (Waters Technologies Corporation, Milford, Mass.) in buffers with the indicated pH values.

Figure 21:
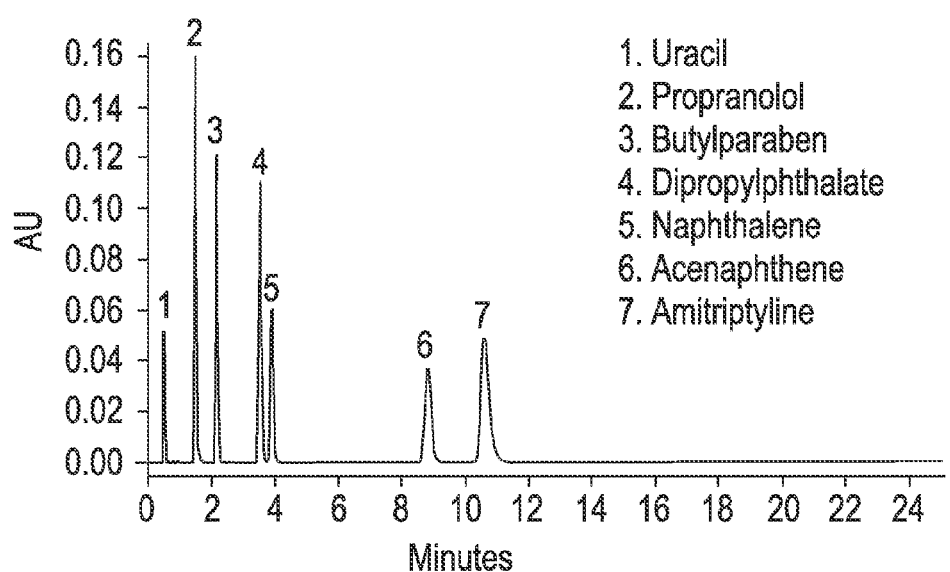

FIG. 21 shows an example chromatogram of the Reversed-Phase QCRM on an ACQUITY UPLC® HSS C18 2.1×50 mm, 1.7 µm column (Waters Technologies Corporation, Milford, Mass.), held at 30° C. The separation is isocratic using 65:35 Methanol: 20 mM phosphate buffered mobile phase at pH 7. The injection volume is 1.5 µL. The method uses a flow rate 0/0.25 mL/min and a UV detection wavelength of 254 nm.

Figure 22B:
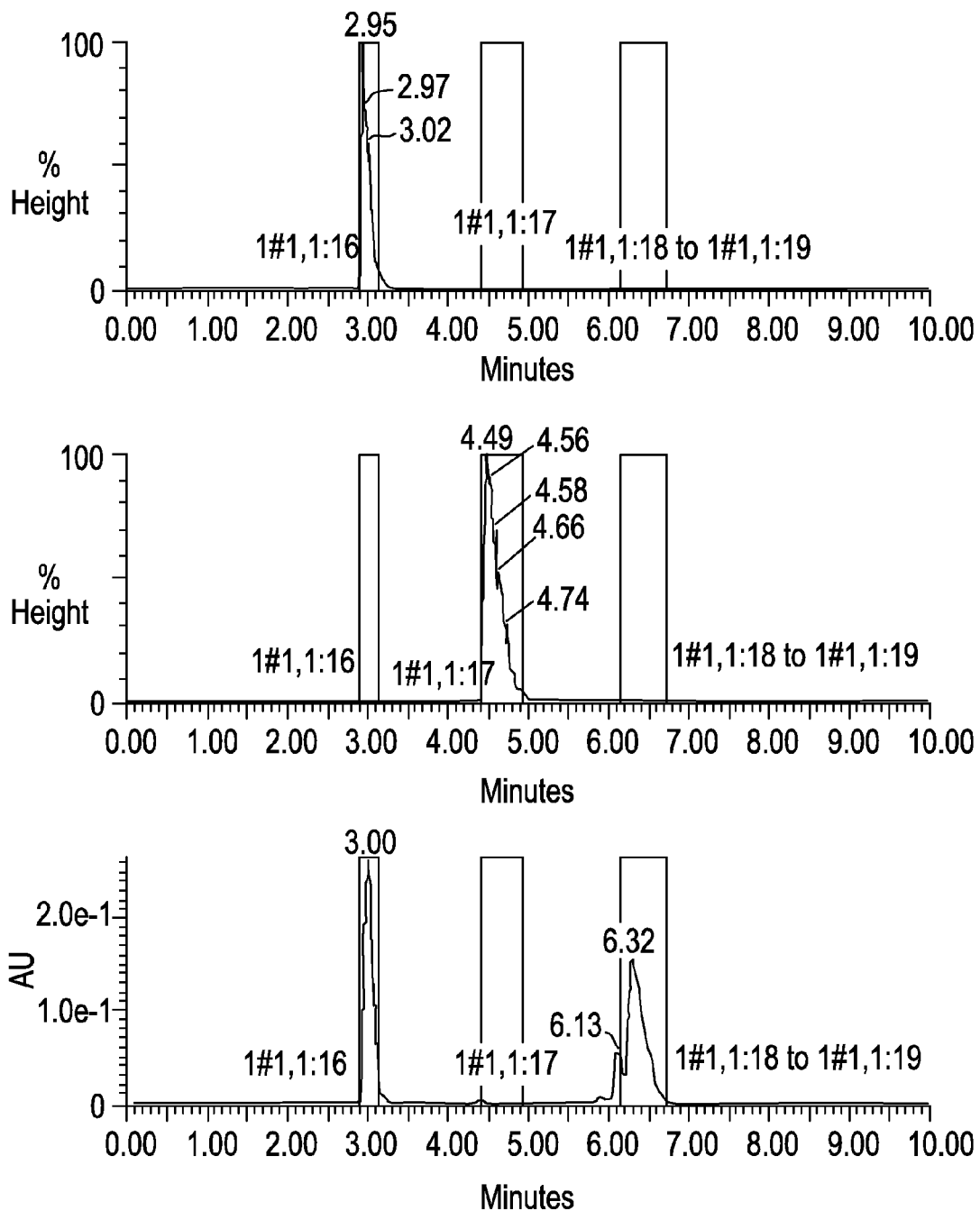

FIGS. 22A and 22B show (A) an example of the chromatograms obtained for the preparative chromatography standard via UV and MS using an XSelect® CSH™ C18, 5 µm, 19×50 mm column (Waters Technologies Corporation, Milford, Mass.) and (B) typical results of the dye test in which the three components of the dye mix have been separated and collected into separate vials labeled 1:16, 1:17 and 1:18 to 1:19.

FIG. 23 shows preparative chromatography mix of 5 mg/mL each of diclofenac sodium salt, diphenhydramine hydrochloride, and flavone in DMSO resolved by liquid chromatography and the structures of those components.

Figure 24:
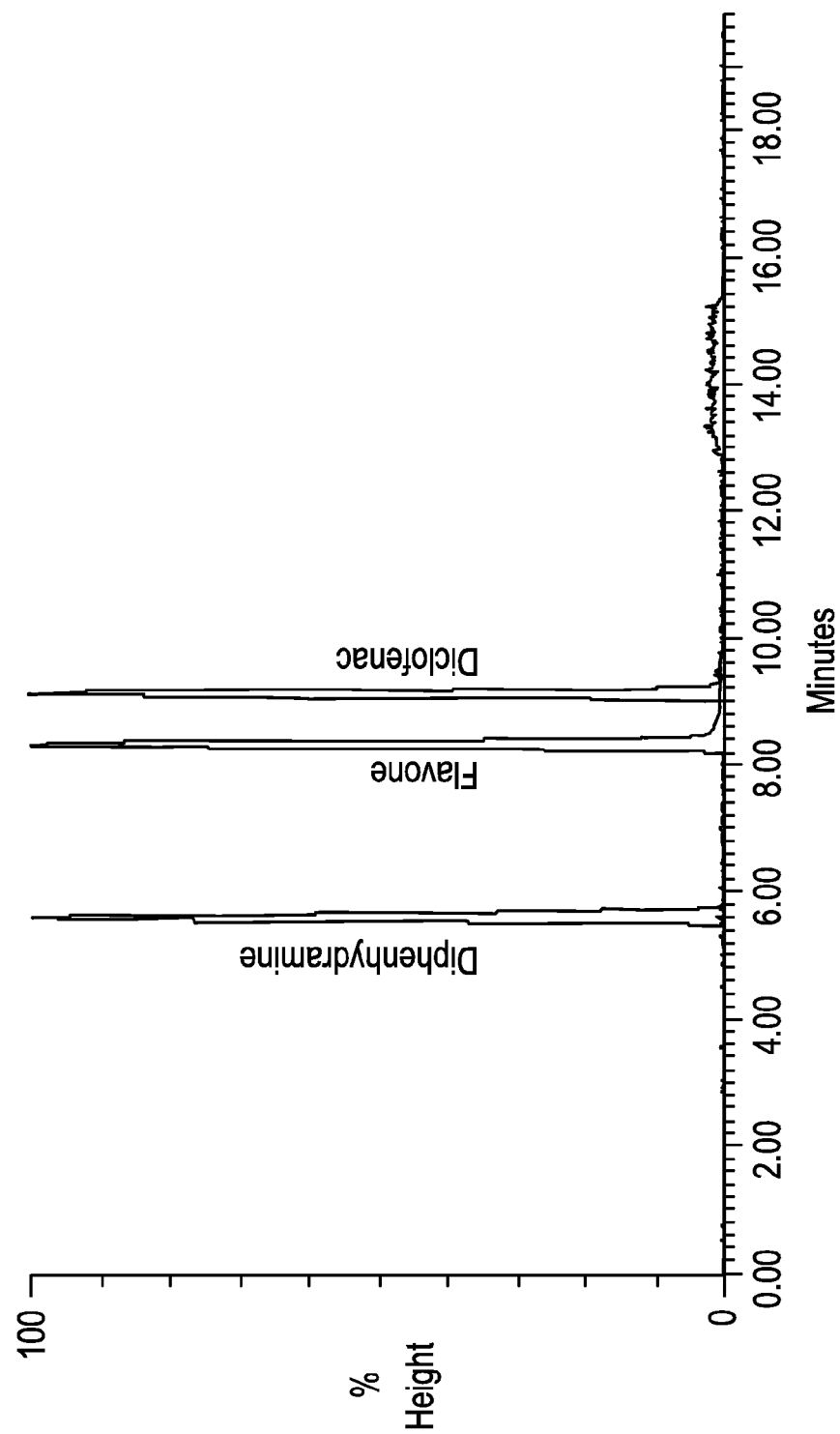

FIG. 24 an example chromatograph obtained for the preparative mix via MS when the method in the above table using a SunFire™ C18, 5 µm, 4.6×100 mm, 0.1% FA column (Waters Technologies Corporation, Milford, Mass.).

Figures 25A, 25B:
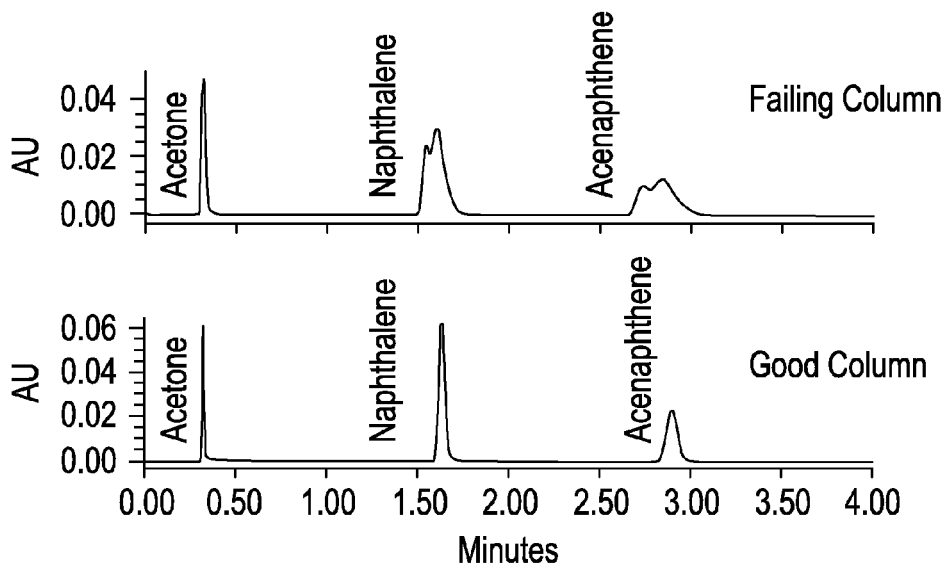
Figures 25C, 26A:
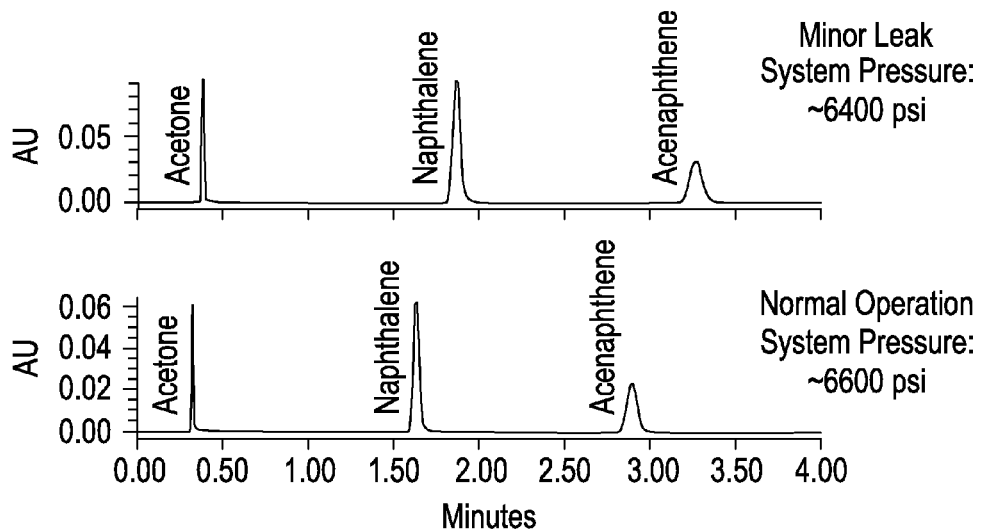

FIGS. 25A-25C show (A) data gathered during system benchmarking using the neutrals QCRM demonstrating a well operating system with a low retention time % RSD (n=45), (B) an exemplary chromatographs of separation of the neutrals QCRM on failing column and a good column, and (C) a data collected during the use of a failing column and after replacement of the column (n=9).

Figures 26B, 27A:
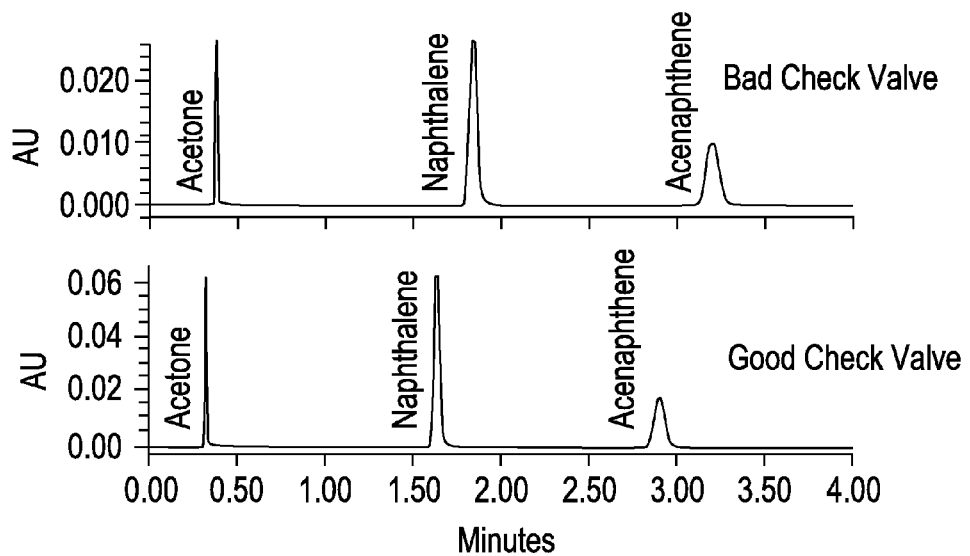

FIGS. 26A and 26B show (A) separation of the neutrals QCRM comparing a malfunctioning pump with a minor leak to a normal operating pump and (B) data collected for a malfunctioning pump with a minor leak and the repaired pump (n=9).

FIGS. 27A and 27B show (A) separation of the neutrals QCRM on a system with a bad check valve and good check valve and (B) data collected from the system with a bad check valve and a good check valve (n=9).

Figures 28B, 29A:
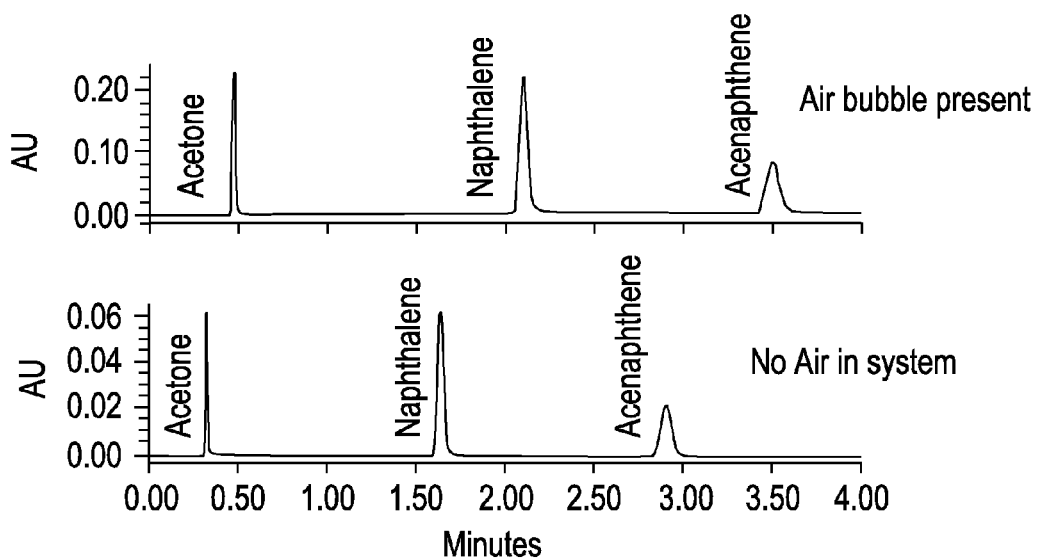

FIGS. 28A and 28B show (A) separation of the neutrals QCRM with and without proper column connections and (B) data collected with improper and proper column connections (n=9).

Figures 29B, 30A:
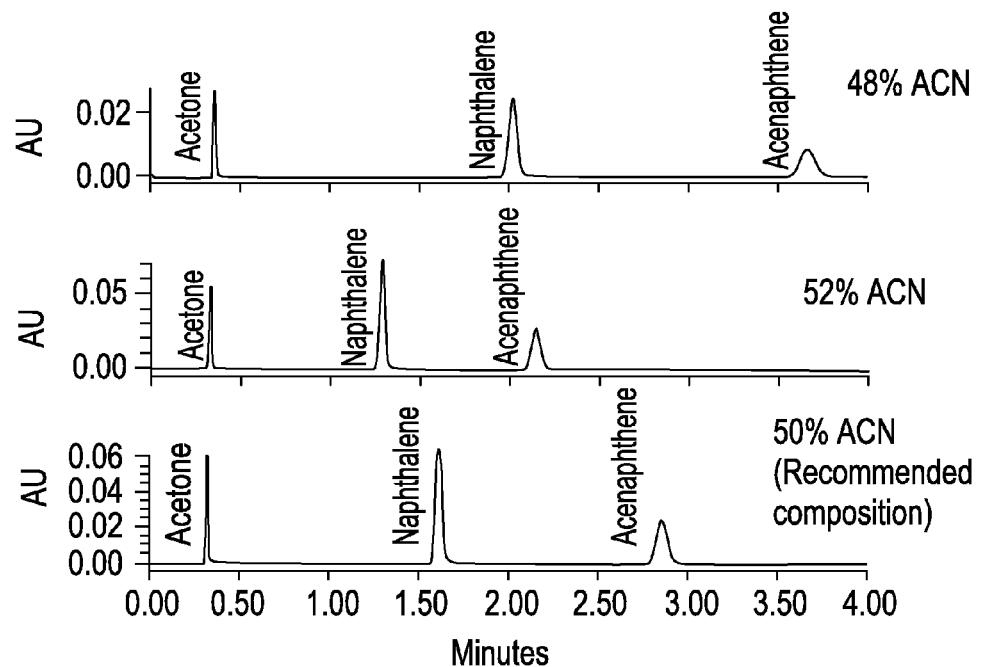

FIGS. 29A and 29B show (A) separation of the neutrals QCRM with and without an air bubble in the system and (B) data collected with and without an air bubble in the LC system. The air bubble was removed by priming the mobile phase pump.

FIGS. 30A and 30B show (A) the impact of mobile phase strength on the separation of the neutrals QCRM and (B) Data collected from the injections of neutrals QCRM with different mobile phase compositions.

Figures 31A, 31B:
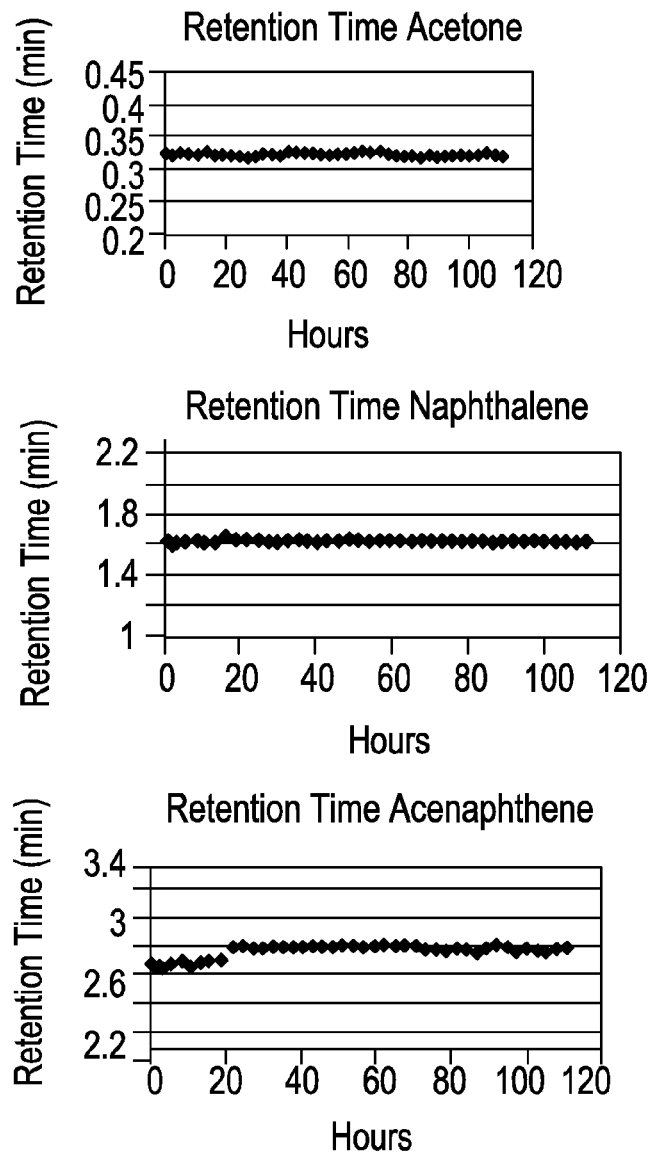

FIGS. 31A and 31B show (A) system performance benchmarking data using the neutrals QCRM, showing highly reproducible retention times demonstrated by low % RSD (n=45) over five days (120 h) and (B) shows retention time trending data for the neutrals QCRM over 5 days.

FIG. 32 shows the USP trailing factor trending data for the neutrals QCRM over 5 days (120 hours).

FIG. 33 show the system pressure trend plot of the neutrals QCRM indicating consistent pressure over time.

Figures 34A, 34B:
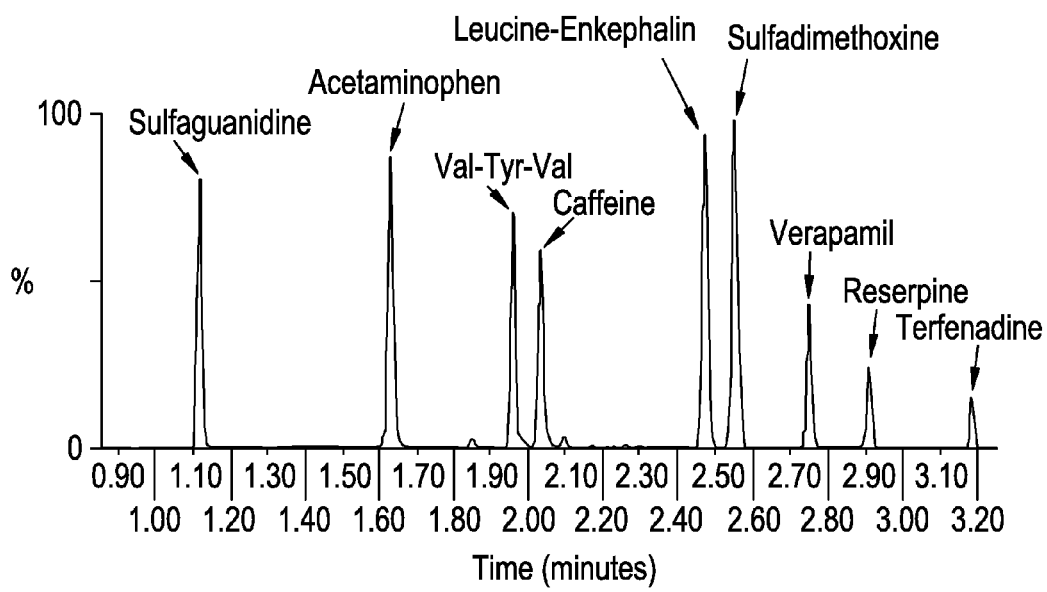

FIGS. 34A and 34B show (A) exemplary components for use in the LCMS QCRM mix and (B) a TOF MS ES+ spectrum of the LCMS QCRM standard using a methanol mobile phase with a SYNAPT® G2-S MS System (Waters Technologies Corporation, Milford, Mass.) operated in positive ion mode in high resolution mode.

Figure 35C:
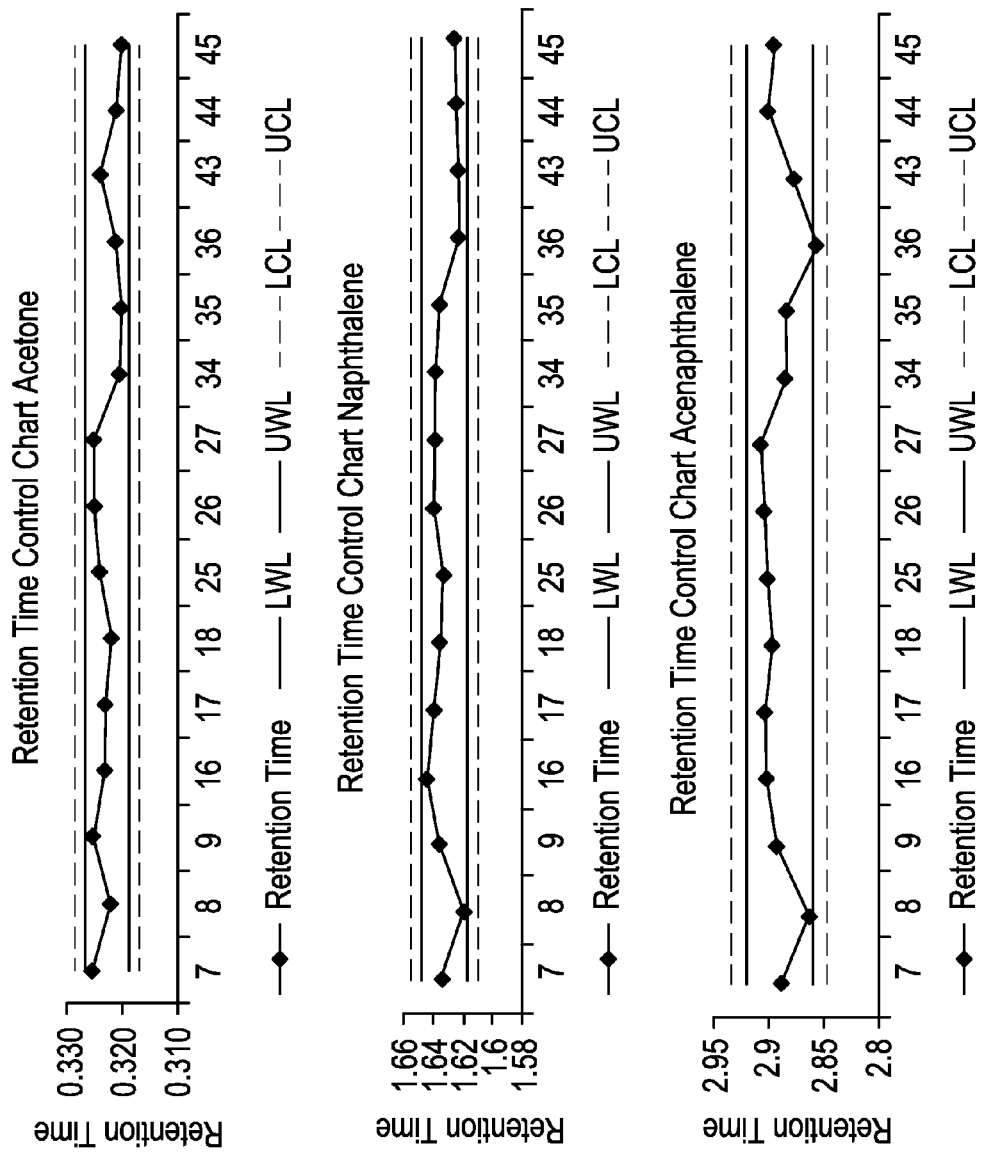

FIGS. 35A-35C show (A) exemplary QCRM retention time data, (B) example control chart limit calculations for the QCRM, and (C) retention time control charts for each component of the QCRM.

DETAILED DESCRIPTION AND EXAMPLES OF INVENTION

In order to more fully explain and enable the invention, the following description provides an introduction describing in greater detail QCRMs and their uses. The description also provides information about how to use the QCRM and chromatographic effects on neutral, acidic, or basic QCRM components. It also gives information about performing quality control (QC) measurements. Finally, the description provides information about general system troubleshooting, including mobile phase considerations, pump considerations, injector considerations, connecting tubing, in-line filter and guard column considerations, detector considerations, and column considerations.

Purposes of a QCRM:

Chromatographic system can be benchmarked with a suitability standard prior to system usage. QCRM should be run and compared with a previous benchmark before a critical assay is run, and after any hardware, column, or mobile phase changes.

The QCRM benchmark result can be specific to the performance of the system it is run on. All chromatographic systems can have some minor level of variability from run to run. Acceptable amounts of variability are discussed herein. Trending of benchmark results over time can provide an understanding of a system's typical variability. Trending of the same QCRM result on multiple systems can provide the typical variability of those systems. Trending of the same QCRM result on systems in laboratories in different locations can provide the typical variability from across locations. Setting specification for QC results of a system, multiple systems, or between laboratories generally should not be done without sufficient data trending. Once variability is understood, QCRM results can help determine the capability of a particular system to provide reliable results.

Determining QC Criteria:

Quality Control (QC) criteria can be determined based on user requirements. As mentioned above, specifications should not be set until the variability of the system population is understood. Specifications can help determine if QCRM results indicate that a system is functioning as expected, or outside of expectation. Typical criteria can include one or more of: retention time range or reproducibility, peak area range or reproducibility, peak tailing range, peak resolution, and mass accuracy range, sensitivity, or response.

What Affects QC Results:

The goal of a QC specifications and criteria can be to indicate that a system is functioning as expected or outside of expectation. Systems comprise many interdependent components working together. An issue with any one component can produce erroneous final results. All components performing correctly will produce results within an expected variability.

Some of the components to consider include, but are not limited to, mobile phase, column, tubing, pumping, injecting, temperature controlling, detecting, data collection rate, and integration parameters. Considerations also include, for example, the reservoir in which the solvent is stored (e.g., glass or plastic, covered to prevent contamination with particulates or other chemicals), material and state of tubing (e.g., no kinks or twists, effects of cold flow); filters (free of blockage); proper solvent preparation including degassing of solvents, pre-mixing vs. inline mixing of solvents, proper pH and buffering agents, proper timing of pH measurements (e.g., before or after addition of organic solvent), consistent lot usage, and proper column equilibration. Pump considerations include retention precision, which is directly related to solvent flow; consistent pump flow, as erratic pump flow can effect peak area; baseline noise, especially when synchronization with plunger movement can be related to the pump; and pressure changes that can affect peak size and shape. Column effects can be a result of age, voids, and channels in the column. An issue in any one of the components listed above can affect the QC result. Differences in any of the components mentioned can result in system to system variability of results even when each systems' components are functioning correctly.

QC Testing:

The use of reference standards for QC testing can allow a user to track important instrument parameters. The parameters that are important to chromatographic analyses, e.g., LC, HPLC, UHPLC, SCF, and carbon dioxide based chromatography analyses, include peak width, peak area, retention time, and peak resolution. Each of these important parameters can be tracked and evaluated using control charts. The use of a high quality reference standard allows the analyst to measure these properties must be designed to provide the analyst the data to evaluate and track these parameters.

Figures 2A, 2B:
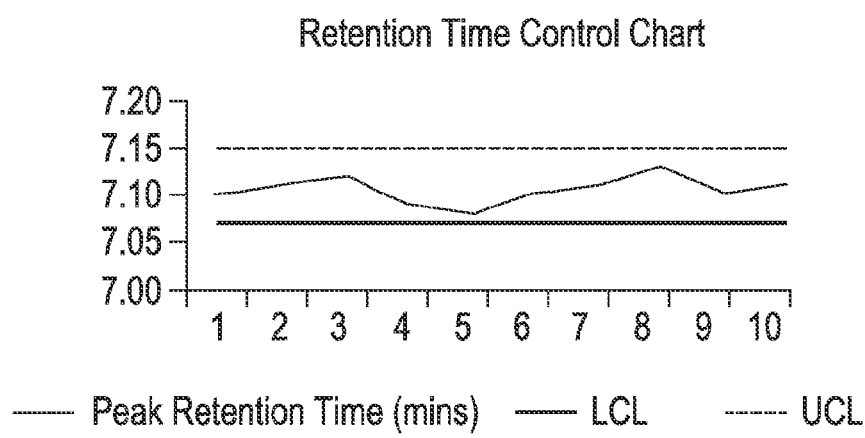
FIGS. 2A and 2B show (A) a table listing reference standard retention times and (B) a retention time control chart plotting the observed retention times demonstrating that all of the observed times fall between the LCL and UCL.

Quality Control testing can be conducted on a frequent basis for each instrument/analyst combination or instrument per test method. The data can be collected and entered into a control chart, such as the chart shown in FIG. 2A, allowing the analyst to evaluate the instrument performance. The use of instrument performance control charts is a staple of analytical chemistry quality control. A common form of the control charting is to track the analytical results and statistically analyze the data to a 99% (3 standard deviations) or 95% confidence interval (2 standard deviations) confidence interval around the mean of the data to establish upper control limits (UCL) and lower control limits (LCL) as shown in FIG. 2A. It is understood that, depending on the system and its uses, other UCL and LCL can be used including, for example, 1, 2, 3, 4, 5, 6, 7, 8, 9, or 10 standard deviations, or confidence intervals of 90%, 91%, 92%, 93%, 94%, 95%, 96%, 97%, 98%, 99%, or 99.5%.

The initial criteria to establish a mean, standard deviation and control limits involves analyzing a reference material, typically a minimum of 7 times (e.g., 7, 8, 9, 01, 11, 12, 13, 14, 15, 16, 17, 18, 19, 20, or more times) to establish an initial estimate of precision and bias. This can provide a user with sufficient data to be statistically valid. Analyses can be carried over the course of several days to provide a more realistic view of the instrument's variability. The frequency of analyzing system can be dependent on the stability of the analysis and the analytes. Quality of outputs can be analyzed after maintenance has been performed, a new analyst is assigned to the instrument, or other changes to the methods have been made. The below example uses retention time monitoring to establish a set of control limits for the purpose of monitoring on-going instrument performance.

The QCRM reference material was analyzed 10 times yielding the retention times shown in FIG. 2A. The mean and standard deviation were calculated from the data and the UCL and LCL limits were calculated. The control limits represent a 95% confidence interval for the data. The control chart in FIG. 2B was then produced to establish that the instrument retention times are in control.

The establishment of control limits provides data as to the current capabilities of the instrumentation. The next step is to determine whether the instrument is performing to the specifications necessary for the intended application. Control charting allows the analyst and quality professional to compare instrument performance to the required method specifications.

The process of continuing quality improvement is tracked using control charts. When improvements are made to a method, control charts facilitate monitoring the affects of changes made to the method and to determine if the modifications are effective and having the desired impact. The control chart facilitates tracking trends over time by seeing the data trending higher or lower, allowing preventative action to be taken prior to having an out of control situation or complete system failure.

Similar control charting can be created for at least each of the following important chromatographic properties: peak retention time, peak area, peak width, and peak resolution. The use of control charts allow for the analysts and quality control professionals to establish statistically derived criteria to monitor and control their chromatography analyses (e.g., LC, HPLC, UHPLC, SFC, and carbon dioxide based chromatography analyses). Statistically derived control limits avoid tendencies to have criteria that are too stringent or arbitrary.

Using high quality reference standards specifically designed for QC analysis provide controlled, consistent, and reproducible results indicating instrument performance. Using standard reference standards frequently for each instrument and control charting the resulting data provide information regarding instrument performance and confirm that the data produced are high quality, reliable, reproducible data.

Use of QCRM to Monitor System Performance

This section provides examples for measuring several of the possible QC benchmark criteria that can be monitored in the methods of the invention. The criteria can be used in any combination. The disclosure provided herein includes exemplary embodiments of the order in which the benchmark criteria should be assessed; however, other embodiments can be developed by those of skill in the art. The criteria and specifications allow the user to determine if the QC results indicate that the system is functioning as expected, or outside of expectation. Setting specification for QC results of a system, multiple systems, or between laboratories should not be done without sufficient data trending. Once variability is understood, QC standard results facilitate determination of the capability of the system tested to provide reliable results.

Chromatographic Effects on QCRM: Neutral, Acids, and Bases

QCRMs are typically designed with a void marker, neutrals, acids, and/or bases. A particular mix may not be appropriate for all column types or sizes and all possible chromatographic conditions. Such considerations are well understood by those of skill in the art. The acid and base compounds will be affected by pH. Therefore, the user should select appropriate compound mixes based on the specific chromatographic assay and system requirements. A stable chromatographic system with unchanged chromatographic conditions should give the same retention and peak shape. The neutrals QCRM are typically used as a first step in troubleshooting any changes in QC results.

The neutrals QCRMs include a void marker and two neutral compounds. Neutral QCRM compounds do not move with pH changes in a system that is in control. The neutral compounds are not ionizable and provide the same retention and peak shape at any pH in a system that is in control. Therefore, changes in peak retention and/or shape are indicative that the system is out of control.

Upon detection of a shift in retention time of one or more of the neutrals QCRM, the system is investigated for a problem with the pumping system or mobile phase. Problems indicated by such a degradation can include loss in bonded phase of the column.

Upon detection of a shift in peak shape of one or more of the neutrals QCRM, the system is investigated for a problem with the injector, or system volume change due to fitting or connections; or a data rate or time constant that may have changed. Problems indicated by such a degradation include a change in the column bed or void.

If the neutrals QC results have not changed, QCRM acid and/or base compounds are tested. Shifts in one or more components of the acids and/or bases QCRM are indicative of a problem with mobile phase preparation.

Detection of a degraded peak shape in both QCRM acid and base compounds are indicative of one or more of any of a number of problems depending on the observations made. For example, trailing shoulders or tailing peaks on every component can be indicative of a column void issue. Co-eluting peaks can be indicative of a gradient proportioning issue. Degraded peaks can also be indicative of a mixed mode mechanism or not enough ion pairing reagent.

A detection of a shift in only acid peak retention or only base peak retention can be indicative of a problem with the mobile phase composition.

Detection of a shift in only acid peak shape or only base peak shape can be indicative of various problems depending on the shape of the peak. For example, a peak that tails or fronts badly between good peaks and reproduces can be indicative of a chemistry problem. In the case of weak acids or bases run in the mobile phase that is near their pK, tailing may be observed even on highly functionalized columns, typically indicating an ionization problem rather than a column interaction problem. Degradation of peak shape in a basic compound can be indicative of the compound sticking to silanols. Degradation in peak shape can also be indicative that the column is being used at the wrong pH or includes a contaminant from the prior injection.

The significance of changes in peak shape and mobility are generally discussed above. More detailed explanations of methods and calculations to monitor changes in shape and mobility of peaks are provided below.

Quality Control Measurements

Low column efficiency may not always be due to column degradation. To determine the exact cause, the entire system should be subjected to a troubleshooting analysis to determine the exact cause. Preferably, the quality control measures are compared to baseline measurements obtained at the time the system was set up and quality control assays were performed by the manufacturer. Quality control measures should be tracked, as described above, to provide an appropriate standard for comparison. It is understood that the methods provided throughout the application to assess system performance can include the step of comparing the results to one or more (e.g., 1, 2, 3, 4, 5, 6, 7, 8, 9, 10 or more) prior assessments of the same parameter to assess and monitor system performance over time. When evaluating system performance, all measurements must all be made in the same unit (minutes, milliliters, millimeters). Recommended practice is to use volume for all dimensions.

System Bandspreading Analysis

A bandspreading measurement is used to determine if low column efficiency is due to degraded system performance. If bandspreading has increased, the analysis provided below permits analysis of the hardware components of the system that do not include the column, e.g., the injector, detector, or tubing (internal diameter, length, etc.). The exemplary procedure illustrates measuring bandspreading at a peak width of 4.4% of the height of the peak height (in μL).

To perform system bandspreading:

1. Measure column efficiency. If column efficiency is normal;

2. Remove only the column and install a zero dead volume (zdv) union in its place. If additional system backpressure is observed during this procedure (especially if using an auto injector), use a piece of 0.009-inch (0.23 mm) ID tubing (or suitable restrictor) instead of a union.

3. Configure the system to the standard parameters used to assess the system. The detector parameters should be set to a high data rate and a low time constant (filter). The following exemplary parameters are provided.

| Parameter | Setting |
| --- | --- |
| Flow Rate | 0.5 mL/L |
| Detector Time Constant | Fast |
| Data Rate | 20 Hz |

4. Dilute the column efficiency test mixture as needed in the mobile phase. Inject an appropriate injection volume usually 1 to 5 μL of the solution (e.g., 1 μL acetone as a 10% solution diluted in the mobile phase).

Figure 3:
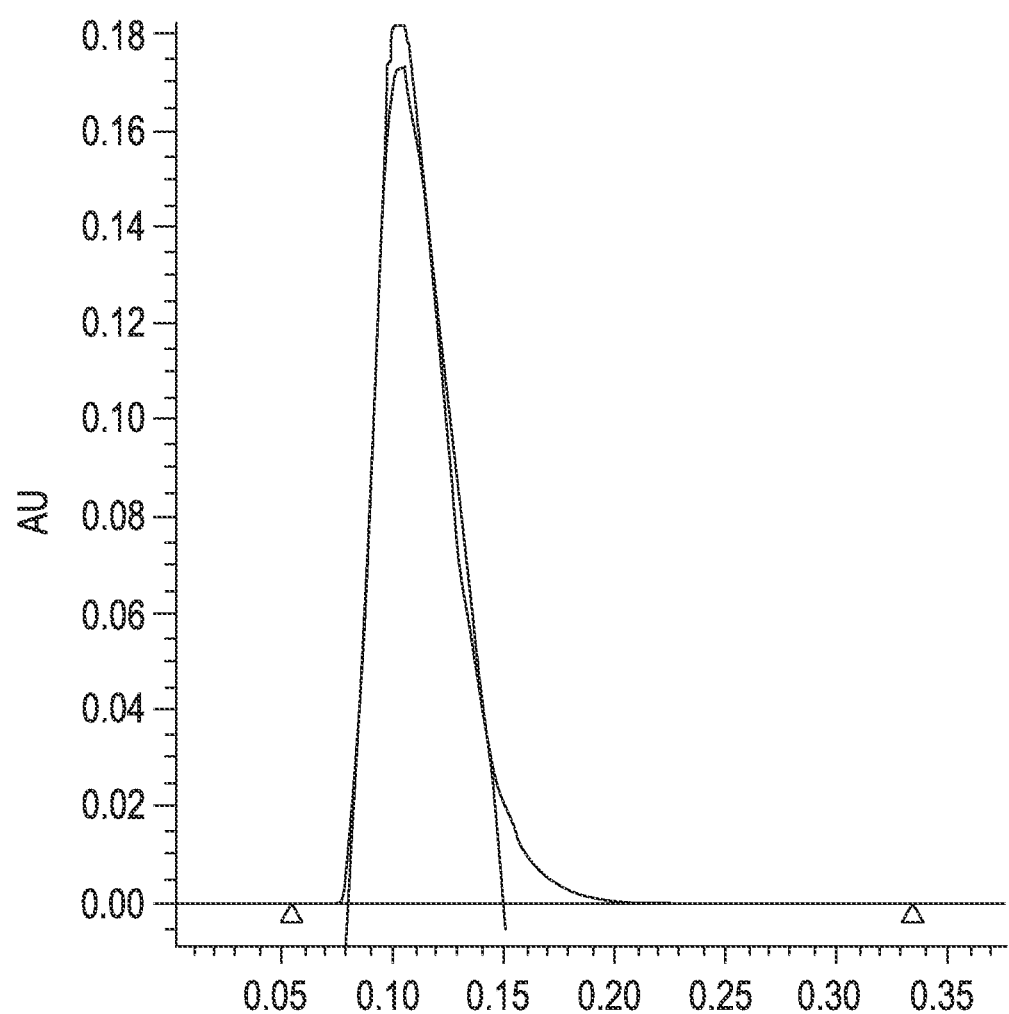
FIG. 3 shows a representative chromatograph peak for calculation of band spread volume.

5. Using the USP column efficiency method, measure the peak width at the baseline of the peak as shown in FIG. 3 by the Tangent method. Calculate the bandspread: peak width (min)×flow rate (mL/min). Certain detectors with built-in added volume (such as counter current heat exchangers) may show increased values as well. Bandspread volume should be less than 90 μL with 3 mm internal diameter (ID) columns. For microbore or non-standard analytical cells, the manufacturer or manufacturer's instructions should be consulted.

6. If the bandspreading value is greater than anticipated, the LC system should be further analyzed in the following order to isolate the cause of increased bandspreading: check tubing to ensure that it is properly installed and has the correct internal diameter; check the in-line filter for blockage; check the injection for proper functioning; and check the detector for proper functioning.

7. Upon identification of a problem, re-measure system bandspreading. If the bandspreading value is reduced, the problem is resolved. If the value is still high, continue to investigate the other areas within the LC system. Recalculate system bandspreading until the value is reduced.

Standard Parameters for Analysis of System Performance

System performance should be measured to see if trends are occurring which may lead to future problems. In addition, if chromatography begins to degrade (e.g., quality of peak separation or peak shape), system performance should be evaluated to determine if the problem is column, hardware, mobile phase, or sample-related.

System performance analyses include, but are not limited to: system resolution (Rs); retention factor (k'); column selectivity (α); and column efficiency (N or column plate count). Methods to measure and calculate these system performance analyses are provided below.

Measuring Resolution

Figure 4:
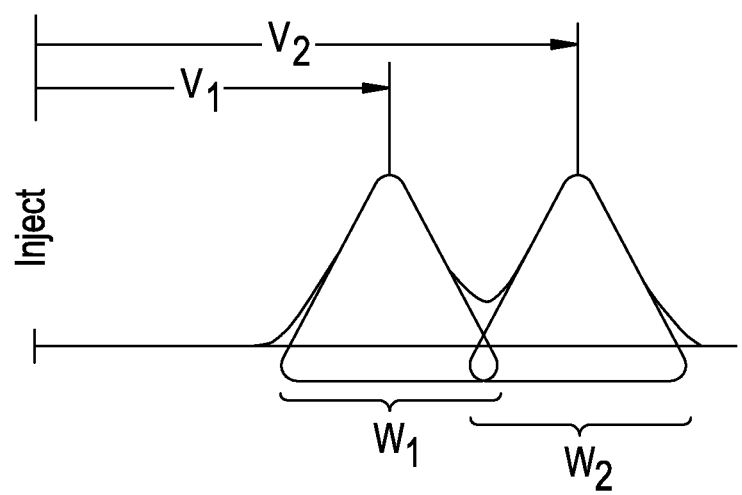
FIG. 4 is a schematic showing the variables used for calculation of resolution and quality of separation.

Resolution is the distance between the peak centers of two component peaks divided by the average base width of the peaks. The following calculation is used to indicate the quality of the separation. See FIG. 4 for clarification of measurements related to the variables indicated below.

$$Rs = \frac{V_2 - V_1}{\frac{1}{2}(W_1 + W_2)}$$

Where:
Rs=resolution
$V_2$=apex (retention volume of peak 2)
$V_1$=apex (retention volume of peak 1)
$W_1$=width of peak 1
$W_2$=width of peak 2

Components of Resolution

There are three fundamental parameters that influence the resolution of a chromatographic separation: retention factor (k'); selectivity (α); and column efficiency (N). These parameters provide different means to achieve better resolution, as well as defining different problem sources.

Resolution is a function of k', α, and N as shown below:

$$R_s = 1/4\left(\frac{\alpha - 1}{\alpha}\right)(\sqrt{N})\left(\frac{k'}{1 + k'}\right)$$

Figure 5:
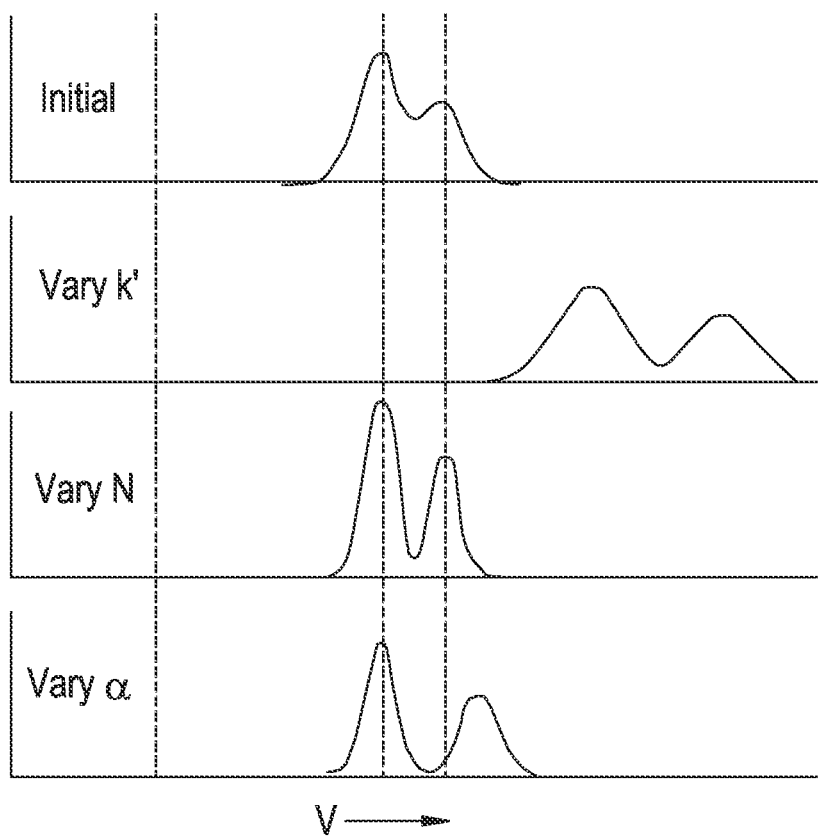
FIG. 5 is a schematic showing how variation in chemical factors alters the shape of the elution curve.

Where:
Rs=System resolution
α=Column selectivity
N=Column efficiency
k'=Retention factor The affect of k', N, and a have on system resolution are shown in FIG. 5. Initially, the two compounds are partially separated. The resolution of the compounds can be changed in three different ways:

1. If k' is increased, resolution is increased but the peaks become broader. Decreasing k' sharpens the peaks but decreases Rs.

2. If N decreases, the resolution decreases because peak width broadens. However, the center-to-center (apex-to-apex) distance is constant. When N is increased, the peak width narrows.

3. If α is increased, resolution is increased because one peak moves relative to another.

Measuring Retention Factor (k')

Retention factor (k') is a measurement of the retention time of a sample molecule, relative to column dead volume ($V_0$). Note that $V_0$ is measured using a probe molecule that is unretained by the column under standard test conditions. Consult the column operator's manual for the appropriate probe molecule to use.

Retention factor (k') changes are typically due to: variations in mobile phase composition; changes in column surface chemistry (e.g., due to aging); and changes in operating temperature. In most chromatography modes, retention factor (k') changes by 10 percent for a temperature change of 5° C.

Calculating Retention Factor (k')

The equation below is used to calculate retention factor (k'):

$$k' = \frac{V_1 - V_0}{V_0}$$

Figure 6:
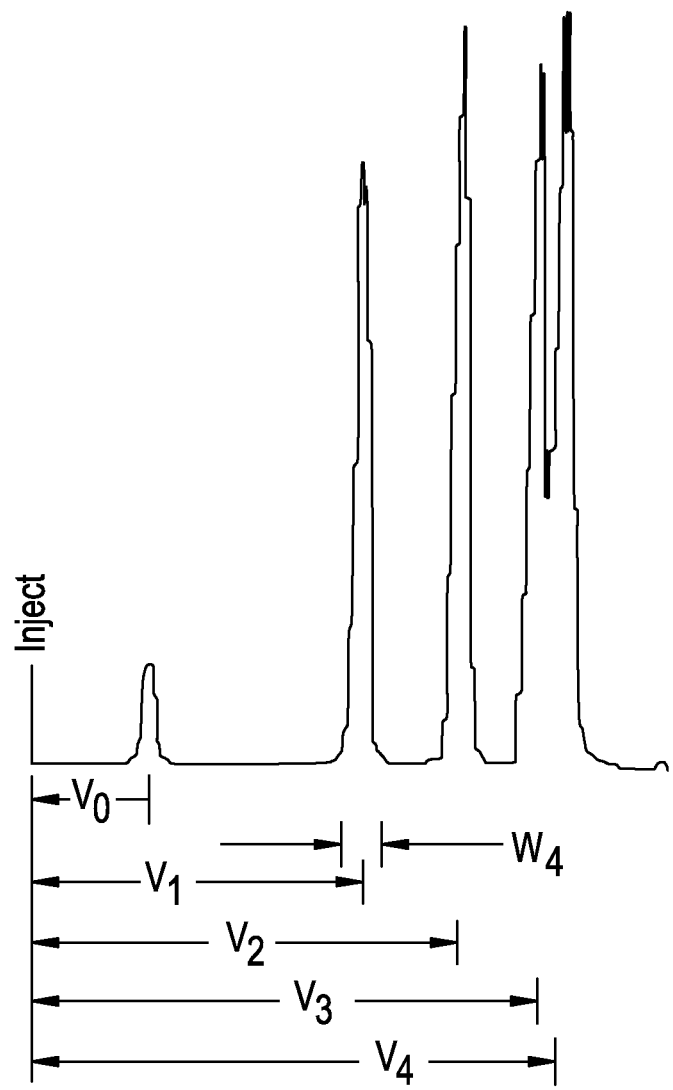
FIG. 6 is a schematic showing the variables used for calculation of column selectivity.

Where:
k'=Retention factor of the column
$V_0$=Void volume (or dead volume) of the column (volume at which an unretained component elutes)
$V_1$=Retention volume of peak 1
See FIG. 6 for further clarification of variables in the equation.

Adjusting Retention Factor (k')

Good isocratic methods usually have a retention factor (k') in the range of 2 to 10 (typically between 2 and 5). Lower values may give inadequate resolution. Higher values are usually associated with excessively broad peaks and unacceptably long run times. If the analytes fall outside their specified windows, an initial column test protocol should be run to compare the results with when the column was new.

Retention factor (k') values are sensitive to the following change in conditions: solvent strength, composition, and purity; temperature; column surface chemistry; and sample identity. If the shift in retention factor (k') value is observed with both analytes and the column test solution, the problem is most likely due to a change in the column, temperature, or mobile phase composition. This is particularly true if the shift occurs gradually over a series of runs. If, however, the test mixture runs as expected, the problem is most likely sample-related.

From the possible causes, refer to the system benchmark comparisons to evaluate the origin of the problem. For example, changes from the system benchmark values can indicate: changes in mobile phase composition; changes in operating temperature; and aging of the column.

Calculating Selectivity

Selectivity ($\alpha$) is the relative retention of two peaks in a chromatogram (the ratio of two k' values). Problems due to selectivity ($\alpha$) changes result in some peaks moving significantly relative to other peaks. Usually, selectivity ($\alpha$) can be controlled in LC by varying the "chemistry" of the system, such as mobile phase (pH, salt strength, organic solvent and composition type, or modifier type) or type of column.

Selectivity ($\alpha$) is calculated using the following equation $$\alpha = \frac{V_2 - V_0}{V_1 - V_0} = \frac{k'2}{k'1}$$

Where:
$\alpha$=Relative retention
$k'_1$=Retention factor for $V_1$
$k'_2$=Retention factor for $V_2$
$V_0$=Void volume (or dead volume) of the column (volume at which unretained component elutes)
$V_1$=Retention volume of peak 1
$V_2$=Retention volume of peak 2

See FIG. 6 for further clarification of variables in the equation.

When troubleshooting changes in selectivity ($\alpha$), the approach is similar to the approach used to troubleshoot changes in retention factor (k'). When selectivity ($\alpha$) is affected, the corrective action depends on whether the problem is mobile phase or column-related. Results should be compared to those obtained with the test solution and to those observed when the column was new. The results are used to identify column changes from problems with mobile phase or other operating parameters. As noted above, selectivity ($\alpha$) values are sensitive to changes in mobile phase composition (pH, ionic strength) and purity; temperature; and the age of the column.

As outlined in Measuring Retention Factor (k'), after adjusting factors that could be causing abnormal selectivity values, the test solution should be rerun and results compared to prior results, both the abnormal readings and from when the column was new. From the possible causes listed above, the origin of the problem is evaluated.

Measurement of Column Efficiency

The column efficiency (N) (also called theoretical plate count), is a measure of the bandspreading of a peak. The smaller the band spread, the higher the number of theoretical plates, which indicates good column and system performance.

The measurement of column efficiency is actually the total efficiency for the LC system and column combined. A decline in measured efficiency may be due to one or more of: age and history of the column; extra column band broadening (such as due to a malfunctioning injector or improper tubing ID); inappropriate detector settings (for example, time constant); and change in flow rate and solvent viscosity.

Figure 7:
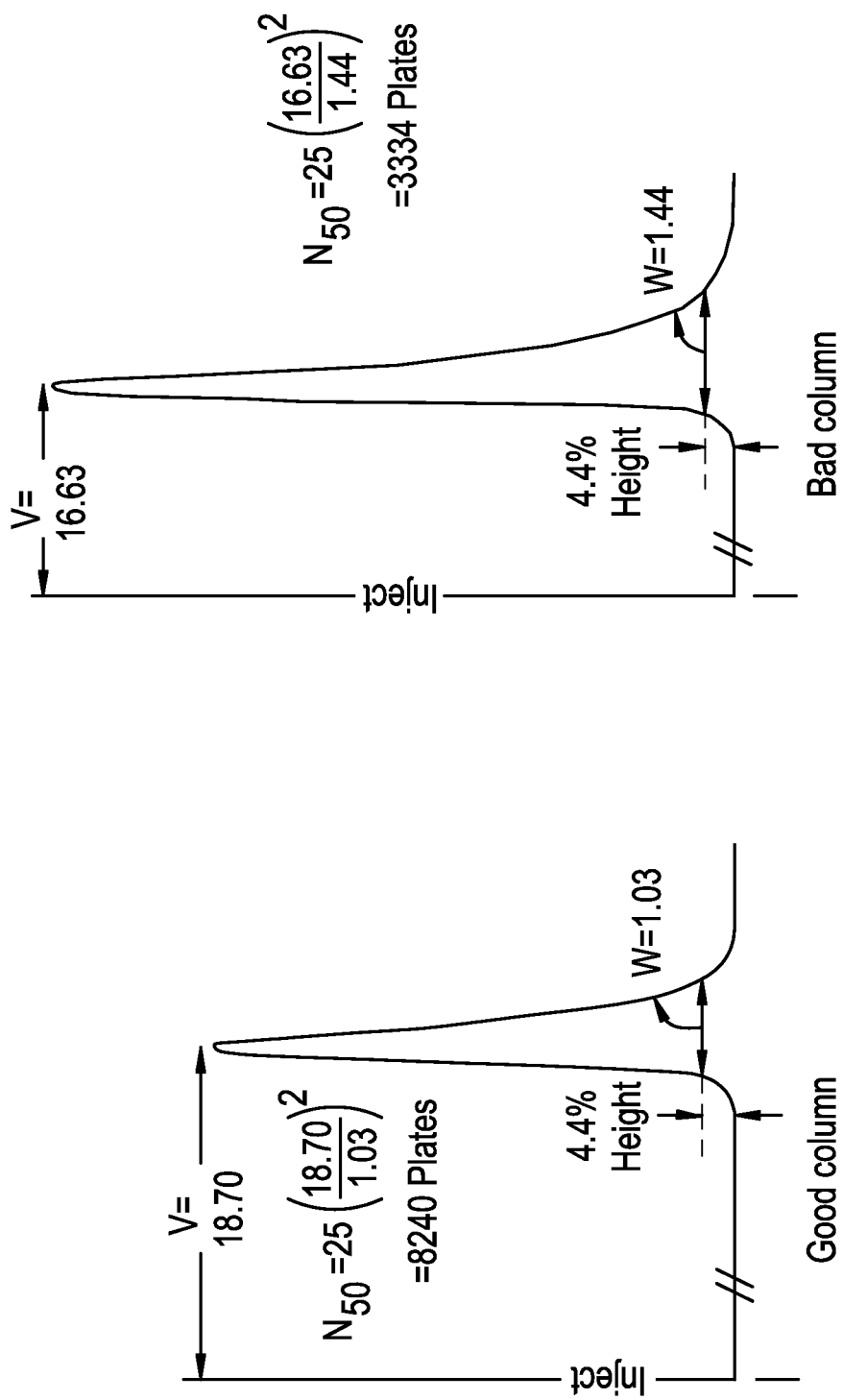
FIG. 7 shows two chromatographic peaks generated on a good column and a bad column and calculation of the number of plates based on the peak measurements.

Problems in separation due to a loss of column efficiency can be recognized be a change in the width and/or shape of all peaks are affected. FIG. 7 illustrates low efficiency and high efficiency peak shapes.

To confirm that the problems observed are due to a loss of efficiency, the column test performed when the column was new should be repeated, e.g., the test with the probe provided by the column manufacturer. If the test result is similar to the first test, the problem is specific to the method in use. If the measured efficiency has degraded, either the column has degraded or system band-broadening has increased. However, if a guard column is being used, it can be a source of band-broadening and the component most likely to fail first. Therefore, system efficiency should be monitored and documented with and without the guard column.

If the measured column efficiency is low (less than 75 percent of the original measurement for the column), the source of the problem can be isolated by replacing the column with a new or known good column. The column efficiency should be measured for the new column. If the column efficiency is normal for the replacement column, the prior column should be replaced. If exchanging the column does not increase the efficiency of the system, other causes of potential problems should be investigated including incorrect tubing ID, guard column, plugged filters and frits, malfunctioning injector, or malfunctioning detector.

Delay Volume

Delay volume is the volume from the point where the gradient begins mixing through the pump and injector to the head of the column. Delay volume affects gradient separation. A gradient method developed on one type of system or a system with a first set of tubing lengths cannot be directly transferred to another system or the same system with different tubing lengths. The gradient table must be modified to obtain the same separation.

Figure 8:
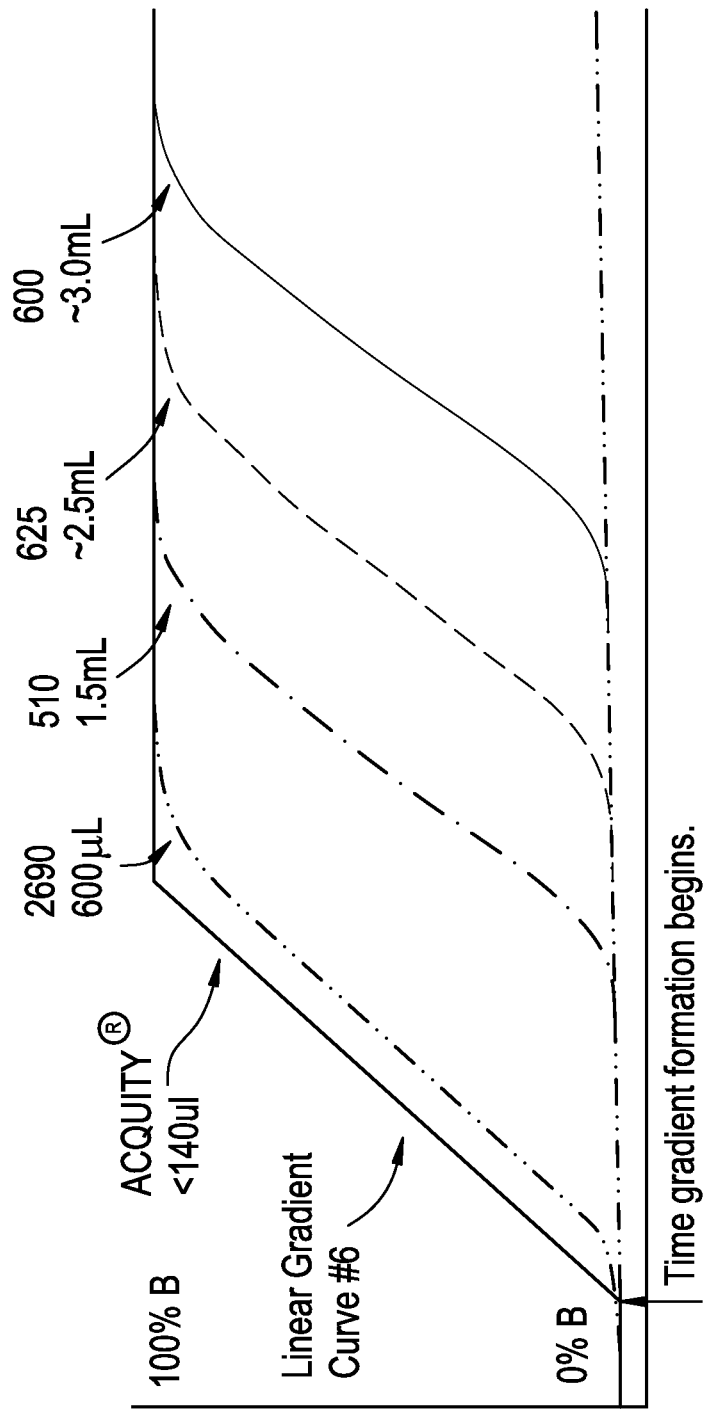
FIG. 8 shows variations in delay volume that can occur as a result of changes in the system used.

To determine the delay volume of a system, the column is replaced with a union. The first of the gradient components (e.g., methanol) is placed in the A reservoir and the second gradient component (e.g., methanol) with a small amount of a component that can be detected by the detector in the system (e.g., UV or PDA 0.5 mg/L methyl paraben). Lines are flushed completely. The system is programmed to generate a linear gradient form 0% B to 100% B over 10 minutes at 1.0 mL/min. The % B is plotted as a second channel and the system is allowed to run at 100% B until the detector stabilizes. The plots are overlaid. The time between the % B plot and the detector plot at 50% B is measured. The time in minutes is multiplied by the flow rate is the delay volume. Dwell times for various LC systems are shown in FIG. 8.

Figure 9:
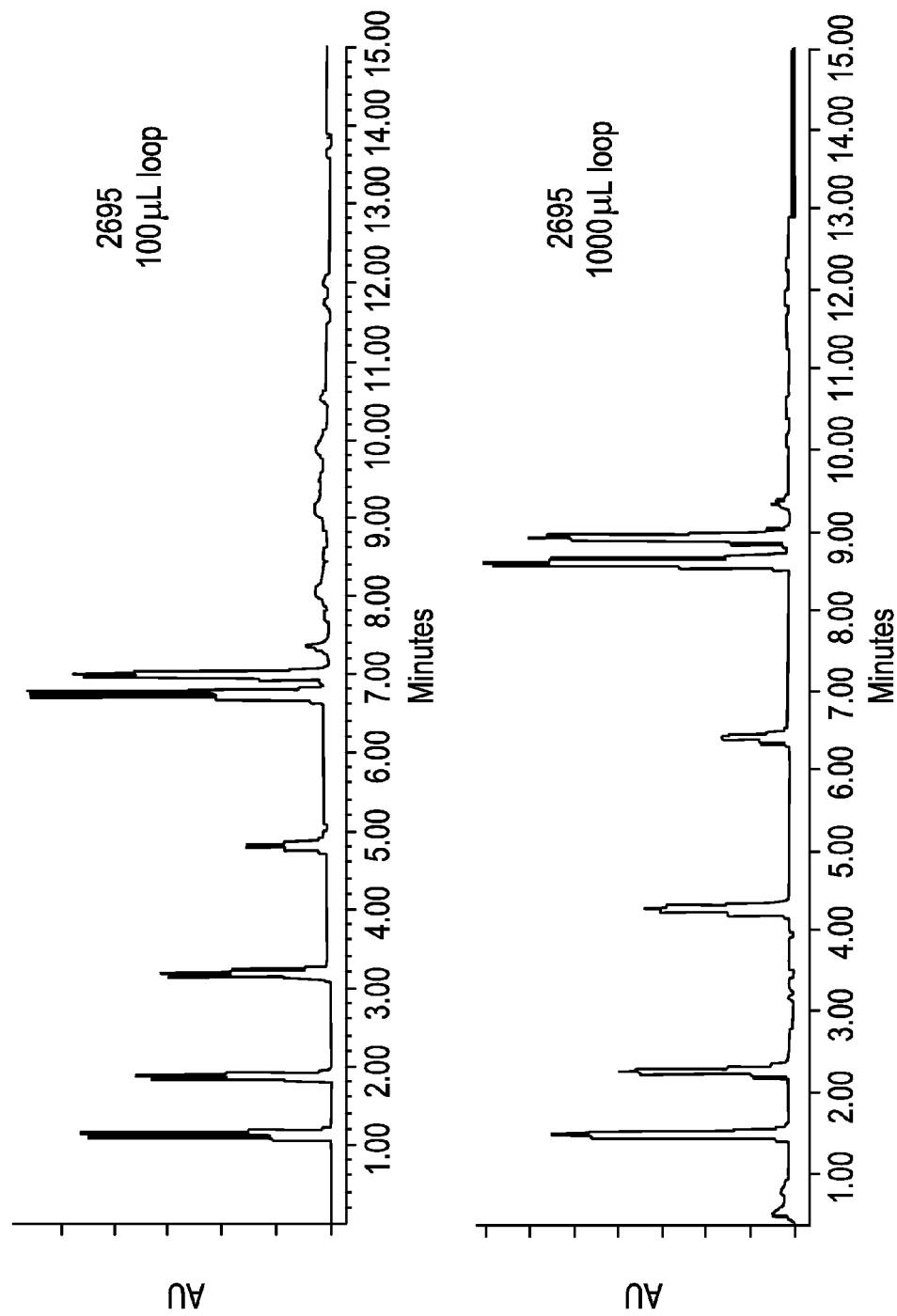
FIG. 9 shows variation in retention time that can occur as a result of variations in loop length.

Retention times can also be altered by the use of different tubing lengths on the same system as shown in FIG. 9. The same samples were run using a 100 µL loop and a 1000 µL loop. A significant delay in retention time was observed for each of the peaks. The differences in retention time can be more pronounced when different injectors and/or pumps are used. Changes in injectors and pumps can also result in changes in delay volumes. Further, when doing in-line mixing, isocratic separations are not generally affected by delay volume differences. However, the exception is when the volume is reduced so much that complete mixing does not occur.

Injector Function Analysis

Injector malfunction can be detected by various chromatography problems including, but not limited to: an absence of peaks as a result of the needle not being properly inserted in the vial, the valve not opening and closing properly; and/or the sample not being withdrawn; poor peak shape including tailing, shoulders, and doublets as a result of valve problems; poor peak area reproducibility as a result of syringe or valve problems; and ghost peaks as a result of residue from previous injections. Contamination can arise from one or more of the needle wash solvent, the mobile phase sample or solvent, or contamination in the injector.

System Efficiency

Using the compositions and methods provided herein, the functionality of various components of the LC system can be tested and analyzed. The results from the analyses are used to pinpoint and diagnose problems in the LC system, including column effects and non-column effects (mobile phase, pump, injector, connecting tubing, in-line filter, guard column, detector, etc.), based on the calculated values for system parameters in comparison to previously obtained values, preferably values obtained both when the system was new and throughout the time that the system was used. These compositions for systematic analysis of a chromatography system result in one or more of greater accuracy of results, greater precision of results, greater reliability of the system, the ability to compare results over time and possibly between systems.

Figure 10A:
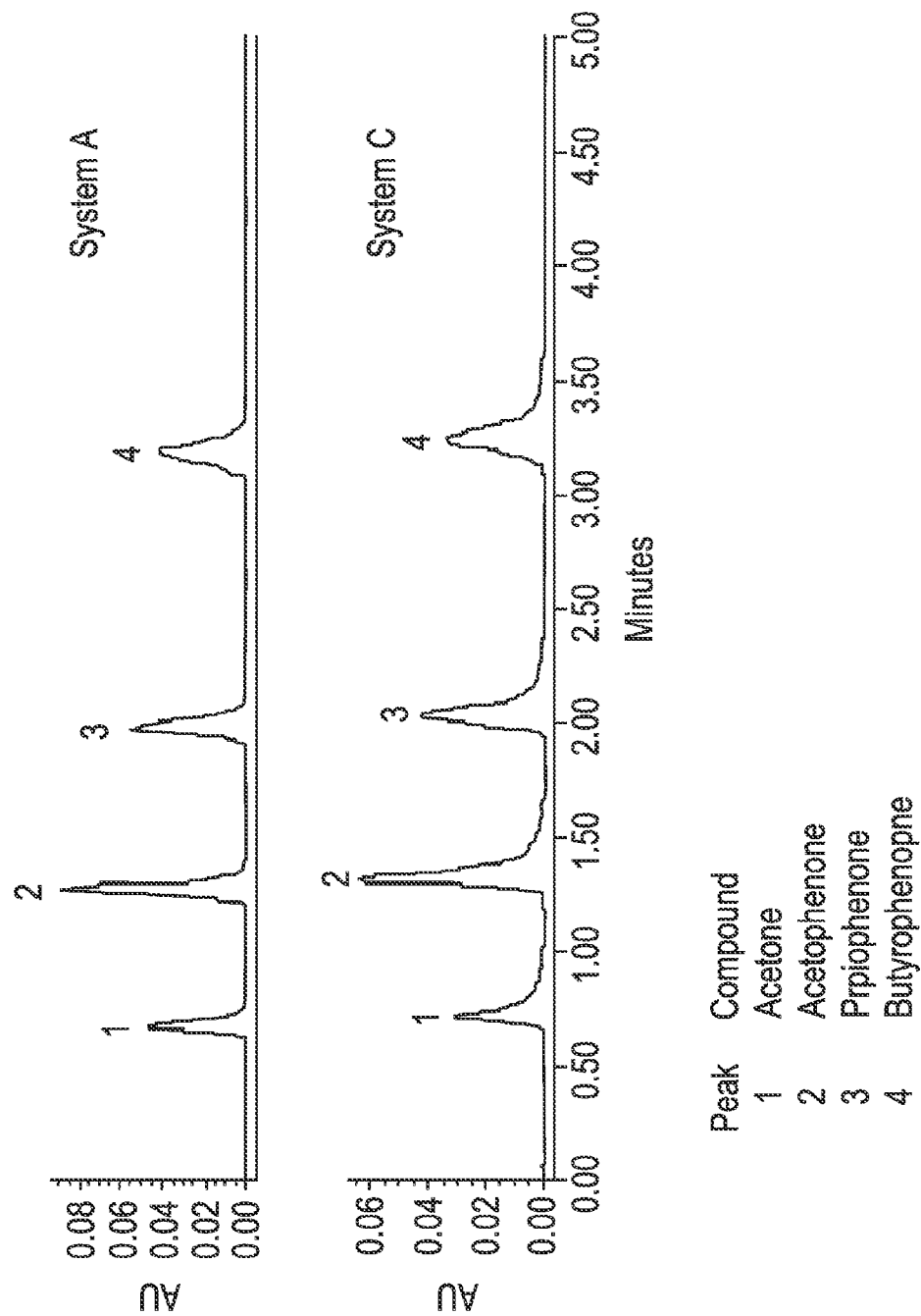

System efficiency between two identical systems were compared using the same mobile phase and the same sample, which was a mixture of acetone, acetophenone, propiophenone, and butyrophenopne. Both columns were new. The results are shown in FIG. 10A. System C had noticeably more band spreading than System A. This suggests that the column used in System C may have been bad, or that non-column problem(s) were present in System C.

System efficiency can be calculated using the USP method, also known as the Tangent method using the following formula:

$$N_{tot} = 16\left(\frac{V_{tot}}{W_{tot}}\right)^2$$

Where
$V_{tot}$=elution volume to peak apex
$W_{tot}$=peak width (4 sigma)
$N_{tot}$=total plates (4 sigma)

Figure 10B:
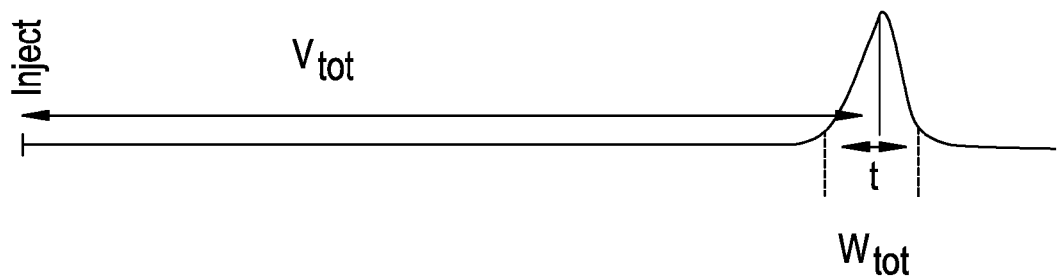

See FIG. 10B for further clarification of variables in the equation. Calculations of column efficiency based on the shape of peak 4 in FIG. 10A in Systems A and C shown is FIG. 10C. FIG. 10D provides additional equations for assessment of column efficiency. Such equations can be used alternatively, or in conjunction with, other assessments provided herein.

The efficiency of an LC system tells how well it will separate (resolve) peaks. The narrower the peaks, the higher the efficiency and the better the resolution. Time can be used instead of volume in this calculation; however, all measurements must then be in time units. $V_{tot}$ becomes RT (retention time) and peak width can be taken from QCRM calculations using the tangent result.

Factoring Out Non-Column Effects

Figure 11:
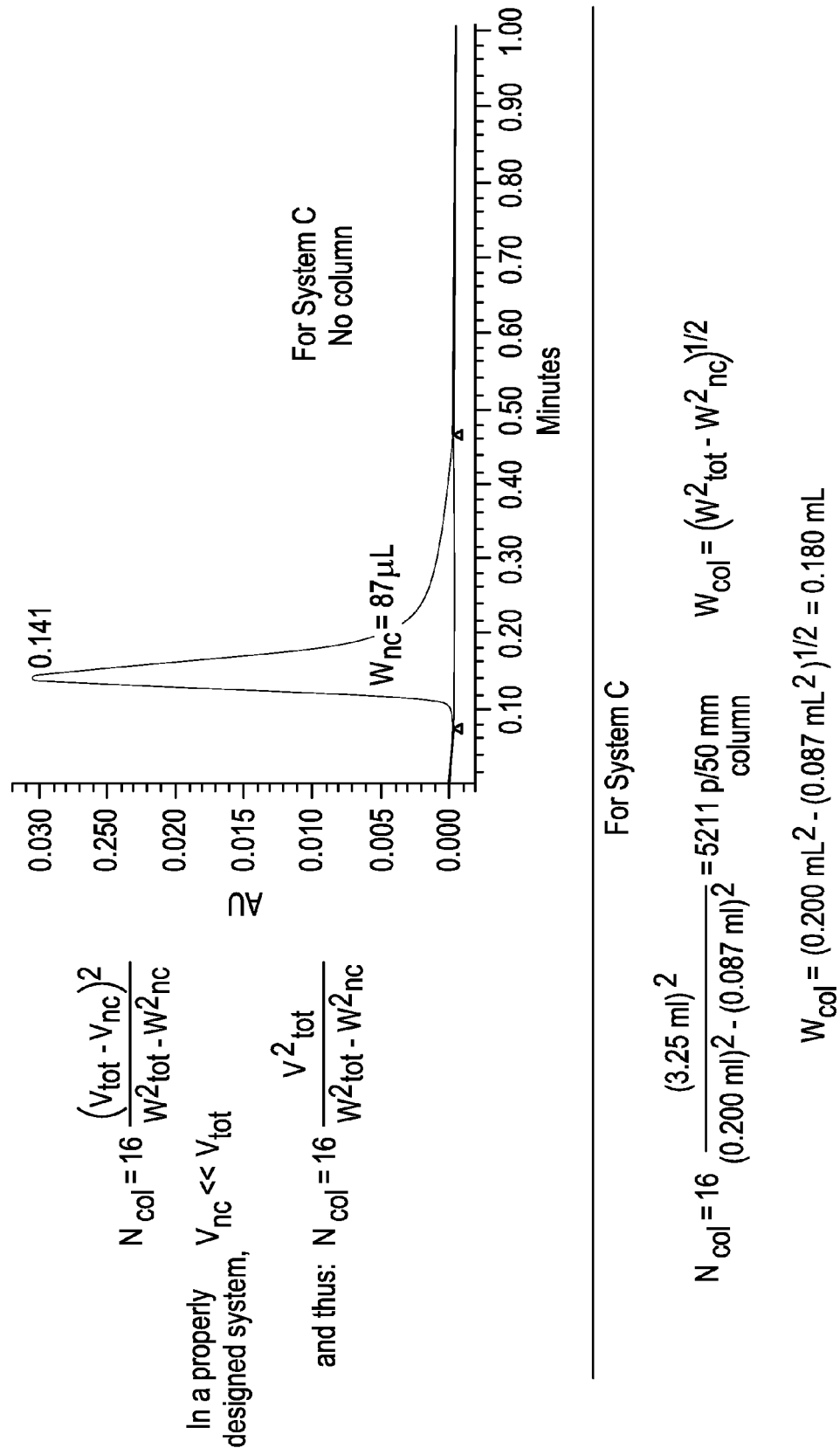
FIG. 11 shows a simplified calculation for a system not containing a column based on one of the equations in FIG.

Systems can be tested without a column in place to assess non-column effects. The column is replaced by a connector, preferably a zero volume connector, for such assays. The equation provided above simplifies when the column void volume is significantly larger than the system volume. In such a system, retention of the peaks from the system is almost zero. The calculations to simplify the equation and the results from the analysis of System C without a column are also provided. Based on the calculation, the column is determined to have good efficiency as the peak is still broad even in the absence of a column as shown in FIG. 11. The results suggest the injector may be a contributor to the poor system efficiency and the 180 μL observed bandspread.

Bandspread vs. Time Constant vs. DPS

Assessing bandspread can be significantly misleading if a filter time constant is too high, or the data points per second are too low. As shown in FIG. 12, the apparent bandspread is calculated as 60 μL for the time constant of 0.1. However, when the bandspread is calculated as 100 μL for the time constant of 1.0, this is artificially high. There is a significant difference in peak apex and possibly retention time when 1 data point per second is used. Faster chromatography methods, e.g., UHPLC using UPLC® columns and systems, require higher data rates and lower filter time constants.

Connecting Tubing, in Line Filter, and Guard Column Considerations

Connection tubing must be made of a material compatible with the reagents to be used in the LC. The tubing must also be structurally sound, being free of kinks or other structural impediments to reagent flow. Tubing must also have an appropriate internal diameter. In-line filters are typically 2 μM pore size filters that are placed between the injector and the column to prevent particulates from reaching the column. Guard columns are short sections of column placed before the analytical column to scavenge damaging sample components from the analytical column. The packing material in such columns must be considered to ensure that it does not create problems with the analytical column. The use of an in-line filter or guard column is not a substitute for proper preparation of reagents. In-line filters and guard columns can become blocked with particulate materials or other contaminants inhibiting flow. Problems with in-line filters or guard columns can reveal themselves as high pressure, poor peak shapes, baseline drifts, missing peaks, or bad chromatography.

FIG. 13 shows that a contaminated in-line filter resulted in trailing, poor peak shape, and high pressure. Upon replacement of the in-line filter, both system pressure and peak shape were normalized.

Tubing diameters can have a significant effect on system performance. Tubing that is too narrow (e.g., 0.009" internal diameter) can become blocked, resulting in poor peak shape and high pressure. Tubing that is too wide (e.g., 0.040" internal diameter) can result in poor column efficiency and bandspreading. FIG. 14A demonstrates that upon replacement of the column with a zero volume union, or a 12 inch length of tubing with internal diameters of 0.009, 0.020, and 0.040 a significant increase in peak width (bandspread) was observed.

The results in FIG. 14A are confirmed by those of FIG. 14B which provides a table demonstrating that the internal diameter of a tubing has a greater effect on bandspreading than the length of the tubing in a chromatographic system.

Viscosity of Mixtures of Water and Organic Solvents

Viscosity and, therefore, pressure change dramatically for some mixtures of organic solvents and water. Viscosity curves are show in FIG. 15. The curves show an increase in viscosity from 100% acetonitrile to 80% water and a small decrease in viscosity when changing from 80% to 100% water. The effect is more pronounced when mixing water and methanol. Viscosity more than doubles from 100% methanol to a 50% water-50% methanol mixture. The effect of this change in viscosity (and pressure) is that a gradient run on a reverse phased column from 100% water to 100% methanol, results in a pressure increase by a factor of approximately 1.8 followed by a pressure decrease factor of 2 when reaching 100% methanol. From the curves, it can also be readily seen why ethanol is not a commonly used HPLC solvent due to a system pressure that is nearly double that of methanol. Variations in pressure can affect system performance.

Fitting Selection

Setting the ferrule at the proper distance from the end of the tube is necessary to minimize bad spreading. Problems can arise when using tubing fittings on the inlet and outlet ports of columns from multiple different manufacturers are used on the same system. Two different ferrules are shown schematically and in a photo in FIGS. 16A and 16B, respectively. The length of tubing 1606 extending from ferrule 1602 is shorter than the length of tubing 1608 that extends from ferrule 1604, potentially resulting in system performances. Differences in the internal structures of connector, e.g., 1620 and 1622, particularly the absence 1628 or presence 1630 of the void volume in the connector as indicated in FIG. 16B can result in changes in band shape and band spreading as shown in curves 1624 (no internal void) and 1626 (internal void). The end of the tubing must be square and flush with the internal machining of the end fitting. Otherwise, there is extra volume in the column connection where band spreading can occur. An improperly installed ferrule can cause band spreading, especially in fittings from the injector to the column, and from the column to the detector.

Detector Considerations

Improperly functioning or improperly programmed detectors can cause reductions or apparent reductions in system function. The detector must be consistent over both short and long intervals to ensure accuracy and precision within and between samples. Changes in baseline are characterized as drift, noise, or wander depending on if the changes are observed over an hour, over a minute, or over a period of time there between. Detector problems can also be caused by bubbles out-gassing before or inside the detector cell. The light source must be stable, including the lamp or LED and the power supply. Flow cells must be kept clean, and care must be taken in cleaning them, when necessary Time constants that average signal for a specified time can be used to reduce noise. Finally, the correct detector and detection rate must be selected for the appropriate application.

Effect of Wrong Detector Cell on system Bandspreading

Bandspreading depends on internal diameter of tubing and the length of the analytical cell. As shown in FIG. 17, the bandwidth of the chromatograph from the analytical cell is narrower than that of the semi-preparative cell due to shorter path length and larger tubing internal diameter in the semi-preparative cell than the analytical cell. Detectors should be adjusted in view of the geometry of the tubing and columns used.

Effect of Detector Time Constant

FIG. 18A shows three chromatograms in a stackplot that were all made from the same vial of sample using the same injection volume with varying detector time constants, specifically time constants of 0, 1.5 v per second, and 2.5 per second. Use of an inappropriate time constant results in an apparent loss of resolution and sensitivity upon lengthening the time constant. Similarly, an overlay of chromatographs made from the same vial of sample using the same injection volume using detector time constants of 0.2 per second and 1.0 per second shows an apparent retention time shift that occurs as the detector time constant is increased Column Considerations It can be helpful to consider system problems as a result of a column effects or non-column effects. Considerations related to proper column functioning and troubleshooting of column based problems include, but are note limited to: pressure considerations, particularly high pressure in relation to particle size and solvent composition; temperature control, especially as related to retention time shifts; retention time consideration, especially related to dirty columns; ghost peaks, especially related to dirty columns or chemical contamination that require cleaning the column with a strong solvent; poor peak shape, potentially due to loss of plate count, as a result of one or more of voids, dirty column, or packing degradation; loss of column efficiency, as a result of one or more of voids, dirty column, or packing degradation; direction of column flow through, wherein reversing the direction of flow can disrupt column packing; pressure shocks, wherein abrupt shifts in pressure from low to high or high to low almost instantly disrupt column integrity; column pH compatibility, with a pH of 3-7 for silica based columns being preferred; compatibility of end fittings with ferrules properly set on tubing; baseline drift, particularly in association with long retained material bleeding off of the column; column storage, with preferred storage conditions being wet in a compatible solvent at an appropriate temperature for the solvent, and under conditions free from mechanical shocks; and column cleaning.

Tailing Peaks

Tailing peaks due to column problems can be a result of one or more of: column overload due to too much mass or too large of a volume sample; competing mechanisms resulting in adsorption on C18 and silanol sites; column voids as a result of pressure shocks, mechanical shocks, or column drying; improper sample viscosity, typically a viscosity that is too high; co-eluting peaks; a bad guard column resulting in sample bleeds onto the analytical column; and a need for ion-suppression or PIC reagent which are application dependent. The above should be considered upon observation of tailing peaks in view of the specific sample and run conditions.

Tailing vs. pH and Ionization Issues

Figure 19A:
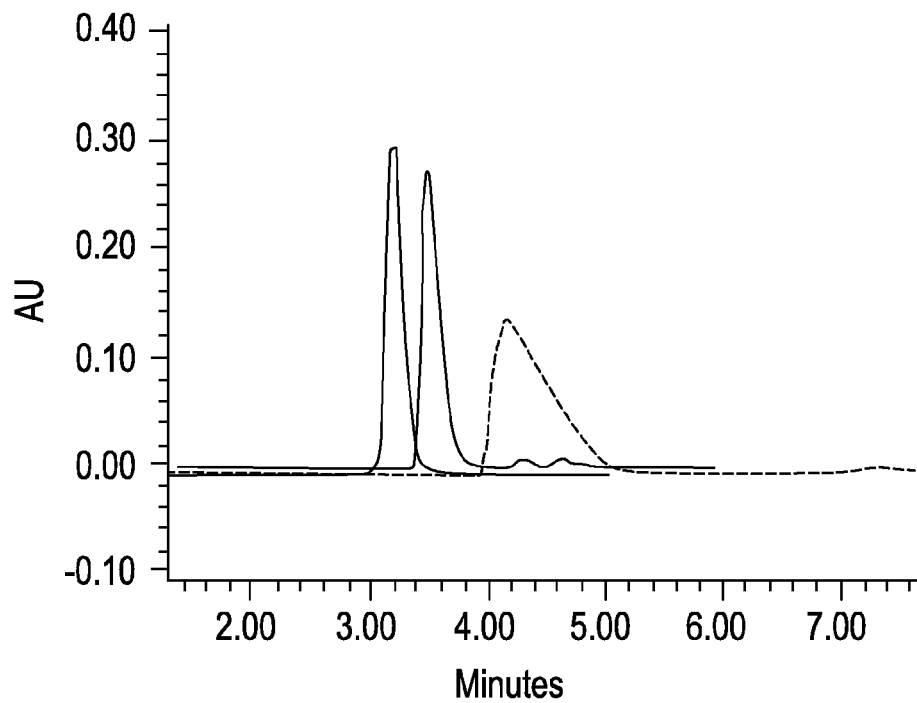
Figure 19B:
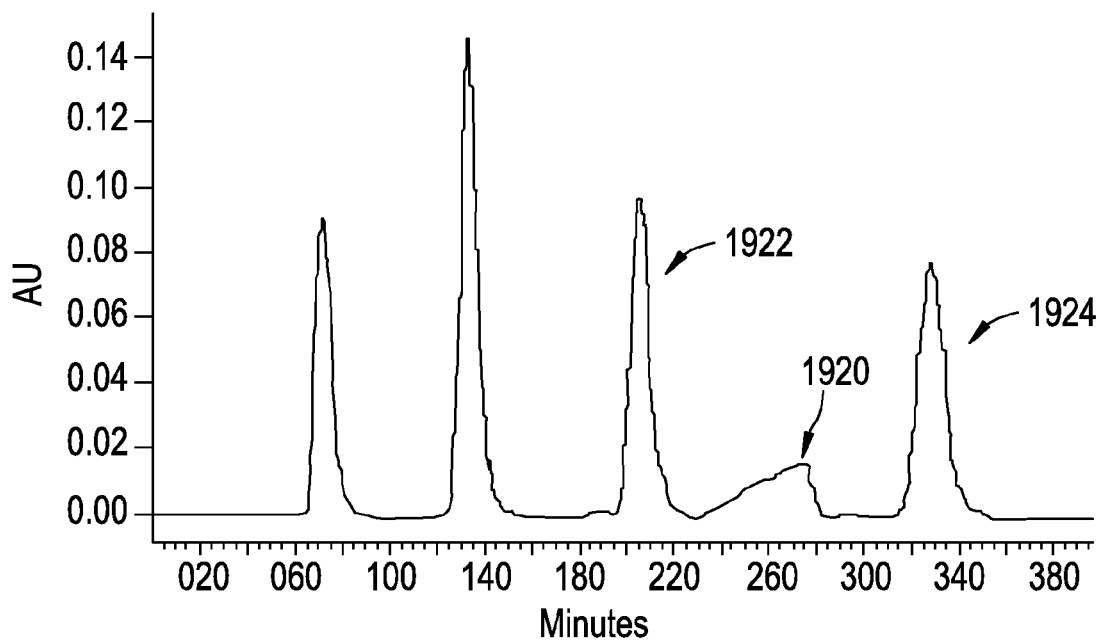
Figure 19C:
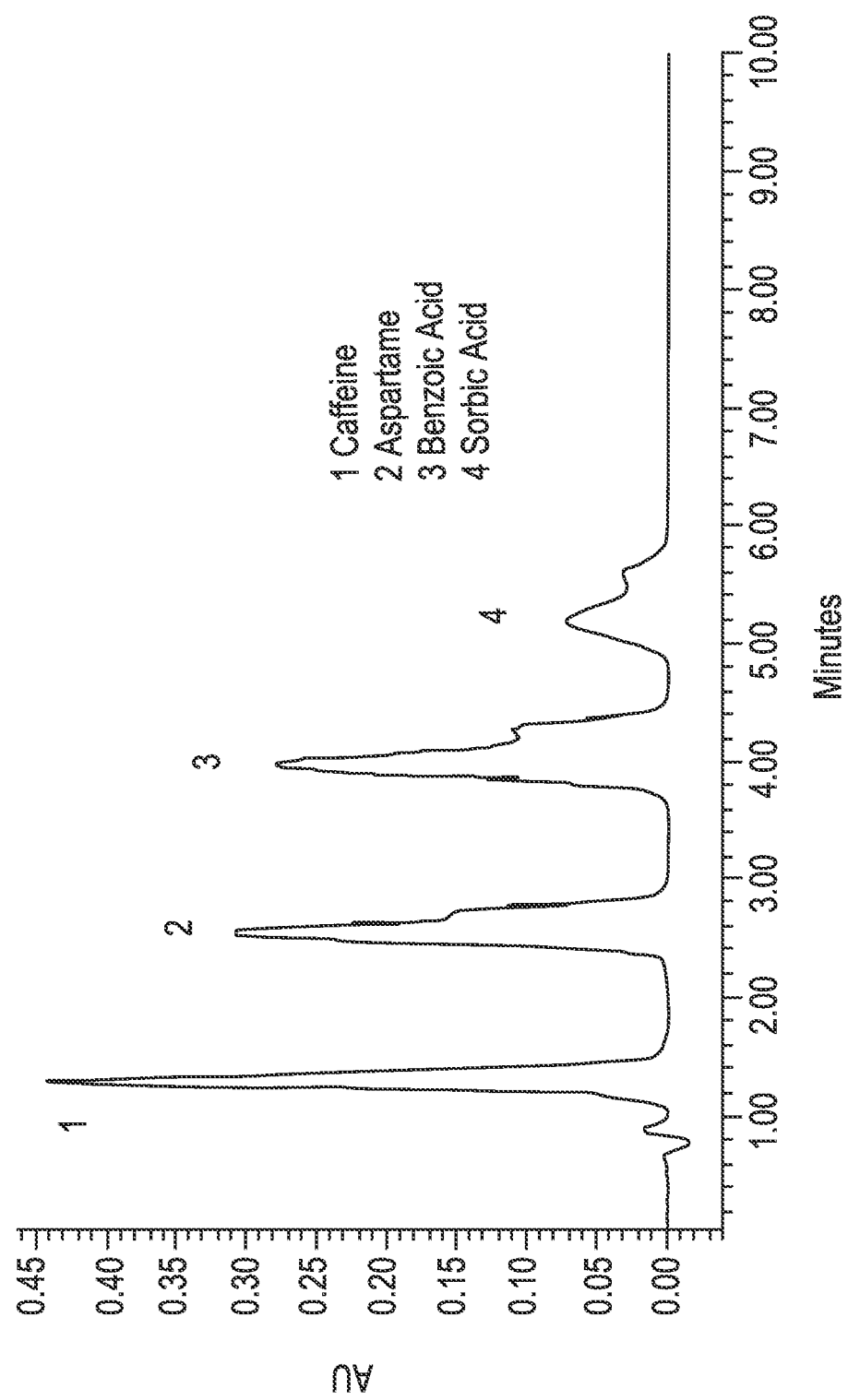
Figure 19D:
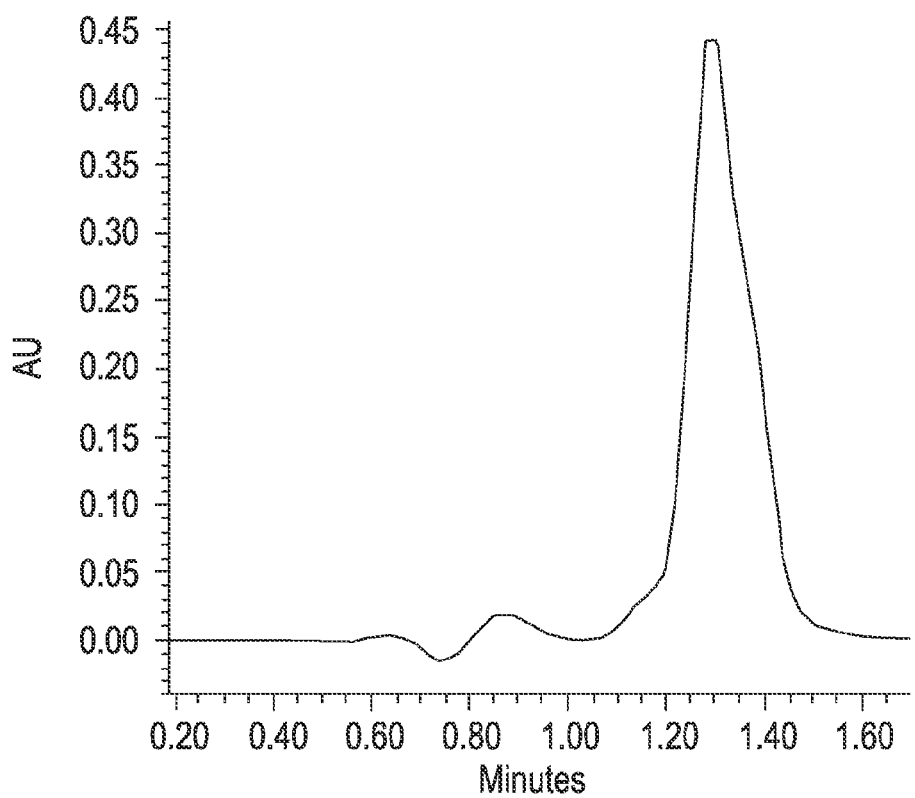
Figure 19E:
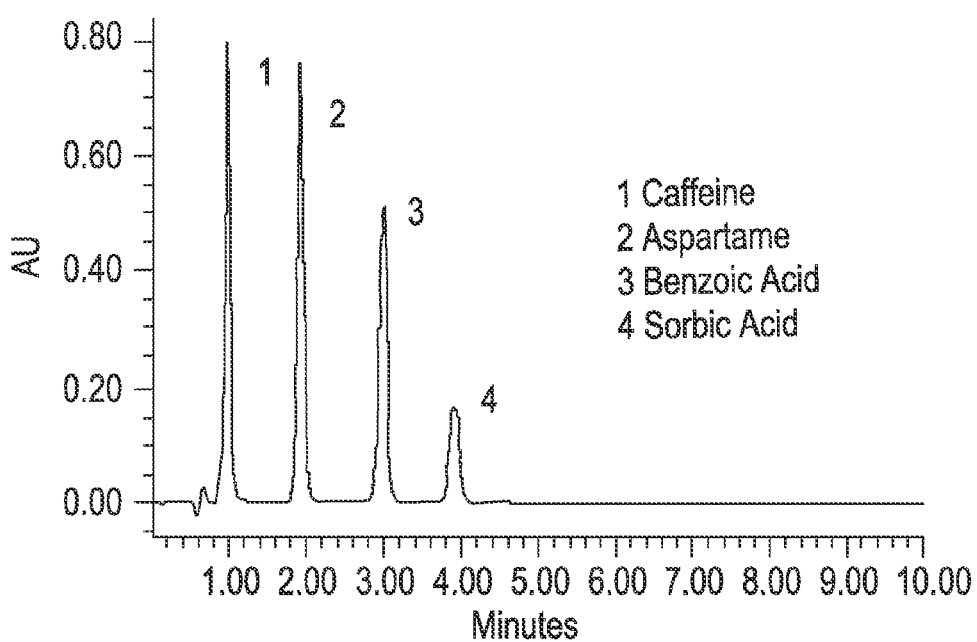

Weak acids and bases that are run in a mobile phase that is near their pK may show tailing even on highly functionalized columns. The problem is typically explained as an ionization problem, specific to the sample, rather than a column interaction problem. FIG. 19A shows aspirin separation. The pKa for aspirin is 3.5. A poorly shaped peak (1920) in a chromatogram is between to well shaped peaks (1922 and 1924) as in FIG. 19B can be indicative of any of a number of problems including, but not limited to: co-eluting peaks; a mixed mode mechanism; a basic compound sticking to silanols; not enough ion-pairing reagent, not enough ionic strength; incorrect pH; and a contaminating peak from a prior injection. FIG. 19C shows a chromatogram of caffeine, aspartame, benzoic acid, and sorbic acid in which all of the peaks of the chromatogram have shoulders and are poorly shaped. FIG. 19D is an expanded view of the caffeine peak showing that a shoulder is present on that peak as well. Consistently poorly shaped peaks is indicative of a mechanical, rather than a chemical, problem. For example, the presence of shoulders can be indicative of a column void or injector failure. In the example chromatograph shown, further analysis demonstrated that the problem was caused by a void in the column. The column was replaced and the sample rerun. The resulting chromatograph is shown in FIG. 19E. All of the peaks are well shaped.

Column Regeneration

Depending on the reason for column failure, some times the column can be regenerated, rather than replaced. However, column regeneration is time consuming and expensive and, even when it works, column efficiency is never completely restored. In some cases, DMSO can be used as a column modifier as it will not damage the column, however, care must be taken as it can stick to the head of the column and adversely affect separations. Cleaning may extend the useful life of the column in such a situation. The following exemplary column regeneration method is provided:
1. Wash with 100% water to remove buffers.
2. Wash with methanol.
3. Wash with THF.
4. Wash with N-heptane.
5. Wash with THF.
6. Wash with methanol.
7. Wash with water.
8. Return to solvent.

After regeneration of the column, it should be checked using the QCRM compositions and methods provided herein to confirm that the column is functioning at an acceptable level.

EXAMPLES

Example 1

Neutrals QCRM

A neutrals QCRM (in this example, including acetone (as a void volume marker) as well as naphthalene and acenaphthene (later eluting neutral compounds)) can be extremely versatile and appropriate for a vast variety of column chemistries and dimensions, and system hardware. It can also be adaptable to a wide variety of separation methods. Similarly, it can alternatively include other combinations of neutral compounds.

The injected quantity of the neutrals QCRM should be scaled for other column diameters. A column calculator (such as an ACQUITY UPLC® Columns Calculator available from Waters Technologies Corporation, Milford Mass.) can be used to properly transfer the separation across column dimensions. The L/dp (length to particle size ratio) for both columns should be kept comparable to maintain resolution.

FIG. 20 shows an example chromatogram obtained for the neutrals suitability mixture using the following column and system. Column: BEH $C_{18}$, 1.7 µm, 2.1×50 mm column; Instrument: ACQUITY UPLC® H-Class System (Waters Technologies Corporation, Milford Mass.). Mobile phases: A: 20 mM potassium phosphate pH 7; B: 10 mM ammonium formate pH 3; C: 10 mM ammonium bicarbonate pH 10; D: acetonitrile. Flow rate: 0.5 mL/minute. Temperature: 30° C.; Detection: UV. Retention times: Acetone ($V_o$): 0.3 min; Naphthalene: 1.5 min; Acenaphthene: 2.6 min.

Example 2

Reversed Phase QCRM

A reversed phase QCRM (in this case, including 7 compounds: uracil (un-retained marker), butyl paraben (weak acid), naphthalene (neutral), propranolol (base), dipropyl-phthalate (polar neutral), acenaphthene (neutral), and amitriptyline (base) at pH 7). These compounds were chosen for their varying chemical properties and retention on reversed-phase stationary phases. Under the appropriate reverse phase method conditions, the compounds can be resolved.

The reversed phase QCRM of Example 2 is significantly more complex than the neutrals QCRM of Example 1, in that it contains compounds which could be challenging to separate. It is designed to provide this complexity and is appropriate when complex assays are routinely performed. It can be used with a variety of column chemistries and dimensions, and system hardware. On different column chemistries or dimensions, methods may need to be modified or re-developed to obtain sufficient resolution.

FIG. 21 shows an example chromatogram of the Reversed-Phase QCRM generated using the following column and system: Column: HSS $C_{18}$, 2.1×50 mm, 1.8 µm column; Instrument: ACQUITY UPLC® HSS System (Waters Technologies Corporation, Milford Mass.). Mobile phase: 65/35 Methanol/20 mM phosphate buffered mobile phase at pH 7; Flow rate: 0.25 mL/min; Temperature: 30 C; Detection: UV at $\lambda=254$ nm; Injection volume: 1.5 µL. Retention times: Amitriptyline: 29 min; Acenaphthene: 24 min; Naphthalene: 11 min; Dipropyl phthalate: 8 min; Butyl paraben: 5 min; Propranolol; 4 min; Uracil ($V_o$); 1 min.

Example 3

Preparative Chromatography Standard

Example 3 shows the results of a UV chromatography dye test QCRM for preparative chromatography generated using the following column and system: Column: 19 mm×50 mm XTerra® column (Waters Technologies Corporation, Milford Mass.) Mobile phase: (A): Water/TFA, 0.1% or Water/formic acid 0.2% (v:v); (B): Acetonitrile/TFA, 0.1% or Acetonitrile/Formic acid 0.2% (v:v); Detection: Waters 2487 UV detector at $\lambda=418$ nm, $\lambda=590$ nm; Injection volume: 100 µL. The tables below show the chromatography conditions used.

Chromatographic Method

| Time | A % | B % | Curve Number |
| --- | --- | --- | --- |
| T = 0 minutes | 95 | 5 | 6 |
| T = 1 minutes | 95 | 5 | 6 |
| T = 7 minutes | 30 | 70 | 6 |
| T = 7.5 minutes | 5 | 95 | 6 |
| T = 8.5 minutes | 5 | 95 | 6 |
| T = 9 minutes | 95 | 5 | 6 |
| T = 10 minutes | 95 | 5 | 6 |

Run Parameters

| Parameter Tab | Settings to be Specified |
| --- | --- |
| General | Step fraction collection to On and peak type to Preparative |
| | Select the Max Fractions Per Injection check box, and specify a value of 10 |
| | Select the Max Tubes Per Injection check box, and specify a value of 10 |
| | Rinse time = 0 |
| | Span = 0.5 amu |
| Timing | Solvent front delay = 0 seconds |
| | Split/Collector delay = seconds, where x = the split/collector delay determined earlier |
| Volume | Minimum fraction width = 3 seconds |
| | Maximum fraction width = 120 seconds |
| | Maximum tube fill = 90% |

Detector Selection

| Detector Type | FractionLynx ™ Method Tab | Settings to be Specified |
|---|---|---|
| 2487 | UV | MIT = 100 |
| | | Peak Start = Leading Edge Gradient % with a value of 30 |
| | | Terminate Peak = Below Gradient % with a value of 60 |
| PDA | PDA | Span = 3 nm |
| | | MIT = 5,000 |
| | | Peak Start = Leading Edge Gradient % with a value of 30 |
| | | Terminate Peak = Below Gradient % with a value of 60 |
| Mass Spec | ES+ | ES+ ion adducts = 1 |
| | | MIT = 5,000,000 |
| | | Peak Start = Use MIT only |
| | | Terminate Peak = Use MIT only |
| Analog | Analog | MIT = 5,000 |
| | | Peak Start = Leading Edge Gradient % with a value of 30 |
| | | Terminate Peak = Below Gradient % with a value of 60 |

FIG. 22A shows an example of the chromatograms obtained for the preparative chromatography standard via UV and MS using an XSelect™ CSH™ C18, 5 μm, 19×50 mm column (Waters Technologies Corporation, Milford Mass.). The chromatograms in FIG. 22B represent typical results of the dye test. The three components of the dye mix have been separated and collected into separate vials labeled 1:16, 1:17 and 1:18 to 1:19. The sample was collected using a photodiode array detector (e.g., A 996 PDA detector available from Waters Technologies Corporation, Milford Mass.). The wavelength values were put in the sample list, and the fraction triggers were set to wavelength λ and B.

Example 4

Preparative Chromatography Mixture

A preparative chromatography mix is 5 mg/mL each of diclofenac sodium salt, diphenhydramine hydrochloride, and flavone in DMSO was subject to liquid chromatography. The chromatograph and the structures of the detected components are provided in FIG. 23.

Storage and Stability

The preparative chromatography mix is 5 mg/mL each of diclofenac sodium salt, diphenhydramine hydrochloride, and flavone in DMSO. The compounds are stable in their original packaging, through the expiration date listed as provided in 1 mL amber ampoule before opening. Once opened the mixture should be used immediately to avoid degradation which could compromise the quantitative benefit.

Recommended Usage

For typical preparative chromatographic analysis on a 4.6×100 mm column, the compound mix was injected at 10 μL. The injected quantity should be scaled for other column diameters. The table below indicated the approximate retention times obtained for the compounds when using an XSelect® CSH C18, 5 μm, 4.6×100 mm, 0.1% FA column (Waters Technologies Corporation, Milford Mass.) and the specified chromatographic method in the table below, as well as the m/z criteria for each compound. A detection wavelength of 220 nm was used and is preferred for sensitivity of all 3 compounds and does not show the sample diluent, DMSO, at the beginning of the chromatogram.

Preparative Mix 186006703 UV and MS

| Compound | Type | MS | Approximate RT (min) |
|---|---|---|---|
| Diclofenac sodium salt | Acid | 296.02 | 9.5 |
| Diphenhydramine hydrochloride | Base | 256.17 | 4.5 |
| Flavone | Neutral | 223.07 | 8.2 |

Chromatographic Method

| Time (min) | Flow (mL/min) | % A | % B | Curve |
|---|---|---|---|---|
| | 1.46 | 95.00 | 5.00 | |
| 12.00 | 1.46 | 5.00 | 95.00 | 6 |
| 14.00 | 1.46 | 5.00 | 95.00 | 6 |
| 14.20 | 1.46 | 95.00 | 5.00 | 6 |
| 20.00 | 1.46 | 95.00 | 5.00 | 6 |

FIG. 24 shows an example of the chromatography obtained for the preparative mix via MS when the method in the above table using a SunFire® C18, 5 um, 4.6×100 mm, 0.1% FA column (Waters Technologies Corporation, Milford, Mass.).

Diclofenac, diphenhydramine, and flavone have the similar chromatographic profiles on each of the columns reviewed.

Columns from Waters Technologies Corporation, Milford, Mass. Recommended to be used with the Preparative Chromatography Mix

| Column Name | Dimensions | Mobile Phase: |
|---|---|---|
| XBridge ® C18, 5 um | 4.6 × 100 mm | 0.1% FA |
| XBridge ® C18, 5 um | 4.6 × 100 mm | 0.1% TFA |
| SunFire ™ C18, 5 um | 4.6 × 100 mm | 0.1% FA |
| SunFire ™ C18, 5 um | 4.6 × 100 mm | 0.1% TFA |
| XSelect ® CSH C18, 5 um | 4.6 × 100 mm | 0.1% FA |
| XSelect ® CSH C18, 5 um | 4.6 × 100 mm | 0.1% TFA |
| XSelect ® CSH Phenyl-Hexyl | 4.6 × 100 mm | 0.1% FA |
| XSelect ® CSH Phenyl-Hexyl | 4.6 × 100 mm | 0.1% TFA |
| XSelect ® CSH Fluoro-Phenyl | 4.6 × 100 mm | 0.1% FA |
| XSelect ® CSH Fluoro-Phenyl | 4.6 × 100 mm | 0.1% TFA |

The following exceptions related to column use are noted:
On the XSelect™ CSH Fluoro Phenyl column (Waters Technologies Corporation, Milford, Mass.). Diclofenac and flavone less than 0.5 minutes apart with 0.1% FA in the mobile phase. They are 0.08 min apart with 0.1% TFA in the mobile phase and diclofenac elutes before flavone. On C18 columns they are about a minute apart. On the XSelect™ Phenyl Hexyl column (Waters Technologies Corporation, Milford, Mass.), diclofenac and flavone are further apart with 0.1% FA in the mobile phase (~1.5 min) than on C18 columns (~1 min).

Example 5

Troubleshooting Common System Problems Using Neutrals QCRM

The troubleshooting compositions and methods provided in this example and throughout the application provide many advantages. For example, using the methods and compositions provided herein, chromatography (e.g., LC, HPLC, UHPLC, SFC, and carbon dioxide based chromatography) system issues can be detected early, minimizing collection of poor quality data. Using a quality standard, such as those provided herein, troubleshooting can be performed faster, reducing overall system downtime. Moreover, a recently repaired instrument can be quickly confirmed to be back in normal operation Chromatography is a powerful analytical method of analysis, however, when chromatography systems begins to malfunction, it can mean a considerable amount of time and resources to fix. Some system problems, such as a leak in the pump, can be noticed by an experienced chromatographer, while other problems, such as improperly connected column outlet tubing, can be a subtle problem and difficult to troubleshoot. By using a QCRM, a chromatographer can more easily detect problems within their system, potentially reducing system downtime.

The neutrals Quality Control Reference Material (QCRM) is a mix of three neutral compounds: acetone, naphthalene, and acenaphthene. These compounds are manufactured with batch-to-batch reproducibility in a controlled setting ensuring consistent results over time. This standard is an ideal solution for system troubleshooting and maintenance as the separation of these compounds can be achieved under common mobile phase conditions with sufficient organic content. In this example, six common chromatographic problems are examined to demonstrate the utility of the neutrals QCRM in rapidly diagnosing problems on a chromatography system. After repairs were made, the neutrals QCRM was used to quickly confirm that the system was back to operating optimally. By using the neutrals QCRM to check system functionality, data quality can be assured and the system can be used with confidence.

It is beneficial to have a system's performance benchmarked, in order to monitor system performance and ensure quality data generation. Subsequently, if any problems arise within the system, the operator can compare the performance after any repairs, to performance before the problem was present. In this example, six common chromatographic issues are examined, using the neutrals QCRM to rapidly diagnose the problem, e.g., poor column performance, leak in pump, poor check valve performance, improper column fitting connections, air bubble in system, and/or error in mobile phase preparation. During this experiment retention time, USP tailing factor, and USP plate count were monitored. Although many other parameters may be monitored, these parameters were chosen since many methods, especially compendial methods, have requirements for these parameters. Furthermore, all of these parameters can be indicators of a malfunctioning system.

Forty-five injections of the neutrals QCRM were run on a recently calibrated ACQUITY UPLC® H-Class column with ACQUITY UPLC® PDA detector (both from Waters Technologies Corporation, Milford, Mass.) for five days, as shown in FIG. 25A, prior to any system malfunction or user error. As part of a system benchmarking process, the operator creates appropriate specifications according to laboratory protocols that the neutrals QCRM must pass in order for the system to be considered working optimally. By creating these specifications, the system performance can be monitored, potentially catching problems before they arise.

To showcase the troubleshooting capability of the neutrals QCRM, the first issue demonstrated is the effect of a failing column on the separation. Over time, with repeated injections, all LC columns will lose their efficiency and ability to separate components of a mixture. In FIG. 25B, the separation of the neutrals QCRM on an ACQUITY UPLC® BEH C18, 2.1×50 mm, 1.7 µm Column (Waters Technologies Corporation, Milford, Mass.) that had been excessively used is shown and compared to the separation obtained on a column with acceptable performance.

As FIG. 25B shows, the failing column is causing peak splitting of both the naphthalene and acenaphthene peaks. Monitoring USP plate count for the acenaphthene peak, the value dropped to approximately 1000 with the failing column, shown in FIG. 25C. After the failing column was replaced with a new column, nine injections of the neutrals QCRM were run. The data from these nine injections, shown in FIG. 25C, is comparable to the benchmarked data, indicating that the system is operating optimally prior to column failure. The low % RSD of the combined retention times after column replacement, as well as the consistent return to comparable plate counts and tailing factors, demonstrate that the system is back to normal performance.

The second system issue demonstrated is malfunctioning pump caused by a leak. Once the leak was induced, the neutrals QCRM was analyzed, shown in FIG. 26A.

When a minor leak was present in the pump, all of the peaks were still eluting within the sample run time; however, there is a shift in retention times and a slight change in the system pressure. With stringent specifications set in the laboratory, the approximate 10% difference in retention times, shown in FIG. 26B, may fall outside of the specifications, alerting the analyst of a potential system issue. Combined with the pressure difference, this may indicate to the analyst that the pump could be malfunctioning. After the pump was repaired, the system was re-checked for performance using the neutrals QCRM. Nine injections of the standard were performed and the data was compiled, shown in FIG. 26B. The combined retention time % RSDs were less than 0.7 for all peaks after the leak was repaired, which confirms that the system was back to normal operation.

A third common system problem is a bad check valve. Check valves help to regulate flow and pressure in a chromatography system. Over time, these valves may stick and become clogged depending on the types of mobile phase used. When they begin to fail, there can be noticeable chromatographic and pressure issues in a system. The separation of the neutrals QCRM on a system with a bad check valve compared to a good check valve is shown in FIG. 27A.

The retention times of all three peaks shift with the bad check valve compared to the good check valve. This slight change in retention time is caused by the check valve not being able to regulate the flow of the mobile phase effectively. In this instance, not only did the retention of the compounds increase, but the plate count dropped by 26% for naphthalene, shown in FIG. 27B. This shift in retention time, as well as the decrease in plate count, may cause a run of standard to fall out of specifications. Once the check valve was replaced, the system was checked for performance once again by running an additional nine injections of neutrals QCRM, shown in FIG. 27B. In this instance, the plate counts and retention times of the nine injections were comparable to the benchmarked data, indicating a normally functioning system after repair of the check valve.

A fourth common mode of failure in an LC system is improper column connection. Improperly connecting the tubing to the column can occur when changing columns and can result in a gap between tubing and column end fittings. This gap can affect peak shape, potentially widening peaks, resulting in excessive peak tailing or shouldering. The separation of the neutrals QCRM on a column with an improper connection compared to a column that is properly connected can be seen in FIG. 28A.

In this example, the separation of the neutrals QCRM with the improper column connection shows only slight changes in the separation compared to the proper column connection. The effect of improper column connections can vary depending on the extent of the gap created. In this case, tailing of the naphthalene peak increases slightly with the poor tubing installation as well as the decreased retention of the acenaphthene peak. These changes could indicate many problems with the system. Each peak is affected differently and as the differences are only slight, they might go unnoticed. In addition to the higher tailing of the naphthalene peak, a drop in plate count is also observed, shown in FIG. 28B. Depending on assays and specifications, this drop in plate count may cause system performance checks to fail. By connecting the column properly and injecting nine injections of the standard, the system performance was re-checked, shown in FIG. 28B. The tailing factor for naphthalene returned to approximately 1.1, and the plate counts increased and returned to the same performance as the benchmarked data, indicating that the system has returned to optimal operation.

A fifth common problem in LC is an air bubble in the solvent line, which can be caused by inadequate system priming or running out of solvent in the solvent bottles. Once an air bubble forms, it can affect the system pressure and mobile phase delivery. The effect of an air bubble on the separation of the neutrals QCRM is shown in FIG. 29A.

With air in the system, the retention time of all the peaks has shifted. The air in the solvent lines or pump can cause improper delivery of the mobile phase, thereby shifting retention time. In this case, a 25% increase in retention of the naphthalene peak was observed, shown in FIG. 29B. By re-priming the system with mobile phase, the air was removed from the system. Looking at the data from nine injections of the neutrals QCRM after removing air from the system, shown in FIG. 29B, the retention times have returned to where they were during system benchmarking, indicating the system no longer has an air bubble.

The final common problem seen in LC that was studied in this application is varying organic composition in the mobile phase, which can happen during mobile phase preparation due to analyst error. Slight variations in mobile phase composition can have effects on chromatographic results, including increasing or decreasing retention times and potentially causing co-elution of peaks. In this application, the percentage of acetonitrile was altered by ±2% for the analysis of the neutrals QCRM. FIG. 30A shows the separation with using mobile phase compositions of 48%, 52%, and 50% (recommended composition) acetonitrile.

Predictably, the varying organic composition has a significant effect on the isocratic separation of the standard. A retention time shift of 25% for the naphthalene peak was observed when the mobile phase contained 48% acetonitrile, while a 21% decrease in retention time occurred when 52% acetonitrile was present in the mobile phase, shown in FIG. 30B. Once the original mobile phase composition (50% acetonitrile) was placed back onto the system, nine injections of the neutrals QCRM were run to re-check the system performance, shown in FIG. 30B, and to demonstrate proper system operation. The retention times of all the peaks were comparable to the benchmarked data, indicating that the mobile phase was made accurately and that the system is functioning as it should. The neutrals QCRM is compatible with many mobile phases, and if the mobile phases for sample analysis are used to both benchmark and troubleshoot the system, the benefits of the neutrals QCRM for troubleshooting mobile phase errors can be realized. While this example focuses on the use of 50% acetonitrile, other mobile phases with sufficient organic composition may be used. Without the use of a standard to check system performance, an error in mobile phase preparation could cause irreproducible chromatography or co-elution of target peaks in real samples, resulting in extensive and unnecessary method development, or reanalysis of the samples. Instead, with proper specifications for the neutrals QCRM, errors in organic composition may be identified before time is invested in sample analysis.

In summary, the neutrals QC Reference Material (QCRM) is a mixture of three neutral compounds that can be separated with common mobile phases with sufficient organic composition, and is compatible with most column chemistries, making it an ideal standard for troubleshooting chromatography system problems. Before the standard can be used as a troubleshooting tool, it is recommended to benchmark the system performance using the standard and create a set of specifications to determine the limits of acceptable data for future runs of the standard. During routine analysis the standard can be used to monitor to the system and if a problem arises, the neutrals QCRM can be run to determine if a system problem exists and to help identify the issue. Once the problem is resolved, the standard can be run again to confirm that the system is back to normal operation.

There are many benefits to using the neutrals QCRM. First, system downtime can be reduced. This allows for a better use of resources, with more samples analyzed and less time spent by analysts trying to fix a system problem. Secondly, as a result of the strict manufacturing process of the standard, errors in suitability standard preparation are mitigated, isolating issues to the system and allowing a chromatographer to identify the problem faster. Lastly, the neutrals QCRM can be used to ensure that a recently repaired system is functioning optimally. This increases the confidence in the data produced after repairs and ensures high quality data generation.

Example 6

Ensuring Data Quality by Benchmarking System Performance Using Waters Neutrals Quality Control Reference Material The neutrals Quality Control Reference Material (QCRM) provided herein is a mixture of three neutral compounds that are an ideal system reference standard. The use of neutral compounds allow the QCRM to be unaffected by mobile phase pH, making it compatible with buffered and non-buffered mobile phases at both high and low pH. Thus, the standard can be analyzed on many different chromatography systems, with different column chemistries, and different mobile phases. The highly controlled manufacturing process of the standard ensures a high quality and reliable standard that can be counted on to produce consistent results over time. This example focuses on how the standard can be used to benchmark and monitor system performance over the life of the system. By using the reference standard to benchmark system performance, data integrity can be monitored and assured.

System performance and data reliability are something that every chromatographer should be conscious of. A system should be monitored regularly to ensure that it is continually performing at an optimum level to generate quality data. The easiest way to evaluate system performance is to routinely use a QCRM standard to benchmark the system when it is performing optimally. At later dates, subsequent injections of standard can be compared to the original data to ensure that the system is still performing well. The neutrals QC Reference Material (NQCRM) is a mixture of three neutral compounds: acetone, naphthalene, and acenaphthene. The separation of these compounds is achieved under common mobile phase conditions with sufficient organic content. FIG. 25B, for example, shows the separation of the neutrals QCRM on an ACQUITY UPLC® BEH C18, 2.1×50 mm, 1.7 µm Column (Waters Technologies Corporation, Milford, Mass.).

In this application, the standard was used to benchmark the system performance of an ACQUITY UPLC® H-Class System (Waters Technologies Corporation, Milford, Mass.) equipped with a PDA detector for a period of five days (120 h). Prior to beginning the experiment, the system was calibrated and performance maintenance was performed to ensure proper operation of the system. Benchmarking a system that is not performing optimally could lead to irregular and unreliable benchmarking results. The neutrals QCRM was injected in triplicate onto an ACQUITY UPLC® BEH C18, 2.1×50 mm, 1.7 µM column (Waters Technologies Corporation, Milford, Mass.) three times a day for five days. The first set of injections was performed in the morning, the second at mid-day, and the third in the late afternoon to simulate the standard being run before, during and after an eight-hour shift. A total of 45 injections were performed over five days (120 h). Retention time (FIG. 31B), USP tailing factor (FIG. 32), and system pressure (FIG. 33) were monitored. These parameters were monitored since they are typically parameters that could indicate a serious system problem. If, for instance, the retention time of the peaks changed significantly, it could indicate a pump issue or an error in mobile phase preparation; while an increase in USP tailing factor could indicate a failing column or that the column outlet fitting is not seated properly.

As the trending data shows, the neutrals QCRM is a valuable tool for benchmarking a system's performance. The data show the high reproducibility of the system over time, with a retention time % RSD<0.7 for all three peaks in the neutrals QCRM standard, as shown in FIG. 31A. The trending data for the USP tailing factor shows very little deviation over the course of the analysis, indicating that the peaks are not changing over time. The system pressure trending data shows very little variation as well, displaying a stable pressure over the course of the experiment. In this experiment, the monitoring of retention time, USP tailing factor, and system pressure was important, since any change in these parameters could indicate a system or column problem, and potential collection of erroneous data for experiments run on the system over these five days.

In addition to monitoring system performance, this data 'benchmarks' a starting point that future injections of the neutrals QCRM can be compared to. After gathering the benchmark data, a set of specifications can be created to monitor the system. After these specifications are created, the QCRM can be run periodically and checked against these specifications to determine if the system is still operating optimally. If the neutrals QCRM falls out of specification, the system may need to be repaired. After these repairs are completed, the neutrals QCRM can be run again and the data can be compared to the specifications to see if the system is working properly.

Monitoring system performance is an important aspect of liquid chromatography that should be performed routinely to ensure the highest quality data generated. Routinely monitoring a system with a well-characterized and controlled standard can lead to early detection of system problems, potentially reducing system downtime.

Example 7

LCMS Quality Control Reference Material Products

The LCMS QCRM is a 9 component mix used to provide a comprehensive reference standard for use with LC/MS or MS instrumentation with a wide variety of conditions and methods. The mixture has at least the following advantages for use in LCMS quality control in that the compounds in this mix give a mixture of responses in ESi (+−) and APCi+ and covers a wide range of m/z. Additionally, the optimized concentrations of the components provide a more equal response by component in ESI+ mode. The components provide a separation in a range of chromatographic conditions used to benchmark instrument performance.

FIG. 34A lists the individual components in the LCMS QCRM Mix with their empirical formulas, exact mass as both $[M+H]^+$ and $[M+H]^-$, and their concentration for analysis. FIG. 34B shows a TOF MS ES+Spectrum of the LCMS QCRM standard using a methanol mobile phase with a SYNAPT®, G2-S MS column (Waters Technologies Corporation, Milford, Mass.) operated in positive ion mode in high resolution mode.

Example 8

Quality Control Reference Material and Benchmarking Instrument Performance

This example is to address the use of a specific type of Reference Material called Quality Control Reference Materials (QCRMs). The rationale for using these QCRMs is establishing quantitative benchmarks for a particular analytical system. The proper use of these materials provides documenting mechanisms to track variances of a analytical and chromatographic system. One of the strongest tools for a chemist is control charting. Control charting can be performed using specific sets of reference materials and methods provided herein, per instrument, to help chemists identify and understand the significance of variances in their data. The following important definitions surrounding "reference materials" are used in this example.

Reference Material—(RM) material, sufficiently homogeneous and stable with reference to specified properties which have been established to be fit for its intended use in measurement or in examination of nominal properties.

Certified Reference Material—(CRM) reference material, accompanied by documentation issued by an authoritative body and providing one or more specified property values with associated uncertainties and traceability, using valid procedures.

Quality Control Reference Material—(QCRM) reference material that is precisely formulated, accurate, consistent from lot to lot, and specifically designed for instrument performance checks including control chart analysis of chromatographic indicators. QCRMs may be documented as a Certified Reference Material.

Reference Material analyses provide information about the performance of analytical instruments. Control charting of the data associated with Quality Control Reference Materials analyses allows for quick visibility of instrument performance and prevents the use of arbitrary criteria in determining whether or not the performance indicators are in control. In addition to providing real-time instrument performance data, control charting provides visibility into potential problems and allows for proactive maintenance and the implementation of preventive actions. One of the keys to generating valuable control charting data is using a reference material that is accurate, consistent from lot to lot, and appropriate for the analyses being conducted. The quality of the reference material is paramount to the evaluation of the analytical data and the instrument performance. It is critical to understand the uncertainty for the parameters of interest of the reference material. This provides an understanding of whether or not an observed variance originates from the tolerances of the reference material or, more often, from an unexpected system variance. When observed system variability welt exceeds any variation associated with the manufactured reference material, investigation of the system is warranted. The most powerful way to use the Quality Control Reference Materials provided herein is analyzing them routinely on an analytical or chromatographic system and then control charting the critical results. These current and historical data identify areas of excess variability warranting concern.

The first step in establishing a control charting program is defining the performance indicators to be tracked and sourcing an appropriate reference standard. Using high performance liquid chromatography (HPLC) as an example, although any type of liquid chromatography can be used, common instrument performance indicators are peak width or peak area, retention time, and peak resolution. Each of these parameters can be tracked and evaluated in real time by control charting the results of the analysis of an appropriate reference standard. In the case of retention time monitoring, the neutrals QCRM provided herein is appropriate for most analytical chromatographic systems using UV detection. Establishing the frequency for reference material control charting is a function of risk analysis and understanding the stability of the analytical system being monitored. When control charting identifies an out of control situation, all data generated back to the last documented in-control point on the control chart are in jeopardy. If many analyses have been conducted between the two sets of reference material data, all of that data may have to be recalculated or even invalidated, which can be a very expensive proposition. Control charting in analytical chemistry is a fairly easy and inexpensive process, as compared to the destructive testing of a product in a manufacturing environment, many labs will analyze and control chart reference standards on a daily basis (e.g., on all working days). At a minimum, control charting should be done after each calibration or maintenance to the instrument. A control charting program should be established for each instrument and set of analytical conditions. Comparing data from multiple instruments that may have different operating conditions and are undergoing maintenance at different times can lead to a loss of sensitivity in the control charting process and potential unrecognized problems. Additionally, where multiple analysts are routinely operating an instrument it is ideal to have a control chart for each analyst. If personnel-specific control charts are unfeasible, it is critical to use multiple analysts' data to establish initial control limits.

Control charting data is generally collected in a spreadsheet software program such as MICROSOFT® EXCEL®. Each time the reference material is analyzed, the data for the performance indicator(s) being tracked should be entered into the spreadsheet along with the analysis date. FIG. 35A shows an example table of retention time data being tracked over a period of five consecutive days at three injections per day.

Once at least seven data points have been collected, the mean and standard deviation of the data should be calculated for each performance indicator. Using the mean and standard deviation, warning and control limits can be calculated. The data used to initially calculate limits can be gathered over a condensed time frame to speed up the use of the control chart, but the data should be collected over at least a few days, and using multiple analysts unless analyst-specific control charts will be generated.

Warning limits are generally set to the mean plus and minus two standard deviations (UWL and LWL, respectively) and control limits at the mean plus and minus three standard deviations (UCL and LCL, respectively), however other tolerances and variants can be used.

Using the data in FIG. 35A, the results presented in FIG. 35B were calculated.

A graph with time as the independent variable and instrument response as the dependent variable was created using the data generated by the analysis. Lines indicate the warning and control limits calculated from the data. The control chart created using the data from this example, with its associated limits, is shown in FIG. 35C.

Each time a new data point is added to the spreadsheet, the graph should be updated to show its location relative to the limits. If the newest data point is within the warning limits, this is an indication that the instrument is in control. When a data point falls outside of the warning limits, but is still within the control limits, this is an indication that the data is beginning to trend toward being out of control. A single data point between the warning and control limits does not generally require corrective action, but an investigation into possible causes should be completed. The data may be indicating, for example, that the analytical column, or some other replaceable item, is nearing the end of its useful life, and being able to anticipate this based on the control chart data can save time and money. If there are two consecutive points between the warning and control limits, an investigation should always be performed and corrective action implemented. If a result falls outside of the control limits, all data generated back to the last in-control data point needs to be reviewed to have its validity determined and corrective action must be implemented and verified prior to using the instrument again.

As discussed herein, control charting the results of QCRM specifically designed for the analysis of critical instrument performance indicators allows for real-time evaluation of instrument performance. By frequently monitoring their analytical instruments in this way, labs can significantly reduce system down time and prevent costly data errors. Choosing an appropriate frequency, selecting a reference material that is consistent from sample to sample and lot to lot, and appropriate for the analysis being conducted, are all critical aspects of a successful control charting program.

The power of using standards of known traceability and uncertainty as part of this process allow the variations to be documented with confidence and defensibility. When the parameters of interest are well defined and consistent, decisions to continue analysis, to review data or to abandon an analytical run can be made quickly with supporting information to justify the prompt decision.

This concept can be expanded beyond a single instrument to multiple instruments in a single laboratory or to multiple facilities so long as the same source of reference material is used. Using single source reference materials opens the door for making intra- and inter-laboratory data comparisons. In today's global manufacturing environment these data comparisons become more important and now with QCRM designed only for this purpose, possible.

Example 9

Ensuring Data Quality and Facilitating Rapid System Troubleshooting Using a QCRM Neutrals Quality Control Reference Material (QCRM) is a mixture of an un-retained peak and two neutral compounds that are an ideal system reference standard. The use of neutral compounds allow the QCRM to be unaffected by mobile phase pH, making it compatible with buffered and non-buffered mobile phases at both high and low pH. Thus, the standard can be analyzed on many different LC systems, with different column chemistries, and different mobile phases. The highly controlled manufacturing process of the standard ensures a high quality and reliable standard that can be counted on to produce consistent results over time.

This example focuses on how the standard can be used to benchmark and monitor system performance over the life of the system. Additionally, to demonstrate the utility of the neutrals QCRM in rapidly diagnosing problems on an LC system, three common chromatographic problems are examined. By using the neutrals QCRM reference standard to benchmark system performance and to check system functionality, data integrity can be monitored and the system can be used with confidence.

Materials and Methods

An ACQUITY® UPLC H-Class column (Waters Technologies Corporation, Milford, Mass.) was run using the following conditions:
  Mobile phase: 50:50 Acetonitrile:Water
  Separation mode: Isocratic
  Detection (PDA): UV 254 nm
  Column: ACQUITY® UPLC BEH C18 2.1×50 mm 1.7 µM
  Temperature: 30° C.
  Needle wash: 50:50 Acetonitrile:Water
  Sample purge: 50:50 Acetonitrile:Water
  Seal wash: 50:50 Methanol:Water
  Flow rate: 0.6 mL/min
  Injection volume: 1 µL
  A vial of Waters® Neutral QC Reference Material (PN: 166006360) was opened and transferred into an LC6C Certified Clear Qsert Vial (PN: 186001126C) for injection.

Results and Discussion

System Benchmarking

A system should be monitored regularly to ensure that it is continually performing at an optimum level to generate quality data. The easiest way to evaluate system performance is to routinely use a QCRM standard to benchmark the system when it is performing optimally. At later dates, subsequent injections of standard can be compared to the original data to ensure that the system is still performing well. The separation of the neutrals QCRM compounds is achieved under common mobile phase conditions with sufficient organic content. A chromatograph of Isocratic Separation of the neutrals QCRM using 50% acetonitrile in water as the mobile phase was obtained for reference and future 'benchmarking'. Exemplary chromatographs are shown in FIG. 20.

The neutrals QCRM is a valuable tool for 'benchmarking' a starting point that future injections can be compared to. After gathering the benchmark data, a set of specifications can be created to monitor the system, The QCRM can then be run periodically and checked against these specifications to determine if the system is still operating optimally. If the neutrals QCRM falls out of specification, the system may need to be repaired and recently collected data may need to be evaluated.

In this application, the standard was used to benchmark the system performance for a period of five days (120 hours). Prior to beginning the experiment, the system was calibrated and performance maintenance was performed to ensure proper operation of the system. The neutrals QCRM was injected in triplicate, three times a day for five days. A total of 45 injections were performed over five days. Although many parameters can be monitored, retention time, USP tailing factor, USP plate count, and system pressure were deemed most relevant for this experiment.

Exemplary trending data for the retention time of naphthalene, acetone, and acenaphthene and for system pressure over the course of system performance benchmarking (120 hrs.) are shown in FIGS. 31 and 32.

As part of a system benchmarking process, the operator should create appropriate specifications based on trending data (FIGS. 31 and 32) and according to laboratory protocols, for the system to be considered working optimally. By creating these specifications, the system performance can be monitored, potentially catching problems before they arise.

Subsequent to 'benchmarking' the system, if any problems arise within the system, the operator can compare the performance after any repairs to performance before the problem was present. In this application, three common chromatographic issues are examined, using the neutrals QCRM to rapidly diagnose the problem.

System Troubleshooting

Once a system has been 'benchmarked', if any problems arise within the system, the operator can compare the performance after any repairs to performance before the problem was present. In this application, three common chromatographic issues are examined, using the neutrals QCRM to rapidly diagnose the problem.

Declining Column Performance

Over time, with repeated injections, all LC columns will lose their efficiency and ability to separate components of a mixture, FIG. 25B shows an exemplary chromatograph in which the separation of the neutrals QCRM on a column that had been excessively used is shown and compared to the separation obtained on a column with acceptable performance.

As FIG. 25B shows, the falling column is causing peak splitting of both the naphthalene and acenaphthene peaks. Monitoring USP plate count for the acenaphthene peak, the USP plate count dropped significantly with the falling column (FIG. 25C). After the failing column was replaced with a new column, nine injections of the neutrals QCRM were run. The low % RSD of the combined retention times after column replacement, as well as the return to 'benchmarked' plate counts and tailing factors demonstrate that the system is back to normal performance.

Improper Column Connections

Improperly connecting the tubing to the column can occur when changing columns and can result in a gap between tubing and column end fittings. This gap can affect peak shape, potentially widening peaks, resulting in excessive peak tailing or shouldering. Exemplary chromatographs show the separation of the neutrals QC Reference Material on a column with an improper connection compared to a column that is properly connected can be seen in FIG. 28A.

In this example, the separation of the neutrals QCRM with the improper column connection shows only slight changes in the separation compared to the proper column connection. The effect of improper column connections can vary depending on the extent of the gap created. In this case, tailing of the naphthalene peak increases slightly with the poor tubing installation as well as the decreased retention of the acenaphthene peak. In addition to the higher tailing of the naphthalene peak, a drop in plate count is also observed (FIG. 28B).

By connecting the column properly and injecting nine injections of the standard, the system performance was re-checked (FIG. 29B). The tailing factor plate counts returned to the same levels as the benchmarked data, indicating that the system has returned to optimal operation.

CONCLUSIONS

A benchmarked system with operational specifications can help in the early detection of system problems, potentially reducing system downtime, helping to prevent the collection of inaccurate data, and helping to avoid unnecessary sample loss.

The highly reproducible neutrals QCRM can isolate system problems, potentially reducing the time needed for system troubleshooting, A recently repaired system can be checked to ensure optimal operation by comparing data from the separation of the neutrals QCRM after repairs to system benchmarking data and specifications.

From the foregoing it will be appreciated that, although specific embodiments of the invention have been described herein for purposes of illustration, various modifications may be made without deviating from the spirit, and scope of the invention. Accordingly, the invention is not limited except as by the appended claims.

We claim:

1. A method for chromatographic analysis comprising:
obtaining a chromatogram from a reference material using a chromatographic system, wherein the reference material comprises a standardized formulation of compounds including acetone, naphthalene, and acenaphthene that can be used for benchmarking and troubleshooting the chromatographic system;
evaluating a difference between the chromatogram and a benchmark for the reference material on the chromatography system; and
(i) analyzing a sample potentially comprising an analyte of interest, wherein the analyte of interest does not comprise any of the compounds of the standardized formulation, or compounds substantially similar thereto, if the difference between the chromatogram and the benchmark is within a predetermined tolerance, or (ii) troubleshooting the chromatography system using the chromatogram if the difference between the chromatogram and the benchmark is not within the predetermined tolerance.

2. The method of claim 1, wherein the analyte of interest comprises a neutral compound.

3. The method of claim 1, wherein the protocol for obtaining the chromatogram from the reference material is different from the protocol for analyzing the sample.

4. The method of claim 1, wherein the system has been calibrated using a calibrator that is different than the reference material.

5. The method of claim 1, wherein the predetermined tolerance is about three standard deviations.

6. A method for chromatographic analysis comprising:
obtaining a chromatogram from a reference material using a chromatographic system, wherein the reference material comprises a standardized formulation of compounds including acetaminophen, caffeine, sulfaguanidine, sulfadimethoxine, Val-Tyr-Val, zerapamil, terenadine, leucine-enkephalin, and reserpine that can be used for benchmarking and troubleshooting the chromatographic system;
evaluating a difference between the chromatogram and a benchmark for the reference material on the chromatography system; and
(i) analyzing a sample potentially comprising an analyte of interest, wherein the analyte of interest does not comprise any of the compounds of the standardized formulation, or compounds substantially similar thereto, if the difference between the chromatogram and the benchmark is within a predetermined tolerance, or (ii) troubleshooting the chromatography system using the chromatogram if the difference between the chromatogram and the benchmark is not within the predetermined tolerance.

7. The method of claim 6, wherein the chromatographic system comprises a liquid chromatography-mass spectroscopy ("LC-MS") system.

8. The method of claim 6, wherein the protocol for obtaining the chromatogram from the reference material is different from the protocol for analyzing the sample.

9. The method of claim 6, wherein the system has been calibrated using a calibrator that is different than the reference material.

10. The method of claim 6, wherein the predetermined tolerance is about three standard deviations.

11. A method for chromatographic analysis comprising:
obtaining a chromatogram from a reference material using a chromatographic system, wherein the reference material comprises a standardized formulation of compounds including diphenhydramine, flavone, and diclofenac that can be used for benchmarking and troubleshooting the chromatographic system;
evaluating a difference between the chromatogram and a benchmark for the reference material on the chromatography system; and
(i) analyzing a sample potentially comprising an analyte of interest, wherein the analyte of interest does not comprise any of the compounds of the standardized formulation, or compounds substantially similar thereto, if the difference between the chromatogram and the benchmark is within a predetermined tolerance, or (ii) troubleshooting the chromatography system using the chromatogram if the difference between the chromatogram and the benchmark is not within the predetermined tolerance.

12. The method of claim 11, wherein the chromatographic system comprises a preparative chromatography system.

13. The method of claim 11, wherein the protocol for obtaining the chromatogram from the reference material is different from the protocol for analyzing the sample.

14. The method of claim 11, wherein the system has been calibrated using a calibrator that is different than the reference material.

15. The method of claim 11, wherein the predetermined tolerance is about three standard deviations.

16. A chromatographic system quality control reference material comprising:
   a standardized formulation having a predetermined concentration of acetone, a predetermined concentration of naphthalene, and a predetermined concentration of acenaphthene,
   wherein the standardized formulation is adapted for benchmarking and troubleshooting a chromatographic system in the analysis of a sample potentially comprising an analyte of interest, and wherein the analyte of interest does not comprise any acetone, napthaline, acenaphthene, or compounds substantially similar thereto.

17. The chromatographic system quality control reference material of claim 16, wherein:
   the predetermined concentration of acetone is about 10 μL/mL;
   the predetermined concentration of naphthalene is about 25 μg/mL; and
   the predetermined concentration of acenaphthene is about 0.40 μg/mL.

18. A chromatographic system quality control reference material comprising:
   a standardized formulation having a predetermined concentration of acetaminophen, a predetermined concentration of caffeine, a predetermined concentration of sulfaguanidine, a predetermined concentration of sulfadimethoxine, a predetermined concentration of Val-Tyr-Val, a predetermined concentration of zerapamil, a predetermined concentration of terenadine, a predetermined concentration of leucine-enkephalin, and a predetermined concentration of reserpine,
   wherein the standardized formulation is adapted for benchmarking and troubleshooting a chromatographic system in the analysis of a sample potentially comprising an analyte of interest, wherein the analyte of interest does not comprise any acetaminophen, caffeine, sulfaguanidine, sulfadimethoxine, Val-Tyr-Val, zerapamil, terenadine, leucine-enkephalin, reserpine, or compounds substantially similar thereto.

19. The chromatographic system quality control reference material of claim 18, wherein:
   the predetermined concentration of acetaminophen is about 10 μg/mL;
   the predetermined concentration of caffeine is about 1.5 μg/mL;
   the predetermined concentration of sulfaguanidine is about 5 μg/mL;
   the predetermined concentration of sulfadimethoxine is about 1 μg/mL;
   the predetermined concentration of Val-Tyr-Val is about 2.5 μg/mL;
   the predetermined concentration of zerapamil is about 0.2 μg/mL;
   the predetermined concentration of terenadine is about 0.2 μg/mL;
   the predetermined concentration of leucine-enkephalin is about 2.5 μg/mL; and
   the predetermined concentration of reserpine is about 0.6 μg/mL.

20. A chromatographic system quality control reference material comprising:
   a standardized formulation having a predetermined concentration of diphenhydramine, a predetermined concentration of flavone, and a predetermined concentration of diclofenac,
   wherein the standardized formulation is adapted for benchmarking and troubleshooting a chromatographic system in the analysis of a sample potentially comprising an analyte of interest, wherein the analyte of interest does not comprise any diphenhydramine, flavone, diclofenac, or compounds substantially similar thereto.

21. The chromatographic system quality control reference material of claim 20, wherein:
   the predetermined concentration of diphenhydramine is about 5 mg/mL;
   the predetermined concentration of flavone is about 5 mg/mL; and
   the predetermined concentration of diclofenac is about 5 mg/mL.

* * * * *